US011744886B2

(12) United States Patent
Mutzke et al.

(10) Patent No.: US 11,744,886 B2
(45) Date of Patent: *Sep. 5, 2023

(54) METHOD FOR PRODUCING RNA COMPOSITIONS

(71) Applicant: CureVac Manufacturing GmbH, Tübingen (DE)

(72) Inventors: Thorsten Mutzke, Reutlingen (DE); Markus Kreuz, Kohlberg (DE); Stefanie Sewing, Tübingen (DE); Fabian Johannes Eber, Stuttgart (DE); Wenke Wagner, Reutlingen (DE); Michael Sonntag, Tübingen (DE); Michael Wiggenhorn, Munich (DE); Katharina Kolland, Augsburg (DE)

(73) Assignee: CureVac Manufacturing GmbH, Tübingen (DE)

( * ) Notice: Subject to any disclaimer, the term of this patent is extended or adjusted under 35 U.S.C. 154(b) by 681 days.

This patent is subject to a terminal disclaimer.

(21) Appl. No.: 16/838,746

(22) Filed: Apr. 2, 2020

(65) Prior Publication Data

US 2020/0246451 A1    Aug. 6, 2020

Related U.S. Application Data

(63) Continuation of application No. 15/566,010, filed as application No. PCT/EP2016/000607 on Apr. 13, 2016, now Pat. No. 10,653,768.

(30) Foreign Application Priority Data

Apr. 13, 2015 (WO) .................. PCT/EP2015/000771

(51) Int. Cl.
| A61K 39/145 | (2006.01) |
| A61K 48/00 | (2006.01) |
| A61K 47/64 | (2017.01) |
| A61K 9/51 | (2006.01) |
| A61K 39/12 | (2006.01) |
| A61K 39/00 | (2006.01) |

(52) U.S. Cl.
CPC .......... *A61K 39/145* (2013.01); *A61K 9/5169* (2013.01); *A61K 9/5192* (2013.01); *A61K 39/12* (2013.01); *A61K 47/646* (2017.08); *A61K 47/6455* (2017.08); *A61K 2039/55555* (2013.01); *C12N 2760/16134* (2013.01)

(58) Field of Classification Search
None
See application file for complete search history.

(56) References Cited

U.S. PATENT DOCUMENTS

| 10,653,768 B2 * | 5/2020 | Mutzke ................ A61K 9/5169 |
| 2004/0142025 A1 | 7/2004 | Maclachlan et al. |
| 2005/0032730 A1 | 2/2005 | Von der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0130588 A1 | 5/2010 | Yaworski et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0171241 A1 | 7/2013 | Geall |
| 2013/0195969 A1 | 8/2013 | Geall et al. |
| 2013/0202684 A1 | 8/2013 | Geall et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |

(Continued)

FOREIGN PATENT DOCUMENTS

| WO | WO 2009-144230 | 12/2009 |
| WO | WO 2012-094574 | 7/2012 |

(Continued)

OTHER PUBLICATIONS

Lim, et al. (2014) "Ultra-High Throughput Synthesis of Nanoparticles with Homogeneous Size Distribution Using a Coaxial Turbulent Jet Mixer", ACS Nano, 8(6): 6056-65. (Year: 2014).*
Badilescu, et al. (2012) "Microfluidics-Nano-Integration for Synthesis and Sensing", Polymers, 4: 1278-10. (Year: 2012).*
Jensen, et al. (2010) "Spray drying of siRNA-containing PLGA nanoparticles intended for inhalation", Journal of Controlled Release, 142: 138-45. (Year: 2010).*
Sodium acetate trihydrate buffer, located at https://hamptonresearch.com/product_detail.aspx?cid-4&sid-70&pid-133, Hampton Research, 2008.
Belliveau et al., "Microfluidic synthesis of highly potent limit-size lipid nanoparticles for in vivo delivery of siRNA," *Molecular Therapy Nucleic Acids*, 1(8):e37, 2012.

(Continued)

*Primary Examiner* — Robert M Kelly
(74) *Attorney, Agent, or Firm* — Parker Highlander PLLC

(57) ABSTRACT

The present invention relates to a method for producing a liquid composition comprising a nanoparticle comprising at least one RNA and at least one cationic or polycationic compound, advantageously on a large scale suitable for pharmaceutical applications. The present invention further concerns the use of the inventive method in the manufacture of a medicament or a vaccine. Furthermore, the invention relates to compositions containing the RNA-comprising nanoparticle, and to pharmaceutical compositions comprising the same.

35 Claims, 16 Drawing Sheets

Specification includes a Sequence Listing.

(56) References Cited

U.S. PATENT DOCUMENTS

| | | |
|---|---|---|
| 2014/0044772 A1 | 2/2014 | Maclachlan et al. |
| 2014/0141070 A1 | 5/2014 | Geall et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0151284 A1 | 6/2016 | Heyes et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von eer Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |

FOREIGN PATENT DOCUMENTS

| | | |
|---|---|---|
| WO | WO 2012/170889 | 12/2012 |
| WO | WO 2013/177419 | 11/2013 |
| WO | WO 2016-107877 | 7/2016 |
| WO | WO 2016-165831 | 10/2016 |
| WO | WO 2016-174227 | 11/2016 |
| WO | WO 2016-174271 | 11/2016 |
| WO | WO 2016-176330 | 11/2016 |
| WO | WO 2016-184575 | 11/2016 |
| WO | WO 2016-184576 | 11/2016 |
| WO | WO 2016-184822 | 11/2016 |
| WO | WO 2016-193206 | 12/2016 |
| WO | WO 2016-193226 | 12/2016 |
| WO | WO 2016-203025 | 12/2016 |
| WO | WO 2017-001058 | 1/2017 |
| WO | WO 2017-009376 | 1/2017 |
| WO | WO 2017-021546 | 2/2017 |
| WO | WO 2017-025120 | 2/2017 |
| WO | WO 2017-025447 | 2/2017 |
| WO | WO 2017-036580 | 3/2017 |
| WO | WO 2017/049245 | 3/2017 |
| WO | WO 2017/075531 | 5/2017 |

OTHER PUBLICATIONS

Geall et al., "Nonviral delivery of self-amplifying RNA vaccines," *Proceedings of the National Academy of Sciences*, 109(36):14604-14609, 2012.

Hsu et al., "Cationic lipid nanoparticles for therapeutic delivery of siRNA and miRNA to murine liver tumor," *Nanomedicine*, 9(8): 1169-1180, 2013.

Liu et al., "Efficient delivery of NF-[kappa] B siRNA to human retinal pigment epithelial cells with hyperbranched cationic polysaccharide derivative-based nanoparticles," *Int. J. Nanomed.*, 10:2735-2749, 2015.

Office Action issued in U.S. Appl. No. 15/566,010, dated May 15, 2019.

PCT International Preliminary Report on Patentability issued in corresponding PCT Application No. PCT/EP2016/000607, dated Oct. 17, 2017.

PCT International Search Report and Written Opinion issued in corresponding PCT Application No. PCT/EP2016/000607, dated Jun. 6, 2016.

Buse & El-Aneed, "Properties, engineering and applications of lipid-based nanoparticle drug-delivery systems: current research and advances," *Nanomedicine (Lond)*, 5(8):1237-60, 2010.

Huang & Liu, "In Vivo Delivery of RNAi with Lipid-Based Nanoparticles," *Annu. Rev. Biomed. Eng.*, 13:507-30, 2011.

Leung et al., "Lipid Nanoparticles Containing siRNA Synthesized by Microfluidic Mixing Exhibit an Electron-Dense Nanostructured Core," *J. Phys. Chem. C. Nanomater. Interfaces* 116(34):18440-18450, 2012.

Leung et al., "Microfluidic Mixing: A General Method for Encapsulating Macromolecules in Lipid Nanoparticle Systems," *J. Phys. Chem. B* 119:8698-8706, 2015.

Midoux & Pichon, "Lipid-based mRNA vaccine delivery systems," *Expert Rev. Vaccines*, 14(2):221-234, 2015.

Puri et al., "Lipid-Based Nanoparticles as Pharmaceutical Drug Carriers: From Concepts to Clinic," *Crit. Rev. Ther. Drug Carrier Syst.* 26(6):523-580, 2009.

Reichmuth et al., "mRNA vaccine delivery using lipid nanoparticles," *Ther. Deliv.* 7(5):319-334, 2016.

Su et al., "In vitro and in vivo mRNA delivery using lipid-enveloped pH-responsive polymer nanoparticles," *Mol Pharm.*, 8(3): 774-787, 2011.

Wu & McMillan "Lipidic Systems for In Vivo siRNA Delivery," *The AAPS Journal*, 11(4):639-652, 2009.

Xue et al., "Lipid-Based Nanocarriers for RNA Delivery," *Current Pharmaceutical Design* 21:3140-3147, 2015.

\* cited by examiner

R2564 (SEQ ID NO: 1)

```
GGGGCGCUGCCUACGGAGGUGGCAGCCAUCUCCUUCUCGGCAUCAAGCUUACCAUGAAGG
CCAUCCUGGUGGUCCUCCUGUACACCUUCGCCACCGCGAACGCCGACACGCUGUGCAUCG
GCUACCACGCCAACAACAGCACCGACACCGUGGACACCGUGCUCGAGAAGAACGUCACGG
UGACCCACUCCGUGAACCUGCUGGAGGACAAGCACAACGGGAAGCUCUGCAAGCUGCGGG
GCGUCGCCCCGCUGCACCUCGGGAAGUGCAACAUCGCCGGCUGGAUCCUGGGGAACCCGG
AGUGCGAGAGCCUGUCCACCGCGAGCUCCUGGAGCUACAUCGUGGAGACCUCCAGCUCCG
ACAACGGCACGUGCUACCCCGGCGACUUCAUCGACUACGAGGAGCUCCGCGAGCAGCUGA
GCUCCGUGAGCUCCUUCGAGCGGUUCGAGAUCUUCCCCAAGACCAGCUCCUGGCCCAACC
ACGACAGCAACAAGGGGGUCACCGCCGCCUGCCCGCACGCCGGCGCGAAGUCCUUCUACA
GAACCUGAUCUGGCUCGUGAAGAAGGGGAACAGCUACCCCAAGCUGUCCAAGAGCUACA
UCAACGACAAGGGCAAGGAGGUGCUGGUCCUCUGGGGGAUCCACCACCCCAGCACCUCCG
CCGACCAGCAGAGCCUGUACCAGAACGCCGACGCCUACGUGUUCGUGGGCUCCAGCCGCU
ACUCCAAGAAGUUCAAGCCCGAGAUCGCCAUCCGGCCGAAGGUCCGCGACCAGGAGGGCC
GGAUGAACUACUACUGGACGCUGGUGGAGCCCGGGGACAAGAUCACCUUCGAGGCGACCG
GCAACCUCGUGGUCCCCGCUACGCCUUCGCCAUGGAGCGGAACGCCGGGAGCGGCAUCA
UCAUCUCCGACACCCCCGUGCACGACUGCAACACGACCUGCCAGACCCCGAAGGGCGCCA
UCAACACCAGCCUGCCCUUCCAGAACAUCCACCCCAUCACGAUCGGGAAGUGCCCCAAGU
ACGUGAAGUCCACCAAGCUGCGCCUCGCGACCGGCCUGCGGAACGUCCCGAGCAUCCAGU
CCCGCGGGCUGUUCGGCGCCAUCGCCGGGUUCAUCGAGGGCGGCUGGACCGGGAUGGUGG
ACGGCUGGUACGGGUACCACCACCAGAACGAGCAGGGCAGCGGGUACGCCGCCGACCUCA
AGUCCACGCAGAACGCGAUCGACGAGAUCACCAACAAGGUGAACAGCGUCAUCGAGAAGA
UGAACACCCAGUUCACCGCCGUGGGCAAGGAGUUCAACCACCUGGAGAAGCGGAUCGAGA
ACCUGAACAAGAAGGUCGACGACGGCUUCCUCGACAUCUGGACGUACAACGCCGAGCUGC
UGGUGCUCCUGGAGAACGAGCGCACCCUGGACUACCACGACUCCAACGUGAAGAACCUCU
ACGAGAAGGUCCGGAGCCAGCUGAAGAACAACGCCAAGGAGAUCGGGAACGGCUGCUUCG
AGUUCUACCACAAGUGCGACAACACCUGCAUGGAGUCCGUGAAGAACGGGACCUACGACU
ACCCCAAGUACAGCGAGGAGGCCAAGCUGAACCGCGAGGAGAUCGACGGCGUGAAGCUCG
AGUCCACGCGGAUCUACCAGAUCCUGGCGAUCUACAGCACCGUCGCCAGCUCCCUGGUGC
UCGUGGUCAGCCUGGGGGCCAUCUCCUUCUGGAUGUGCAGCAACGGCUCCCUGCAGUGCC
GCAUCUGCAUCUGACCACUAGUGCAUCACAUUUAAAAGCAUCUCAGCCUACCAUGAGAAU
AAGAGAAAGAAAAUGAAGAUCAAUAGCUUAUUCAUCUCUUUUUCUUUUUCGUUGGUGUAA
AGCCAACACCCUGUCUAAAAAACAUAAAUUUCUUUAAUCAUUUGCCUCUUUUCUCUGUG
CUUCAAUUAAUAAAAAUGGAAAGAACCUAGAUCUAAAAAAAAAAAAAAAAAAAAAAAAA
AAAAAAAAAAAAAAAAAAAAAAAAAAAAAAAAAAAAAAAAAUGCAUCCCCCCCCCCCCCC
CCCCCCCCCCCCCCAAAGGCUCUUUUCAGAGCCACCAGAAUU
```

Fig. 1

METHOD FOR PRODUCING RNA COMPOSITIONS

This application is a continuation of U.S. application Ser. No. 15/566,010, filed Oct. 12, 2017, now U.S. Pat. No. 10,653,768, which is a national phase application under 35 U.S.C. § 371 of International Application No. PCT/EP2016/000607, filed Apr. 13, 2016, which claims benefit of International Application No. PCT/EP2015/000771, filed Apr. 13, 2015, the entire contents of each of which are hereby incorporated by reference.

The sequence listing that is contained in the file named "CRVCP0172USC1.txt", which is 5 KB (as measured in Microsoft Windows®) and was created on Apr. 1, 2020, is filed herewith by electronic submission and is incorporated by reference herein.

The present invention relates to a method for producing a liquid composition comprising a nanoparticle comprising at least one RNA and at least one cationic or polycationic compound, advantageously on a large scale suitable for pharmaceutical applications. The present invention further concerns the use of the inventive method in the manufacture of a medicament or a vaccine. Furthermore, the invention relates to compositions containing the RNA-comprising nanoparticle, and to pharmaceutical compositions comprising the same.

Therapeutic ribonucleic acid (RNA) molecules represent an emerging class of drugs. RNA-based therapeutics include mRNA molecules encoding antigens for use as vaccines (Fotin-Mleczek et al. 2012. J. Gene Med. 14(6):428-439). In addition, it is envisioned to use RNA molecules for replacement therapies, e.g. providing missing proteins such as growth factors or enzymes to patients (Karikó et al., 2012. Mol. Ther. 20(5):948-953; Kormann et al., 2012. Nat. Biotechnol. 29(2):154-157). Furthermore, the therapeutic use of noncoding immunostimulatory RNA molecules (cf. e.g. WO 2009/095226 A2) and other noncoding RNAs such as microRNAs and long noncoding RNAs is considered (Esteller, 2011. Nat. Rev. Genet. 12(12):861-74).

It has been found that the successful in vivo delivery of nucleic acids including RNA depends on the formulation of the active molecules into dosage forms suitable for the therapeutic application. In this context, particularly, the complexation of nucleic acids with polycatonic compounds, which results in nanoparticles, has been found to improve the in vivo delivery of nucleic acids, especially of RNA.

Different nucleic acid-comprising nanoparticles and methods for the preparation thereof have been described in the art, for example in the documents listed in the following.

WO 2010/037539 A1 describes immunostimulatory compositions comprising a) an adjuvant component, comprising or consisting of at least one (m)RNA, complexed with a cationic or polycationic compound, and b) at least one free mRNA, encoding at least one therapeutically active protein, antigen, allergen and/or antibody, wherein the immunostimulatory composition is capable to elicit or enhance an innate and optionally an adaptive immune response in a mammal.

WO 2009/144230 A1 describes protamine/RNA-comprising nanoparticles of defined average size, a pharmaceutical composition containing said nanoparticles and to a method of producing the same. The production of nanoparticles from RNA and protamine is described to comprise mixing conducted by pipette or vortexing.

WO 2012/094574 describes PEG-6-PPA/siRNA comprising nanoparticles of defined average particle size, and a pharmaceutical composition containing said nanoparticles and a method of producing the same. The production of nanoparticles from siRNA is described to comprise mixing conducted by pipette or vortexing. This document teaches that the time to allow for complexation is between 5 minutes to 60 minutes.

Yang and colleagues (Liu, Zhenzhen, et al., International journal of nanomedicine 10 (2015): 2735) describe a liquid composition comprising nanoparticles comprising siRNA and protamine. The production of nanoparticles from siRNA was conducted by vortexing of the two components (2.5 μl siRNA and protamine) and subsequent incubation for 20 minutes at room temperature.

In the above mentioned prior art, complexation of the nucleic acid (in particular of RNA) with cationic or polycationic compounds is always obtained by pipetting or vortexing. Typically, only relatively small volumes (<1 mL) are prepared on a laboratory scale by simply adding RNA to a solution of cationic or polycationic compounds (or vice versa) with subsequent mixing by repeated inversion or pipetting. Under such circumstances, it is virtually impossible to standardize the reaction conditions, which results in the variability of the physical characteristics of the produced nanoparticles. Such variability is further exacerbated by attempts to scale-up reaction volumes for pre-clinical or clinical studies, and further market delivery, where differences in physical characteristics are not acceptable. Therefore, these methods are not applicable for the large-scale production of RNA-comprising nanoparticles for medical purposes because they cannot warrant a constant process, which results in uniform batches of RNA-comprising nanoparticles.

Further methods and devices to produce nucleic acid-comprising nanoparticles are known from the prior art.

For example, a pneumatic mixing device that enables the production of large volumes of nonviral gene therapy formulations was reported (Davies et al., 2010. Biotechniques 49(3):666-668). This mixing device uses compressed air to depress the plunger of a disposable dual barrel polypropylene syringe containing plasmid DNA and lipid/polymer in separate compartments. Activation of the device initiates mixing of the components by simultaneous extrusion of the two reagents through a static mixer device.

WO 1999/040771 describes concurrent flow mixing methods and apparatuses using e.g. static or dynamic mixers that could be adapted for the preparation of gene therapy vector and vehicle compositions of controlled particle size for condensate complexes. However, actual testing was only carried out on a microliter scale WO 2009/039657 A1 describes highly concentrated chitosan-nucleic acid polyplex compositions and dispersions. Methods of mixing the chitosan-nucleic acid polyplexes include an inline mixing of chitosan solution and nucleic acid solution, followed by further concentrating the dispersion of chitosan-nucleic acid polyplexes.

A method for the preparation of siRNA-containing lipid nanoparticels by controlled microfluidic formulation was described by Chen et al., J. Am. Chem. Soc. 2012. 134(16): 6948-6951. The formulation method is based on stepwise ethanol dilution to produce siRNA lipid nanoparticles on a microliter scale.

Zhang et al. 2012 (Polydispersity characterization of lipid nanoparticles for siRNA delivery using multiple detection size-exclusion chromatography. Anal Chem. 84(14):6088-96) describe that the development of lipid nanoparticle (LNP) based small interfering RNA (siRNA) therapeutics presents unique pharmaceutical and regulatory challenges. In contrast to small molecule drugs that are highly pure and well-defined, LNP drug products can exhibit heterogeneity in size, composition, surface property, or morphology. The potential for batch heterogeneity introduces a complexity that must be addressed in order to successfully develop and ensure quality in LNP pharmaceuticals. Despite the similarity in the particle assembly process, it was found here that one LNP batch possessed a narrow particle size and molecular weight distribution while the other was polydisperse. These results suggest that LNP drug products are highly complex and diverse in nature, and care should be taken in examining and understanding them to ensure their quality and consistency. The authors concluded that currently there is a lack of scientific knowledge concerning heterogeneity of LNPs as well as high-resolution techniques that permit its evaluation.

In summary, all conventional bulk techniques for the preparation of nucleic acid (RNA) formulations, such as RNA-comprising nanoparticles, which involve uncontrolled mixing of the compound solution and the RNA solution (or vice versa), may face limitations including poor reproducibility, polydisperse particle size distribution and batch-to-batch variation with respect to physicochemical properties of the nanoparticle, especially when performed at a large scale. Moreover, as RNA therapeutics are applied for various different indications, different batch sizes are needed and thus, flexibly scalable methods for the preparation of RNA-comprising nanoparticle formulations are sought-after.

In view of the above-mentioned prior art, there is a continued need for improved, economical and flexibly scalable means and methods of producing RNA-comprising nanoparticles, especially for the large scale preparation of RNA therapeutics. Particularly, there is a need to produce uniform large-scale batches of RNA-comprising nanoparticles having similar average particles sizes and polydispersity. Especially, for pre-clinical and clinical studies, and eventually the market delivery of a medicament based on a RNA-comprising compound and/or nanoparticles, a production method is required to allow a reproducible production of RNA-comprising compound and/or nanoparticles, which are to be obtained with a reliable quality (i.e. constant physical characteristics) in the large scale production thereof.

In view of the above-discussed problem, the inventors of the present invention conducted intensive studies with regard to up-scaling of the production of RNA-comprising nanoparticles suitable for pharmaceutical applications, especially RNA-comprising nanoparticles, which are characterised by having uniform average particles sizes and polydispersity. The inventors have surprisingly found that, independent of reagents and scale, a reliable production of a uniform RNA-comprising compound can be obtained in a reproducible manner, if the compound-forming reaction is conducted using a reactor with a blend time of 5 seconds or less. More preferably, the blend time is 2.5 seconds or less, 2.0 seconds or less, 1.0 seconds or less, or 0.5 seconds or less. Alternatively, the blend time is preferably in a range from about 0.001 seconds to about 5 seconds, more preferably from about 0.01 seconds to about 5 seconds, even more preferably from about 0.1 seconds to about 5 seconds and most preferably from about 0.001 to about 2 seconds or from about 0.01 to about 2 seconds.

In light of the above described prior art, the inventors unexpectedly found that decreasing the blend time of the compound-forming reaction increases the homogeneity of the compound-containing mixture and also increases the uniformity of the nanoparticles.

Moreover, the inventors have surprisingly found that the so-obtained compositions comprising RNA-comprising compounds exhibit a very high quality of uniform RNA-comprising compound in high yields, without comprising significant amounts of unwanted side products, which usually lead to problems concerning the stability and/or applicability of the product compositions. In particular, a liquid composition can be obtained by the method according to the present invention, wherein RNA is present in a complex with a cationic or polycationic compound, while no undesired precipitates or aggregates are formed.

On basis of these findings, the inventors have completed the present invention, which provides a reliable method for producing a RNA-comprising nanoparticle in a quality sufficient and reliable for pharmaceutical applications, even in a large scale production. Further, the invention provides a production process both cost-effective and reliable on a large scale. The present invention was made with support from the Government under Agreement No. HR0011-11-3-0001 awarded by DARPA. The Government has certain rights in the invention.

In particular, the present invention provides a method for producing a liquid composition comprising a nanoparticle comprising at least one RNA and at least one cationic or polycationic compound,
wherein the method comprises the steps of:
(a) providing a first liquid composition comprising at least one RNA,
(b) providing a second liquid composition comprising at least one cationic or polycationic compound,
(c) introducing the first liquid composition and the second liquid composition into at least one reactor, wherein the at least one RNA and the at least one cationic or polycationic compound are mixed with a blend time of 5 seconds or less and reacted with each other, and
(d) recovering the product liquid composition comprising the nanoparticle comprising the at least one RNA and the at least one cationic or polycationic compound from the reactor.

It was found that the method according to the present invention produces a nanoparticle comprising at least one RNA and at least one cationic or polycationic compound, reliably under controlled conditions, without allowing unwanted side reactions resulting in unwanted side products and stability and/or applicability problems caused thereby, independent of the scale of production. Further, the method according to the present invention is both cost-effective and reliable, even on a large scale, which renders the method of the invention especially suitable for the pharmaceutical production of RNA-comprising nanoparticles. Preferably and advantageously, the method according to the invention is used for the production of a nanoparticle comprising at least one RNA and at least one cationic or polycationic compound on a large scale, preferably an industrial scale of pharmaceutical production.

In the context of the invention, the term "large scale" (sometimes "large scale batch") refers to an amount of RNA-comprising compound, which summarily comprises RNA in an amount of 1 g or more, preferably in an amount of 5 g and more, and even more preferred in an amount of 10 g or more.

In the following description of the present invention and its preferred embodiments, if not otherwise indicated, different features of alternatives and embodiments may be combined with each other, where suitable. Furthermore, the term "comprising" shall not be construed as meaning "consisting of", if not specifically mentioned. However, in the context of the present invention, term "comprising" may be substituted with the term "consisting of", where suitable.

In the context of the invention, the term RNA is used to indicate any type of ribonucleic acid.

Examples of RNA, which can be used in the method of the present invention are disclosed, e.g. in WO 2008/077592 A1, WO 2009/095226 A2, WO 2010/037539 and WO 2011/026641 A1, which are all incorporated herein by reference.

Preferably, the at least one RNA is selected from the group consisting of a long-chain RNA, a coding RNA, a non-coding RNA, a messenger RNA (mRNA), an RNA oligonucleotide, an siRNA, an shRNA, an antisense RNA, a riboswitch, an immunostimulating RNA (isRNA), a ribozyme or an aptamer; etc. The RNA may also be a ribosomal RNA (rRNA), a transfer RNA (tRNA), a messenger RNA (mRNA), a viral RNA (vRNA) or a replicon RNA. Preferably, the RNA is a coding RNA. Even more preferably, the RNA is a (linear) single-stranded RNA, even more preferably an mRNA.

Alternatively, the at least one RNA may be selected from the group consisting of a long-chain RNA, a coding RNA, a non-coding RNA, a single stranded RNA (ssRNA), a double stranded RNA (dsRNA), a linear RNA (linRNA), a circular RNA (circRNA), a messenger RNA (mRNA), an RNA oligonucleotide, a small interfering RNA (siRNA), a small hairpin RNA (shRNA), an antisense RNA (asRNA), a CRISPR/Cas9 guide RNA, a riboswitch, an immunostimulating RNA (isRNA), a ribozyme or an aptamer; etc. The RNA may also be a ribosomal RNA (rRNA), a transfer RNA (tRNA), a messenger RNA (mRNA), a viral RNA (vRNA), a retroviral RNA, or a replicon RNA, a small nuclear RNA (snRNA), a small nucleolar RNA (snoRNA), a microRNA (miRNA), and a Piwi-interacting RNA (piRNA). Preferably, the RNA is a coding RNA.

In the context of the present invention, an mRNA is typically an RNA, which is composed of several structural elements, e.g. an optional 5'-UTR region, an upstream positioned ribosomal binding site followed by a coding region, an optional 3'-UTR region, which may be followed by a poly-A tail (and/or a poly-C-tail). An mRNA may occur as a mono-, di-, or even multicistronic RNA, i.e. an RNA which carries the coding sequences of one, two or more (identical or different) proteins or peptides as defined herein. Such coding sequences in di-, or even multicistronic mRNA may be separated by at least one IRES (internal ribosomal entry site) sequence.

Furthermore, the at least one RNA may be a single- or a double-stranded RNA (molecule) or a partially double-stranded or partially single stranded RNA, which are at least partially self complementary (both of these partially double-stranded or partially single stranded RNA molecules are typically formed by a longer and a shorter single-stranded RNA molecule or by two single stranded RNA molecules, which are about equal in length, wherein one single-stranded RNA molecule is in part complementary to the other single-stranded RNA molecule and both thus form a double-stranded nucleic RNA in this region, i.e. a partially double-stranded or partially single stranded RNA (molecule). Preferably, the at least one RNA is a single-stranded RNA molecule. Furthermore, the RNA (molecule) may be a circular or linear RNA molecule, preferably a linear RNA molecule.

Coding RNA:

The at least one RNA may encode a protein or a peptide, which may be selected, without being restricted thereto, e.g. from therapeutically active proteins or peptides, selected e,g, from adjuvant proteins, from antigens, e.g. tumour antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, or from any other protein or peptide suitable for a specific (therapeutic) application, wherein the coding RNA may be transported into a cell, a tissue or an organism and the protein may be expressed subsequently in this cell, tissue or organism.

The coding region of the at least one RNA may occur as a mono-, di-, or even multicistronic RNA, i.e. an RNA, which carries the coding sequences of one, two or more proteins or peptides. Such coding sequences in di-, or even multicistronic RNA may be separated by at least one internal ribosome entry site (IRES) sequence, or by signal peptides which induce the cleavage of the resulting polypeptide, which comprises several proteins or peptides.

In particular preferred embodiments, the encoded peptides or proteins are selected from human, viral, bacterial, protozoan proteins or peptides.

a) Therapeutically Active Proteins

In the context of the present invention, therapeutically active proteins or peptides may be encoded by the at least one RNA. Therapeutically active proteins are defined herein as proteins, which have an effect on healing, prevent prophylactically or treat therapeutically a disease, preferably as defined herein, or are proteins of which an individual is in need of. These may be selected from any naturally or synthetically designed occurring recombinant or isolated protein known to a skilled person from the prior art. Without being restricted thereto therapeutically active proteins may comprise proteins, capable of stimulating or inhibiting the signal transduction in the cell, e.g. cytokines, lymphokines, monokines, growth factors, receptors, signal transduction molecules, transcription factors, etc; anticoagulants; antithrombins; antiallergic proteins; apoptotic factors or apoptosis related proteins, therapeutic active enzymes and any protein connected with any acquired disease or any hereditary disease.

A therapeutically active protein, which may be encoded by the RNA, may also be an adjuvant protein. In this context, an adjuvant protein is preferably to be understood as any protein, which is capable to elicit an innate immune response as defined herein. Preferably, such an innate immune response comprises activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. More preferably, the adjuvant protein is selected from human adjuvant proteins or from pathogenic adjuvant proteins, selected from the group consisting of, without being limited thereto, bacterial proteins, protozoan proteins, viral proteins, or fungal proteins, animal proteins, in particular from bacterial adjuvant proteins. In addition, RNA encoding human proteins involved in adjuvant effects (e.g. ligands of pattern recognition receptors, pattern recoginition receptors, proteins of the signal transduction pathways, transcription factors or cytokines) may be used as well.

b) Antigens

The at least one RNA may alternatively encode an antigen. According to the present invention, the term "antigen" refers to a substance, which is recognized by the immune system and is capable of triggering an antigen-specific immune response, e.g. by formation of antibodies or antigen-specific T-cells as part of an adaptive immune response. In this context an antigenic epitope, fragment or peptide of a protein means particularly B cell and T cell epitopes, which may be recognized by B cells, antibodies or T cells respectively.

In the context of the present invention, antigens as encoded by the at least one RNA typically comprise any antigen, antigenic epitope or antigenic peptide, falling under the above definition, more preferably protein and peptide antigens, e.g. tumour antigens, allergenic antigens, auto-immune self-antigens, pathogenic antigens, etc. In particular antigens as encoded by the RNA may be antigens generated outside the cell, more typically antigens not derived from the host organism (e.g. a human) itself (i.e. non-self antigens) but rather derived from host cells outside the host organism, e.g. viral antigens, bacterial antigens, fungal antigens, protozoological antigens, animal antigens, allergenic antigens, etc. Allergenic antigens (allergy antigens) are typically antigens, which cause an allergy in a human and may be derived from either a human or other sources. Additionally, antigens as encoded by the RNA may be furthermore antigens generated inside the cell, the tissue or the body. Such antigens include antigens derived from the host organism (e.g. a human) itself, e.g. tumour antigens, self-antigens or auto-antigens, such as auto-immune self-antigens, etc., but also (non-self) antigens as defined herein, which have been originally been derived from host cells outside the host organism, but which are fragmented or degraded inside the body, tissue or cell, e.g. by (protease) degradation, metabolism, etc.

One class of antigens as encoded by the RNA comprises tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells, which are (were) not themselves (or originally not themselves) degenerated but are associated with the supposed tumour. Antigens, which are connected with tumour-supplying vessels or (re)formation thereof, in particular those antigens, which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies.

According to another alternative, one further class of antigens as encoded by the RNA comprises allergenic antigens. Such allergenic antigens may be selected from antigens derived from different sources, e.g. from animals, plants, fungi, bacteria, etc. Allergens in this context include e.g. grasses, pollens, molds, drugs, or numerous environmental triggers, etc.

c) Antibodies

According to a further alternative, the RNA may encode an antibody or an antibody fragment. According to the present invention, such an antibody may be selected from any antibody, e.g. any recombinantly produced or naturally occurring antibodies, known in the art, in particular antibodies suitable for therapeutic, diagnostic or scientific purposes, or antibodies, which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, the term "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$.

In the context of the present invention, antibodies as encoded by the at least one RNA may preferably comprise full-length antibodies, i.e. antibodies composed of the full heavy and full light chains, as described above. However, derivatives of antibodies such as antibody fragments, variants or adducts may also be encoded by the RNA. Antibody fragments are preferably selected from Fab, Fab', F(ab')$_2$, Fc, Facb, pFc', Fd and Fv fragments of the aforementioned (full-length) antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

In the present context, it is preferable that the different chains of the antibody or antibody fragment are encoded by a multicistronic RNA. Alternatively, the different strains of the antibody or antibody fragment are encoded by several monocistronic RNA (sequences).

siRNA:

According to a further alternative, the at least one RNA may be in the form of dsRNA, preferably siRNA. A dsRNA, or a siRNA, is of interest particularly in connection with the phenomenon of RNA interference. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498).

The RNA may thus be a double-stranded RNA (dsRNA) having a length of from 17 to 29, preferably from 19 to 25, and preferably being at least 90%, more preferably 95% and especially 100% (of the nucleotides of a dsRNA) complementary to a section of the RNA sequence of a (therapeutically relevant) protein or antigen described (as active ingredient) hereinbefore, either a coding or a non-coding section, preferably a coding section. 90% complementary means that with a length of a dsRNA described herein of, for example, 20 nucleotides, this contains not more than 2 nucleotides without corresponding complementarity with the corresponding section of the mRNA. The sequence of the double-stranded RNA is, however, preferably wholly complementary in its general structure with a section of the RNA of a therapeutically relevant protein or antigen described hereinbefore. In this context the RNA may be a dsRNA having the general structure 5'-($N_{17-23}$)-3', preferably having the general structure 5'-($N_{13-25}$)-3', more preferably having the general structure 5'-($N_{1-24}$)-3', or yet more preferably having the general structure 5'-($N_{21-23}$)-3', wherein for each general structure each N is a (preferably different) nucleotide of a section of the mRNA of a therapeutically relevant protein or antigen described hereinbefore, preferably being selected from a continuous number of 17 to 29 nucleotides of the mRNA of a therapeutically relevant protein or antigen and being present in the general structure 5'-($N_{17-23}$)-3' in their natural order. In principle, all the sections having a length of from 17 to 29, preferably from 19 to 25, base pairs that occur in the coding region of the mRNA can serve as target sequence for a dsRNA herein. Equally, dsRNAs used as RNA can also be directed against nucleotide sequences of a (therapeutically relevant) protein or antigen described (as active ingredient) hereinbefore that do not lie in the coding region, in particular in the 5' non-coding region of the mRNA, for example, therefore, against non-coding regions of the mRNA having a regulatory function. The target sequence of the dsRNA used as RNA can therefore lie in the translated and untranslated region of the mRNA and/or in the region of the control elements of a protein or antigen described hereinbefore. The target sequence of a dsRNA used as RNA can also lie in the overlapping region of untranslated and translated sequence; in particular, the target sequence can comprise at least one nucleotide upstream of the start triplet of the coding region of the mRNA.

Immunostimulatory RNA:

a) Immunostimulatory CpG Nucleic Acids:

According to another alternative, the at least one RNA may be in the form of a(n) (immunostimulatory) CpG-RNA, which preferably induces an innate immune response. A CpG-RNA can be a single-stranded CpG-RNA (ss CpG-RNA) or a double-stranded CpG-RNA (ds CpG-RNA). The CpG-RNA is preferably in the form of single-stranded CpG-RNA (ss CpG-RNA). Also preferably, such CpG RNA have a length as described above. Preferably, the CpG motifs are unmethylated.

b) Immunostimulatory RNA (isRNA):

Likewise, according to a further alternative, the at least one RNA may be in the form of an immunostimulatory RNA (isRNA), which preferably elicits an innate immune response. Such an immunostimulatory RNA may be any (double-stranded or single-stranded) RNA, e.g. a coding RNA, as defined herein. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response, may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc NatlAcadSci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The immunostimulatory RNA (isRNA) may thus comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Furthermore, (classes of) immunostimulatory RNA molecules may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment of the present invention, such immunostimulatory RNA consist of or comprise an RNA of formula (I) or (II):

$$G_l X_m G_n \quad \text{(formula (I))},$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
  wherein
  when l=1 G is guanosine or an analogue thereof,
  when l>1 at least 50% of the nucleotides are guanosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 G is guanosine or an analogue thereof,
  when n>1 at least 50% of the nucleotides are guanosine or an analogue thereof.

$$C_l X_m C_n \quad \text{(formula (II))},$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
  wherein
  when l=1 C is cytosine or an analogue thereof,
  when l>1 at least 50% of the nucleotides are cytosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 C is cytosine or an analogue thereof,
  when n>1 at least 50% of the nucleotides are cytosine or an analogue thereof.

The RNA of formula (I) or (II) may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the RNA has a maximum length of e.g. 100 nucleotides, m will typically be <=98. The number of nucleotides G in the RNA of formula (I) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. A nucleotide adjacent to X, in the RNA of formula (II) according to the invention is preferably not a uracil. Preferably, for formula (I), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_1$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (IV).

According to a further particularly preferred embodiment, such immunostimulatory RNA, consists of or comprises an RNA of formula (III) or (IV):

$$(N_u G_l X_m G_n N_v)_a \quad \text{(formula (III))},$$

wherein:
G is guanosine (guanine), uridine (uracil) or an analogue of guanosine (guanine) or uridine (uracil), preferably guanosine (guanine) or an analogue thereof;
X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, G is guanosine (guanine) or an analogue thereof,
    when l>1, at least 50% of these nucleotides (nucleosides) are guanosine (guanine) or an analogue thereof;
m is an integer and is at least 3;
  wherein when m=3, X is uridine (uracil) or an analogue thereof, and
    when m>3, at least 3 successive uridines (uracils) or analogues of uridine (uracil) occur;
n is an integer from 1 to 40,
  wherein when n=1, G is guanosine (guanine) or an analogue thereof,
    when n>1, at least 50% of these nucleotides (nucleosides) are guanosine (guanine) or an analogue thereof;
u,v may be independently from each other an integer from 0 to 50,
  preferably wherein when u=0, v≥1, or
    when v=0, u≥1;
wherein the RNA molecule of formula (III) has a length of at least 50 nucleotides, preferably of at least 100 nucleotides, more preferably of at least 150 nucleotides, even more preferably of at least 200 nucleotides and most preferably of at least 250 nucleotides.

 (formula (IV)), wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, C is cytidine (cytosine) or an analogue thereof,
    when l>1, at least 50% of these nucleotides (nucleosides) are cytidine (cytosine) or an analogue thereof;
m is an integer and is at least 3;
  wherein when m=3, X is uridine (uracil) or an analogue thereof,
    when m>3, at least 3 successive uridines (uracils) or analogues of uridine (uracil) occur;
n is an integer from 1 to 40,
  wherein when n=1, C is cytidine (cytosine) or an analogue thereof,
    when n>1, at least 50% of these nucleotides (nucleosides) are cytidine (cytosine) or an analogue thereof.
u, v may be independently from each other an integer from 0 to 50,
  preferably wherein when u=0, v≥1, or
    when v=0, u≥1;
wherein the RNA molecule of formula (IV) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (IV), any of the definitions given above for elements N (i.e. $N_u$ and $N_v$) and X ($X_m$), particularly the core structure as defined above, as well as for integers a, l, m, n, u and v, similarly apply to elements of formula (III) correspondingly, wherein in formula (IV) the core structure is defined by $C_l X_m C_n$. The definition of bordering elements $N_u$ and $N_v$ is identical to the definitions given above for $N_u$ and $N_v$.

In a further preferred embodiment the at least one RNA may also occur in the form of a modified RNA.

According to a further embodiment, the RNA may be provided as a "stabilized RNA", preferably as a RNA that is essentially resistant to in vivo degradation (e.g. by an exo- or endo-nuclease).

In the context of the present invention, a 'modified RNA' is an RNA molecule comprising at least one modification, preferably as defined herein. In a preferred embodiment, the at least one RNA as used herein comprises at least one modification as described herein. Preferably, the at least one RNA comprises an RNA modification, which preferably increases the stability of the RNA molecule and/or the expression of a protein encoded by the RNA. Several RNA modifications are known in the art, which can be applied to an RNA molecule in the context of the present invention.

Chemical Modifications:

The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Sugar Modifications:

The modified nucleosides and nucleotides, which may be incorporated into a RNA molecule as described herein, can be modified in the sugar moiety. For example, the 2' hydroxyl group (OH) can be modified or replaced with a number of different "oxy" or "deoxy" substituents.

Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA molecule can include nucleotides containing, for instance, arabinose as the sugar.

Backbone Modifications:

The phosphate backbone may further be modified in the modified nucleosides and nucleotides, which may be incorporated into a modified RNA molecule as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into a modified RNA molecule as described herein can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azau ridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 06-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-l-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments, a modified RNA may comprise nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Lipid Modification:

According to a further embodiment, a modified RNA molecule as defined herein can contain a lipid modification. Such a lipid-modified RNA molecule typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an RNA molecule as defined herein, at least one linker covalently linked with that RNA molecule, and at least one lipid covalently linked with the respective linker, and also at least one (bifunctional) lipid covalently linked (without a linker) with that RNA molecule. In this context, it is particularly preferred that the lipid modification is present at the terminal ends of a linear RNA sequence.

Modification of the 5'-End:

According to another preferred embodiment of the invention, a modified RNA molecule as defined herein, can be modified by the addition of a so-called "5' CAP" structure.

A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in a modified RNA in this context.

Accordingly, a modified RNA of the present invention may comprise a m7GpppN as 5'-CAP, but additionally the modified RNA comprises at least one further modification as defined herein.

Further examples of 5'-cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures are regarded as at least one modification in this context.

Particularly preferred modified 5'-CAP structures are CAP1 (methylation of the ribose of the adjacent nucleotide of m7G), CAP2 (methylation of the ribose of the 2nd nucleotide downstream of the m7G), CAP3 (methylation of the ribose of the 3rd nucleotide downstream of the m7G), CAP4 (methylation of the ribose of the 4th nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Sequence Modifications:

In a preferred embodiment, the at least one RNA comprises or consists of a modified RNA molecule having at least one open reading frame, which encodes at least one peptide or protein. Preferably, the sequence of the open reading frame in such an RNA molecule is modified as described herein. Such an RNA comprising a modified sequence of the open reading frame is also included in the term "modified RNA".

Modification of the G/C Content:

In a particularly preferred embodiment of the present invention, the G/C content of the coding region of an RNA is modified, particularly increased, compared to the G/C content of its particular wild type coding region, i.e. the unmodified coding region. The encoded amino acid sequence of the coding region is preferably not modified compared to the coded amino acid sequence of the particular wild type coding region. The modification of the G/C-content of the coding region of the modified RNA as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Depending on the amino acid to be encoded by the coding region of the modified RNA as defined herein, there are various possibilities for modification of the RNA sequence, e.g. the coding region, compared to its wild type coding region. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons which contain A and/or U nucleotides can be modified by substitution of other codons which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons, which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gln can be modified from CAA to CAG; the codons for Ile can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in any possible combination to increase the G/C content of the coding region of the RNA as defined herein, compared to its particular wild type coding region (i.e. the original sequence). Thus, for example, all codons for Thr occurring in the wild type sequence can be modified to ACC (or ACG).

Preferably, the G/C content of the coding region of the RNA as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein, are substituted, thereby increasing the G/C content of said coding region. In this context, it is particularly preferable to increase the G/C content of the coding region of the modified RNA as defined herein, to the maximum (i.e. 100% of the substitutable codons), compared to the wild type coding region.

Codon Optimization:

According to the invention, a further preferred modification of the coding region encoding at least one peptide or protein of a modified RNA as defined herein, is based on the finding that the translation efficiency is also determined by a different frequency in the occurrence of tRNAs in cells. Thus, if so-called "rare codons" are present in the coding region of the wild type RNA sequence, to an increased extent, the mRNA is translated to a significantly poorer degree than in the case, where codons coding for relatively "frequent" tRNAs are present. In this context, the coding region of the at least one RNA is preferably modified compared to the corresponding wild type coding region such that at least one codon of the wild type sequence, which codes for a tRNA which is relatively rare in the cell, is exchanged for a codon, which codes for a tRNA which is relatively frequent in the cell and carries the same amino acid as the relatively rare tRNA. By this modification, the coding region of the at least one RNA as defined herein, is modified such that codons, for which frequently occurring tRNAs are available, are inserted. In other words, according to the invention, by this modification all codons of the wild type coding region, which code for a tRNA, which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content, which is increased, in particular maximized, in the coding region of the modified RNA as defined herein, with the "frequent" codons without modifying the amino acid sequence of the peptide or protein encoded by the coding region of the RNA sequence. This preferred embodiment allows provision of a particularly efficiently translated and stabilized (modified) RNA sequence as defined herein.

In the context of the present invention, the at least one RNA may also comprise a 5'- and/or 3' untranslated region (5'-UTR or 3'-UTR, respectively). More preferably, the at least one RNA comprises a 5'-CAP structure as defined above.

Preferably, the at least one RNA further comprises a poly(A) sequence. The length of the poly(A) sequence may vary. For example, the poly(A) sequence may have a length of about 20 adenine nucleotides up to about 300 adenine nucleotides, preferably of about 40 to about 200 adenine nucleotides, more preferably from about 50 to about 100 adenine nucleotides, such as about 60, 70, 80, 90 or 100 adenine nucleotides. Most preferably, the at least one RNA comprises a poly(A) sequence of about 60 to about 70 nucleotides, most preferably 64 adenine nucleotides.

Preferably, the poly(A) sequence in the at least one RNA is derived from a DNA template by in vitro transcription. Alternatively, the poly(A) sequence may also be obtained in vitro by common methods of chemical-synthesis without being necessarily transcribed from a DNA-progenitor or may be obtained by enzymatic polyadenylation using a poly(A) polymerase e.g. *E. coli* poly(A) polymerase.

In addition or as an alternative to a poly(A) sequence as described above, the at least one RNA may also comprise a poly(C) sequence, preferably in the region 3' of the coding region of the RNA. A poly(C) sequence is typically a stretch of multiple cytosine nucleotides, typically about 10 to about 200 cytidine nucleotides, preferably about 10 to about 100 cytidine nucleotides, more preferably about 10 to about 70 cytidine nucleotides or even more preferably about 20 to about 50 or even about 20 to about 30 cytidine nucleotides. A poly(C) sequence may preferably be located 3' of the coding region comprised by a nucleic acid. In a preferred embodiment of the present invention, the at least one RNA comprises a poly(A) sequence and a poly(C) sequence, wherein the poly(C) sequence is located 3' of the poly(A) sequence.

In a particularly preferred embodiment, the at least one RNA in the context of the present invention comprises in 5'-to-3'-direction, optionally a 5'-UTR, an open reading frame, preferably a modified open reading frame as defined herein, a 3'-UTR element, a poly(A) and/or a poly(C) sequence and optionally a histone stem-loop. Preferred 5'-UTR's are described in WO 2013/143699 and WO 2013/

143700, the disclosure of which is herewith incorporated by reference. 3'-UTR sequences, which are preferred in this context, are described in WO 2013/143698. Examples of preferred histone stem-loop sequences are described in WO 2012/019780, whose disclosure is incorporated herewith by reference.

Preferably, the at least one RNA as used herein comprises more than 30 nucleotides. More preferably, the at least one RNA is not selected from siRNA, small hairpin RNA, microRNA or small nuclear RNA (snRNA). In a particularly preferred embodiment, the at least one RNA as used herein is not an siRNA.

Preferably, the at least one RNA is a long-chain RNA. The term 'long-chain RNA' as used herein herein typically refers to an RNA molecule, preferably as described herein, which preferably comprises at least 30 nucleotides. Alternatively, a long-chain RNA may comprise at least 35, 40, 45, 50, 55, 60, 65, 70, 75, 80, 85, 90, 95, 100, 150, 200, 250, 300, 350, 400, 450 or at least 500 nucleotides. A long-chain RNA molecule may further comprise at least 100 nucleotides, even more preferably at least 200 nucleotides. A long-chain RNA, in the context of the present invention, further preferably comprises from 30 to 50.000 nucleotides, from 30 to 20.000 nucleotides, from 100 to 20.000 nucleotides, from 200 to 20.000 nucleotides, from 200 to 15.000 nucleotides or from 500 to 20.000 nucleotides. The term long-chain RNA' as used herein is not limited to a certain type of RNA, but merely refers to the number of nucleotides comprised in said RNA. In a preferred embodiment, the at least one RNA as used herein is a long-chain mRNA.

According to the invention, the method comprises a step a), which comprises providing a first liquid composition comprising at least one RNA.

In this context, the first liquid composition may comprise exactly one (type of) RNA molecule, or a mixture of two or more different (types of) RNA molecules, such as, for example, two, three, four, five, six etc. different (types of) RNA molecules, wherein a plurality of each (type of) RNA molecule is preferably present in the first liquid composition. Preferably, the first liquid composition comprises from 1 to 20 different RNA molecules, further preferred from 1 to 10 different RNA molecules, further preferred from 1 to 6, and still further preferred 1, 2, 3, 4, 5 or 6 different RNA molecules. In a preferred embodiment, the first liquid solution comprises more than one RNA, wherein the RNA molecules differ in their respective coding regions and, optionally, further structural elements. Preferably, the first liquid composition comprises 1, 2, 3, 4, 5, 6, 7, 8, 9 or 10 different RNA molecules, each of which encodes a distinct peptide or protein preferably an antigen. Especially preferably, the first liquid composition comprises one RNA.

Preferably, the first liquid composition comprises water as a solvent. Additionally, the first liquid composition may comprise at least one solvent miscible with water. Examples of such water-miscible solvents are known in the art. Preferred examples of additional solvents are alcohols, such as, e.g. ethanol, etc., DMSO, and the like. Especially preferred, the additional solvent is pharmaceutically acceptable. Examples of pharmaceutically acceptable solvents are, e.g. ethanol, etc.

Preferably, the first liquid composition is an aqueous solution of RNA and, optionally, at least one further component. In a preferred embodiment, the at least one RNA is present in the first liquid composition in its free form, i.e. as 'naked' RNA.

Preferably, the first liquid composition comprises RNA in a concentration of from 0.1 to 20 g/L, preferably from 0.5 to 10 g/L, more preferably from 0.5 to 7 g/L, more preferably of from 0.5 to 2 g/L and most preferably of from 0.5 to 1.0 g/L. More preferably, the first liquid composition comprises the at least one RNA as defined herein in a concentration as defined above.

The inventive method further comprises a step b) of providing a second liquid composition comprising at least one cationic or polycationic compound.

In the context of the invention, the term 'cationic or polycationic compound' is used for a compound, preferably an oligomeric or polymeric compound, comprising one to numerous cationic functions (i.e. positive charges). Such compounds are known in the art, where they are sometimes also referred to as "polycationic molecules" or "polycationic polymers". Examples of cationic or polycationic compounds comprise cationic or polycationic peptides or polypeptides, cationic or polycationic proteins, cationic or polycationic polyamino acids, cationic or polycationic carbohydrates, cationic or polycationic synthetic polymers, cationic or polycationic small synthetic organic molecules, inorganic multivalent cations, cationic lipids, and the like.

Preferred examples of cationic or polycationic compounds which can be used in the method of the present invention are disclosed, e.g. in WO 2008/077592 A1, WO 2009/095226 A2, WO 2010/037539 and WO 2011/026641 A1, which are all incorporated herein by reference.

The second liquid composition provided in step b) comprises at least one cationic or polycationic compound, wherein the at least one cationic or polycationic compound is preferably capable of forming a complex with the at least one RNA comprised in the first liquid composition provided in step a) of the inventive method. More preferably, the at least one cationic or polycationic compound comprised in the second liquid composition forms a nanoparticle with the at least one RNA comprised in the first liquid composition, wherein the composition, optionally comprises at least one further component, such as, for instance, a lyoprotectant, preferably as defined herein.

Alternatively or in addition to a cationic or polycationic compound, the at least one RNA may also be complexed by a compound selected from the group of polymers or complexing agents, typically comprising, without being limited thereto, any polymer suitable for the preparation of a pharmaceutical composition, such as minor/major groove binders, nucleic acid binding proteins, lipoplexes, nanoplexes, non-cationic or non-polycationic compounds, such as PLGA, Polyacetate, Polyacrylate, PVA, Dextran, hydroxymethylcellulose, starch, MMP, PVP, heparin, pectin, hyaluronic acid, and derivatives thereof. In a further preferred embodiment, the at least one RNA may also be complexed—alternatively or in addition to a cationic or polycationic compound—by a compound selected from the group of polymers or complexing agents, typically comprising, without being limited thereto, any polymer suitable for the preparation of a pharmaceutical composition, such as minor/major groove binders, nucleic acid binding proteins, lipids, lipoplexes, nanoplexes, non-cationic or non-polycationic compounds, such as PLGA, Polyacetate, Polyacrylate, PVA, Dextran, hydroxymethylcellulose, starch, MMP, PVP, heparin, pectin, hyaluronic acid, and derivatives thereof.

Preferably, the second liquid composition comprises water as a solvent. Additionally, the second liquid composition may comprise one or more of solvent miscible with water. Examples of such water-miscible solvents are known in the art. Preferred examples of additional solvents are alcohols, such as, e.g. ethanol, etc., DMSO, and the like. Especially preferred, the additional solvent is pharmaceutically acceptable. Examples of pharmaceutically acceptable solvents are, e.g. ethanol, etc.

Preferably, the second liquid composition is an aequeous solution of the at least one cationic or polycationic compound, which optionally comprises at least one further component, wherein the at least one further compound is preferably a lyoprotectant as defined herein.

Preferably, the second liquid composition comprises a cationic or polycationic compound in a concentration of from 0.05 to 10.00 g/L, preferably of from 0.10 to 5.00 g/L, more preferably of from 0.10 to 1.0 g/L and most preferably of from 0.1 to 0.5 g/L.

In a preferred example, the second liquid composition comprises protamine in a concentration of from 0.1 to 1 g/L, more preferably in a concentration of 0.3 to 0.6 g/L or in a concentration of from 0.4 to 0.5 g/L and most preferably in a concentration of from 0.4 to 0.5 g/L and even more preferably in a concentration of from 0.3 to 0.45 g/L.

Preferably, the concentration of cationic or polycationic compound in the second liquid composition is adjusted to provide a predetermined ratio with respect to the concentration of RNA in the first liquid composition.

Preferably, the concentration of cationic or polycationic compound is adjusted to the concentration of the RNA so as to provide an N/P-ratio of about 0.1-10, preferably in a range of about 0.3-4 and most preferably in a range of about 0.5-2 or 0.7-2 regarding the ratio of mRNA:cationic or polycationic compound and/or polymeric carrier, preferably as defined herein, in the complex, and most preferably in a range of about 0.7-1.5, 0.5-1 or 0.7-1, and even most preferably in a range of about 0.3-0.9 or 0.5-0.9. In this context, the N/P-ratio is defined as the ratio of the number of cationic nitrogen functions of the cationic or polycationic compound (N) to the number of phosphate residues of the RNA (P). It may be calculated on the basis that, for example, 1 µg RNA typically contains about 3 nmol phosphate residues, provided that the RNA exhibits a statistical distribution of bases.

The concentration of a cationic or polycationic compound, preferably protamine, in the second liquid composition is preferably such that the weight ratio of the cationic or polycationic compound, preferably protamine, and the at least one RNA are present in the mixture of the first and the second liquid composition, which is obtained in step c) of the inventive method, at a weight ratio (RNA:cationic or polycationic compound, w/w) in a range from 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Most preferably, the weight ratio of the at least one RNA to the at least one cationic or polycationic compound, preferably protamine, in the mixture obtained in step c) is 2:1 (w/w).

According to the invention, the at least one cationic or polycationic compound in the second liquid composition may be a cationic or polycationic peptide or protein, which optionally comprises or is additionally modified to comprise at least one —SH moiety. Preferably, the at least one cationic or polycationic compound is selected from cationic peptides having the following sum formula (V):

{(Arg)$_l$;(Lys)$_m$;(His)$_n$;(Orn)$_o$;(Xaa)$_x$} (SEQ ID NO: 2); formula (V)

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context, cationic peptides or proteins in the range of 7-30 amino acids are particular preferred.

Further, the cationic or polycationic peptide or protein, when defined according to formula {(Arg)$_l$;(Lys)$_m$;(His)$_n$;(Orn)$_o$;(Xaa)$_x$} (formula (V)) as shown above and which comprises or is additionally modified to comprise at least one —SH moeity, may be, without being restricted thereto, selected from subformula (Va):

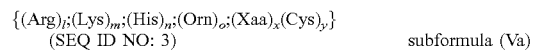
(SEQ ID NO: 3) subformula (Va)

wherein (Arg)$_l$;(Lys)$_m$;(His)$_n$;(Orn)$_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (Vb):

Cys$_1${(Arg)$_l$;(Lys)$_m$;(His)$_n$;(Orn)$_o$;(Xaa)$_x$}Cys2
(SEQ ID NO: 4) subformula (Vb)

wherein empirical formula {(Arg)$_l$;(Lys)$_m$;(His)$_n$;(Orn)$_o$;(Xaa)$_x$} (formula (V)) is as defined herein and wherein Cys, and Cys2 are Cysteines proximal to, or terminal to (Arg)$_l$;(Lys)$_m$;(His)$_n$;(Orn)$_o$;(Xaa)$_x$.

In the context of the inventive method, particularly preferred cationic or polycationic compounds include protamine, nucleoline, spermine or spermidine, or other cationic peptides or proteins, such as poly-L-lysine (PLL), poly-arginine, oligoarginines as defined herein, such as Arg$_7$, Arg$_8$, Arg$_9$, Arg$_7$, H$_3$R$_9$, R$_9$H$_3$, H$_3$R$_9$H$_3$, YSSR$_9$SSY, CR$_{12}$C, CR$_{12}$, (RKH)$_4$, Y(RKH)$_2$R, etc., basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from Drosophila antennapedia), pAntp, plsl, FGF, Lactoferrin, Transportan, Buforin-2, Bac715-24, SynB, SynB(1), pVEC, hCT-derived peptides, SAP, or histones. In a particularly preferred embodiment, the cationic or polycationic compound is protamine.

Further preferred cationic or polycationic compounds, which may be comprised in the second liquid composition according to the inventive method, may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)-propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]dimethylammonium chloride, CLIP6: rac-[2(2,3-dihexadecyloxypropyl-oxymethyloxy)ethyl]-trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

Preferably, the first liquid composition and/or the second liquid composition further comprise at least one compound selected from a salt or a lyoprotectant.

Preferably, the first liquid composition and/or the second liquid composition comprise at least one salt selected from the group consisting of NaCl, KCl, LiCl, $MgCl_2$, NaI, NaBr, $Na_2CO_3$, $NaHCO_3$, $Na_2SO_4$, $Na_3PO_4$, KI, KBr, $K_2CO_3$, $KHCO_3$, $K_3PO_4$, $K_2SO_4$, $CaCl_2$, $CaI_2$, $CaBr_2$, $CaCO_3$, $CaSO_4$, $Ca(OH)_2$, and $Ca_3(PO_4)_2$.

Preferably, the first liquid composition and/or second liquid composition comprise at least one cation, preferably at least one cation selected from the group consisting of $Na^{30}$, $K^+$, $Li^+$, $Mg^{2+}$, $Ca^{2+}$ and $Ba^{2+}$. Preferred examples of cations and corresponding salts are $Na^+$ (e.g. NaCl), $K^+$ (e.g. KCl), $Li^+$ (LiCl) or $Mg^{2+}$ ($MgCl_2$), particularly preferred is $Na^+$.

The first liquid composition and/or second liquid composition may comprise at least one cation in a concentration of up to 50 mM, preferably of from 0.001 to 50 mM, more preferably from 3 to 30 mM, more preferably from 3 to 20 mM, further preferably from 5 to 15 mM, and most preferred from 5 to 10 mM. It is particularly preferred to add cations in a concentration of at least 3 mM to the first liquid composition. Preferably, the content of cations in the first and/or second liquid composition is 30 mM or less, more preferably from 3 to 30 mM, more preferably from 4 to 26 mM, and especially preferred from 5 to 10 mM. Preferably, the first and/or second liquid composition may comprise $Na^+$ cations in a content of from 4 to 26 mM, more preferably from 5 to 10 mM. In a preferred example, the $Na^+$ content is 9 mM.

In a particularly preferred embodiment, the first liquid composition and/or the second liquid composition comprises a cation in a concentration from 0.1 to 10 mM, more preferably from 1 to 5 mM. In a preferred example, the cation concentration in the first liquid composition and/or the second liquid composition is 4.6 mM.

More preferably, the first liquid composition and/or the second liquid composition comprises an anion in a concentration from 0.1 to 10 mM, more preferably from 1 to 5 mM. In a preferred example, the anion concentration in the first liquid composition and/or the second liquid composition is 4.6 mM.

Preferably, the ratio of cation to RNA in the first liquid composition is from 3 to 30 mmol cation/g RNA, preferably from 4 to 23 mmol cation/g RNA, and most preferably from 5 to 15 mmol cation/g RNA. It is particularly preferred to add cations in a ratio of a least 3 mmol cations/g RNA. Preferably, the first liquid composition comprises $Na^+$ cations and RNA in a ratio of from 4.6 to 27.5 mmol $Na^+$/g RNA, more preferably from 5 to 15 mmol $Na^+$/g RNA and most preferably from 6 to 11 mmol $Na^+$/g RNA. In a preferred example, the first liquid composition comprises $Na^+$ cations and RNA in a ratio of 10.3 mmol $Na^+$/g RNA.

In another preferred embodiment, the first liquid composition comprising RNA does not comprise additional cations.

In a particularly preferred embodiment, the second liquid composition comprises $Na^+$ cations in a concentration from 0.1 to 10 mM, more preferably from 1 to 5 mM. In a preferred example, the $Na^+$ concentration of the second liquid composition is 4.6 mM.

Preferably, the first liquid composition and/or second liquid composition comprise at least one anion selected from the group consisting of $Cl^-$, $CO_3^{2-}$, $PO_4^{3-}$ and $SO_4^{2-}$. Preferably, the concentration of the anion in the first liquid composition and/or second liquid composition is 23 mM or less, more preferably from 1.5 to 23.0 mM, and especially preferred from 5.0 to 10.0 mM. Preferably, the first liquid composition and/or the second liquid composition may comprise $Cl^-$ anions in a content of from 1.5 to 23 mM, more preferably from 5.0 to 10.0 mM. In a preferred example, the $Cl^-$ content is 6.5 mM.

In a preferred embodiment, the first liquid composition comprising RNA does not comprise additional anions.

In another particularly preferred embodiment, the second liquid composition comprises $Cl^-$ anions in a concentration from 0.1 to 10 mM, more preferably from 1 to 5 mM. In a preferred example, the $Cl^-$ concentration of the second liquid composition is 4.6 mM.

Preferably, the first liquid composition and/or second liquid composition comprise at least one component selected from a cryoprotectant, a lyoprotectant or a bulking agent. In this context, cryoprotectants are understood as excipients, which allow influencing the structure of a frozen material and/or the eutectical temperature of the mixture. Lyoprotectants are typically excipients, which partially or totally replace the hydration sphere around a molecule and thus prevent catalytic and hydrolytic processes. A bulking agent (e.g. a filler) is any excipient compatible with the RNA and/or the cationic or polycationic compound. As used herein, a bulking agent may be used for increasing the volume and/or the mass of the liquid compositions. In addition, a bulking agent may also protect the at least one RNA from degradation.

Preferably, the first liquid composition and/or the second liquid composition comprise at least one lyoprotectant. In a particularly preferred embodiment, the second liquid composition comprises at least one lyoprotectant, preferably as defined herein. According to one embodiment, the lyoprotectant is selected from the group consisting of sucrose, mannose, trehalose, mannitol, polyvinylpyrrolidone, and Ficoll 70. Alternatively, the lyoprotectant may be selected from the group consisting of glucose, fructose, sucrose, mannose, trehalose, mannitol, polyvinylpyrrolidone, and Ficoll 70.

Preferably, the concentration of lyoprotectant in the first liquid composition and/or the second liquid composition is in a range of about 0.01 to about 40% (w/w), preferably of about 0.01 to about 30% (w/w), more preferably of about 0.1 to about 20% (w/w), even more preferably of about 0.5 to about 20% (w/w), and most preferably of about 2.5 to about 20% (w/w), e.g. of about 5 to about 20% (w/w), such as about 5% or 10% (w/w). More preferably, the concentration of a lyoprotectant, preferably as defined herein, in the second liquid composition is in a range of about 0.01 to about 40% (w/w), preferably of about 0.01 to about 30% (w/w), more preferably of about 0.1 to about 20% (w/w), even more preferably of about 1 to about 20% (w/w), and most preferably of about 5 to about 15% (w/w), e.g. of about 8 to about 14% (w/w), such as about 10% (w/w)

Preferably, the first liquid composition and/or the second liquid composition comprise at least one component selected from the group of (free) carbohydrates. Such group of (free) carbohydrates may comprise, without being limited thereto, any (free) carbohydrate, suitable for the preparation of a pharmaceutical composition, preferably, without being limited thereto, (free) monosaccharides, such as e.g. (free) glucose, (free) fructose, (free) galactose, (free) sorbose, (free) mannose ("free" preferably means unbound or unconjugated, e.g. the mannose is not covalently bound to the at least one RNA, or in other words, the mannose is unconjugated, preferably with respect to the at least one RNA), etc., and mixtures thereof; disaccharides, such as e.g. lactose, maltose, sucrose, trehalose, cellobiose, etc., and mixtures thereof; polysaccharides, such as raffinose, melezitose, maltodextrins, dextrans, starches, etc., and mixtures thereof; and alditols, such as mannitol, xylitol, maltitol, lactitol, xylitol sorbitol, pyranosyl sorbitol, myoinositol, etc., and mixtures thereof. Examples of sugars that are preferably used in the composition according to the invention include lactose, sucrose or trehalose. Generally, a sugar that is preferred in this context, has a high water displacement activity and a high glass transition temperature. Furthermore, a sugar suitable for use in the first and/or second liquid composition is preferably hydrophilic but not hygroscopic. In addition, the sugar preferably has a low tendency to crystallize, such as trehalose. Trehalose is particularly preferred.

According to a preferred embodiment, the first liquid composition and/or the second liquid composition comprise a carbohydrate component, preferably a sugar, more preferably trehalose. In a preferred embodiment, a carbohydrate component, preferably a sugar, more preferably trehalose is present in the liquid provided in step a) of the method at a concentration of about 0.01 to about 40% (w/w), preferably in a concentration of about 0.01 to about 30% (w/w), more preferably in a concentration of about 0.1 to about 20% (w/w), even more preferably in a concentration of about 0.5 to about 20% (w/w), and most preferably in a concentration of about 2.5 to about 20% (w/w), e.g. at a concentration of about 5 to about 20% (w/w), such as about 10% or 5% (w/w). In a particularly preferred embodiment, the second liquid composition comprises a carbohydrate component, preferably a sugar, more preferably trehalose. In a preferred embodiment, a carbohydrate component, preferably a sugar, more preferably trehalose is present in the liquid provided in step a) of the method at a concentration of about 0.01 to about 40% (w/w), preferably in a concentration of about 0.01 to about 30% (w/w), more preferably in a concentration of about 0.1 to about 20% (w/w), even more preferably in a concentration of about 1 to about 20% (w/w), and most preferably in a concentration of about 5 to about 15% (w/w), e.g. at a concentration of about 8 to about 14% (w/w), such as about 10% (w/w)

Preferably, the first liquid composition is an aqueous solution, preferably having a pH of from 4 to 9, more preferably from 5 to 7. In a preferred example, the pH of the first liquid composition is 5.8.

Preferably, the second liquid composition is an aqueous solution, preferably having a pH of from 4 to 9, more preferably from 6 to 8. In a preferred example, the pH of the second liquid composition is about 7.

Preferably, the first liquid composition and the second liquid composition are provided in a reservoir vessel each, which optionally may be held at a predetermined temperature and/or pressure using appropriate temperature-controlling and pressure-controlling means, respectively, known in the art.

The respective reservoir vessel can be connected to the reactor via any connection means known in the art, e.g. by means of a tube, a hose, tubing, or a pipe.

Materials suitable for the reservoir vessels and connection means are known in the art, and may be the same as those used for the reactor or mixing means as described herein.

According to step c) of the method of the present invention, the first liquid composition comprising at least one RNA and the second liquid composition comprising at least one cationic or polycationic compound are introduced into at least one reactor, wherein the first liquid composition comprising at least one RNA and the second liquid composition comprising at least one cationic or polycationic compound are mixed with a blend time of 5 seconds or less. Preferably, the first liquid composition and the second liquid composition are introduced into at least one reactor in a controlled manner.

Step c) preferably comprises reacting the at least one RNA with the at least one cationic compound. In this context, the term 'reacting' typically relates to the formation of a complex, preferably a nanoparticle, by the at least one RNA and the at least one cationic or polycationic compound.

The first liquid composition and the second liquid composition can be introduced into the reactor by any method known in the art. For example, the first liquid composition and the second liquid composition can be introduced into the reactor by pumping or gravity flow. Preferably, the first liquid composition and the second liquid composition are introduced into the reactor by pumping at a controlled flow rate.

Pumping of the first liquid composition and the second liquid composition can be carried out using any pump known in the art, for example, a syringe pump, such as TSE systems 540060-B, NE-1000 Single Syringe Pump from New Era Pump Systems, Inc.or a KNAUER Smartline Pump 1000 or a peristaltic pump, such as a Watson Marlow Pump 323S or a membrane pump/diaphragm pump such as a Lever Pump or a quattroflow pump.

The first liquid composition and/or the second liquid composition may be introduced into the reactor at any suitable flow rate. Optimum flow rates may be readily determined by a skilled person for any reactor system used.

Preferable flow rates are 0.1 ml/minute or more, more preferably 0.3 ml/minute or more, more preferably 0.5 ml/minute or more, preferably 1.0 ml/minute or more, more preferably 1.5 ml/minute or more, or more preferably 10 ml/minute or more, 50 ml/minute or more, 100 ml/minute or more, or 500 ml/minute or more, and most preferably 750 ml/minute or more. In a preferred embodiment, the flow rate is in a range from about 0.1 ml/minute to 1500 ml/minute, preferably from 0.3 ml/minute to 1000 ml/minute, from 5 ml/minute to 700 ml/minute or from 5 ml/minute to 500 ml/minute. Further preferred flow rates are 5 ml/minute or more, more preferably 10 ml/minute or more, more preferably 50 ml/minute or more, and more preferably 250 ml/minute or 500 ml/minute or more, and most preferably 750 ml/minute or more. More preferably, flow rates are in the range from about 50 ml/minute to 200 ml/minute, even more preferably in the range from about 100 ml/minute to 200 ml/minute. Most preferably the flow rate is about 160 ml/minute.

In a preferred embodiment, the first liquid composition and/or the second liquid composition are introduced into the at least one reactor with a flow rate of 0.1 ml/minute or more, 1 ml/minute or more, 10 ml/minute or more, preferably 50 ml/minute or more, more preferably 100 ml/minute or more, more preferably 150 ml/minute or more, more preferably 300 ml/minute or more, more preferably 800 ml or more, most preferably in a range of 100-800 ml/minute via a pump device.

Preferably, the first liquid composition and/or the second liquid composition are introduced into the reactor at the same flow rate.

In a particularly preferred embodiment, the first liquid composition and the second liquid composition are concurrently introduced into the at least one reactor, preferably under controlled conditions e.g. at constant flow rates.

In the context of the invention, the term "controlled conditions" or "introduced into the at least one reactor, preferably under controlled conditions" typically refers to stable, non-variable conditions that are applied to introduce the first liquid composition and the second liquid composition into the reactor, e.g. a mixer as described herein. These "controlled conditions" may be controlled flow rate, liquid flow, pump rate, pump flow, injection rate, injection flow, pressure, temperature and the like. Preferably, the term "controlled conditions" relates to constant flow rates and/or constant liquid flow.

Preferably, the first liquid composition and the second liquid composition are introduced into the at least one reactor so that the at least one RNA and the at least one cationic or polycationic compound are present in the reactor with a N/P-ratio (defined as above) of about 0.1-10, preferably in a range of about 0.3-4 and most preferably in a range of about 0.5-2 or 0.7-2 regarding the ratio of mRNA:cationic or polycationic compound and/or polymeric carrier, preferably as defined herein, in the complex, and most preferably in a range of about 0.7-1.5, 0.5-1 or 0.7-1, and even most preferably in a range of about 0.3-0.9 or 0.5-0.9.

In the context of the invention, the term 'reactor' is used for a vessel providing a reaction space or volume (sometimes also referred to as 'reaction chamber'), wherein the first liquid composition comprising at least one RNA and the second liquid composition comprising at least one cationic or polycationic compound are mixed and reacted. The reactor may by an open vessel or a closed vessel, without limitation regarding the shape or the dimension of the vessel.

In the context of the present invention, the reactor may optionally comprise appropriate temperature-controlling and/or pressure-controlling means, respectively, to control a predetermined temperature and/or pressure within the reactor. Suitable temperature-controlling and pressure-controlling means are known in the art. The reaction space is typically defined by the walls of the reactor and the fill level. If a reactor is operated in a completely filled state, the reaction space (reaction chamber) corresponds to the total liquid volume held by the reactor, wherein the total liquid volume is preferably defined by the enclosing walls of the reactor.

Preferably, an open vessel comprises an opening at its upper side, preferably an open top. The open reactor can be advantageously filled and emptied through its opening. The reactor may comprise inlet and/or outlet ports. If the reactor is a closed vessel, the reactor will comprise appropriate inlet and outlet ports for introducing the first and second liquid compositions, and for recovering the product liquid composition, respectively. Such ports are preferably designed to control the inlet or outlet flow, respectively. Such ports are known in the art and may be of any kind suitable for the purpose of controlling the flow of a liquid composition. Optionally, the reactor may also comprise additional components, such as (safety) valves, etc.

The method of the present invention is preferably conducted at a temperature in a range of from 4 to 50° C., more preferably from 10 to 30° C., and most preferably at room temperature, about 20° C. Accordingly, the reactor system preferably comprises appropriate temperature-controlling means (e.g. cooling and/or heating means, temperature sensors, and the like), which allow to conduct the method of the invention in a temperature range of from 4 to 50° C., more preferably from 10 to 30° C. and most preferably at about 20° C. (room temperature). Preferably, the first liquid composition, the second liquid composition and/or the mixture of the two in the reaction chamber have a temperature as defined above. Suitable means for cooling and/or heating such a system or parts of such a system are known in the art.

The reactor and its components may be manufactured from any suitable material, preferably from a material that is inert to any reagent, solvent and product of the reaction to be carried out within the reactor. For example, the reactor material should be inert to both acids and bases as well as to any suitable solvent. Suitable materials for the reactor include, for instance, glass, metals, such as, e.g., steel, preferably stainless steel, polymeric compounds, such as, e.g., polyolefins, for example, polyethylene, fluorine-containing polymeric compounds, for example, polytetrafluoroethylene (PTFE, Teflon®), polypropylene, polyvinylidene fluoride (PVDF), polyvinyl chloride (PVC), chlorinated polyvinyl chloride (CPVC), and polyacetal (polyoxymethylene) Preferred materials are polymeric compounds, glass or steel.

Preferably, the at least one reactor is one single reactor.

Preferably, the reactor has a volume in a range from 0.1 ml to 10 l, preferably from 0.5 ml to 5 l, more preferably from 1 ml to 500 ml and most preferably from 1 ml to 100 ml.

The reactor may be of any type and design known in the art, as long as the reactor is provided with a design allowing the mixing and reacting of the first and second liquid compositions under controlled conditions, preferably the simultaneous mixing and reacting of the first and second liquid compositions under controlled conditions. The term 'simultaneous mixing and reacting' means that the first and second liquid compositions are thoroughly mixed and, at the same time, the reaction between the at least one RNA in the first liquid composition and the at least one cationic or polycationic compound in the second liquid compositions is conducted, i.e. started and completed. In other words, the reactor design provides a reaction space (reaction chamber), wherein the reaction between the at least one RNA and the at least one cationic or polycationic compound is completed under thoroughly controlled conditions.

According to an embodiment of the present invention, the reactor is a tank reactor. As used herein, the term 'tank reactor' is typically used for a reactor, which comprises an open or closed vessel, such as, for instance a container of any shape or size, in which the first liquid composition and the second liquid composition are mixed and reacted as described herein.

The first liquid composition and/or second liquid composition may be introduced into the reactor and/or recovered from the reactor as a bulk, preferably in a discontinuous process. Alternatively, the first and/or second liquid composition may be introduced into the reactor and/or recovered from the reactor by a suitable inlet and/or outlet, respectively, preferably in a continuous process. In specific embodiments, the first and/or second liquid composition preferably flow through the reactor (such as, for example, a tube reactor), wherein the liquid compositions are mixed and reacted as described herein.

According to step d) of the inventive method, the product liquid composition comprising the nanoparticle comprising the at least one RNA and the at least one cationic or polycationic compound is recovered from the reactor. In a preferred embodiment, the product liquid composition is recovered after completion of the reaction. Thereby, the method according to the present invention produces a nanoparticle, which is characterized by uniform average particles size and polydispersity, reliably, under controlled conditions.

By the method according to the present invention, the formation of unwanted side products resulting from unwanted side reactions is reduced or altogether avoided. It was found that a product liquid composition, for which the presence of unwanted side products resulting from unwanted side reactions can be detected by measurement of absorption and/or turbidity directly after the production thereof, is of poor quality with respect to the desired nanoparticle or is likely to deteriorate subsequently, for instance by formation of aggregates or precipitates. In particular, it was found that such unwanted side products and/or side reactions adversely affect the stability of the product liquid composition, especially upon (long term) storage, which is a product property required for pharmaceutical applications. An uncontrollable formation of precipitates would lead to compositions having uncontrollable concentrations of the active ingredient (RNA-comprising compound and/or nanoparticle), which is completely unacceptable for pharmaceutical applications. However, the product liquid compositions obtained according to the method of the present invention were found to be of superior quality, stability and unaffected from such unwanted side products and/or side reactions.

It was found that the presence of unwanted side products (e.g. precipitates) resulting from unwanted side reactions results in a reduction of clarity, preferably as determined by absorption measurement, preferably at a wavelength of 350 nm, and/or an increase of turbidity of the product composition, so that the measurement of absorption and/or turbidity of the product liquid composition provides a fast and reliable way for detecting unwanted side products resulting from unwanted side reactions. A measurement of absorption and/or turbidity can easily be integrated into a production process, even when operated continuously. A person skilled in the art will readily know how to incorporate the appropriate measurements of absorption and/or turbidity into the reactor system and/or production method according to the present invention.

Thus, the method according to the present invention produces a nanoparticle, which is characterised by uniform average particles size and polydispersity, reliably under controlled conditions, without allowing unwanted side reactions resulting in unwanted side products and stability issues caused thereby, independent of the scale of production. Further, the method according to the present invention is both cost-effective and reliable, particularly on a large scale, which renders the method of the invention especially suitable for the pharmaceutical production of RNA-comprising nanoparticles at an industrial scale.

According to the invention, the at least one reactor is characterised by a blend time of 5 seconds or less. Preferably, the blend time is 2.5 seconds or less, more preferably 2.0 seconds or less, more preferably, 1.0 second or less, more preferably 0.5 second or less, more preferably 0.25 second or less, more preferably 0.1 seconds or less and most preferably 0.05 seconds or less. Alternatively, the blend time is preferably in a range from about 0.001 seconds to about 5 seconds, more preferably from about 0.01 seconds to about 5 seconds, even more preferably from about 0.1 seconds to about 5 seconds and most preferably from about 0.001 to about 2 seconds or from about 0.01 to about 2 seconds.

The term "blend time" (also referred to as "mixing time" or "macro-mixing time" in the art) is commonly used in the art to indicate the time required to reach a predefined degree of homogeneity in a vessel or reactor (also referred to as 'uniformity') under predetermined reaction conditions. The blend time is known to depend on the reactor design as well as various operational conditions of the reactor, for example, on size and geometry of the reaction chamber, size and geometry of an optional mixer and/or stirrer, the mixing or stir rate, size and geometry of optional baffles, energy input, the flow rate of the individual solutions, viscosity of the solutions, temperature, and the like, which are readily adjusted accordingly by the skilled person.

In the context of the present invention, "blend time" typically refers to the time required reaching homogeneity (uniformity) of the mixture of at least 50%. Preferably, the homogeneity (uniformity) is 50% or more, more preferably 60% or more, more preferably 70% or more, more preferably 80% or more and most preferable 90% or more.

Methods for the experimental determination and semi-theoretical prediction of the blend time in reactors (such as mixers) are known in the art. Typically, these methods consist of adding a small amount of a miscible tracer to the liquid in the reactor (e.g. a mixer), and monitoring the concentration of the tracer with time at different locations throughout the system. Examples of tracers comprise tracers that can be detected by optical means (e.g. by color and/or absorption measurements, or the like), by conductivity measurements (e.g. by measurement of the electrical or thermal conductivity, or the like), by radioactivity, and the like. Typically, the tracer concentration at a given point in the system fluctuates with time. However, the amplitudes of the concentration fluctuations decrease over time, and eventually the local concentration converges asymptotically toward the ultimate homogeneous concentration value corresponding to a uniform dispersion of the tracer in the entire system. Preferably, when using a colorimetric tracer, image processing of digitized images of the mixing system can be used, in combination with imaging processing software, to detect a color change at a particular location in the vessel very precisely. The blend time is defined as the time required by the tracer liquid system to reach a desired and predefined level of tracer concentration uniformity (homogeneity) at a predefined location. Usually, a 70%, 80%, 85%, 90% or 95% uniformity level (homogeneity) is defined as the endpoint of the blending process.

Preferably, the blend time is experimentally determined, preferably by a method selected from a colorimetric method, a method based on conductivity measurements, and a chemical method. Alternatively, the blend time may be determined experimentally, preferably by a method selected from a colorimetric method, a method based on conductivity measurements, a chemical method, or by simulation, e.g. by computational fluid dynamics (CFD).

An example of a colorimetric method for determining the blend time experimentally comprises a method, wherein at least one miscible coloured tracer compound (e.g. a coloring agent, a dye, a pigment, or the like) is added to the composition in the reactor, preferably before or concurrently with the introduction of the first liquid composition and the second liquid composition, and the change of color is detected in the whole reactor or a definite zone by means of an optical detector. The blend time is the time interval from the introduction of the tracer to the time, when a predetermined uniformity level (homogeneity) of the distribution of the tracer is detected (e.g., a 95% uniformity level, usually chosen in the art).

An example for a method based on conductivity measurements for determining the blend time experimentally comprises using a measurement of a physical quantity (e.g. measurement of the thermic or electric conductivity, or the like) to detect the concentration and/or distribution of at least one miscible tracer (e.g., an electrolyte, or the like). The tracer is added to the composition in the reactor, and the change of a physical quantity, which is proportional to the concentration of the tracer, is measured in the whole reactor or in a definite zone by means of one or more probes. The blend time is the time interval from the introduction of the tracer to the time, when a predetermined uniformity level (homogeneity) of the distribution of the tracer is detected (e.g., a 95% uniformity level, usually chosen in the art).

A method for determining the blend time using a radioactive tracer is carried out in a manner analogous to the colorimetric and/or conductimetric method, wherein the concentration of the at least one radioactive tracer is measured in the whole reactor or in definite zones by means of a suitable detector.

An example for a chemical method for determining the blend time experimentally comprises using a chemical reaction, preferably an instantaneous chemical reaction (e.g. an acid-base-type reaction in aqueous systems), wherein a suitable first reactant (for example, an acid solution, such as, e.g. aqueous HCl, or the like) is added in stoichiometric excess to the composition in the reactor comprising a suitable second reactant (for example, a basic solution, such as, e.g. aqueous NaOH, or the like). The blend time is the time necessary to achieve equivalence conditions in the whole reactor or a definite zone, wherein the equivalence point can preferably be determined by means of a color change of a suitable indicator (colorimetric method), a measurement of conductivity, a measurement of pH, or the like. The respective detection can be carried out in the same way as described for the colorimetric and conductimetric methods, including all detectors, probes, conditions, etc. utilized therein.

A further example of a chemical method for determining the blend time experimentally comprises the use of two or more indicators or tracers. A preferred example for a chemical method using two indicators simultaneously is the DISMT method (Dual Indicator System for Mixing Time) as described in Melton et al. (DISMT-Determination of mixing time through color changes, Chemical Engineering Communications Volume 189, Issue 3, 2002). This method uses a semi-quantitative visualization of liquid/liquid mixing processes in color changes. In DISMT, two liquids, one red and one blue, are mixed to produce a yellow liquid. Through appropriate choice of the acid-base indicators used, and the initial pH's of the two solutions, the yellow liquid appears only in those regions where the mixing fraction is within a designated fractional deviation (say 5%) of the infinite time mixing fraction. Thus, the 95% mixing time/distance can be defined, for the whole volume of the mixing system, as the time/distance for all of the liquid to become yellow. DISMT makes use of two standard acid-base indicators, methyl red (red to yellow, pK~5) and thymol blue (yellow to blue, pK~9). Both indicators are added to both unmixed solutions. A red (acidic) solution is mixed with a blue (basic) solution, and in those regions where the mixing fraction is within 5% of the mixing fraction at infinite time, the solution is yellow. With a clear mixing vessel, an observer may see distinct red and blue regions as well as the later emergence of yellow regions. With DISMT, the 95% mixing time for the entire vessel may be defined as the time for the entire liquid volume to become yellow. The fundamental idea underlying the DISMT method is that two color changes are used to mark two acid-base mixing fractions, $fl=(1-\delta) \times f\infty$ and $fh=(1+\delta)*f\infty$, where $f\infty$ is the acid mixing fraction at infinite time. By appropriate adjustment of the initial pH's of the two liquids to be mixed, the pH's at these two mixing fractions will be the pKa of the basic indicator and the pKa of the acidic indicator, respectively. The chemistry underlying DISMT is that of a strong acid/strong base aqueous titration in the presence of two weak acids, the pH indicators. The titration equation is described in Melton et al. and is incorporated herewith by reference.

Preferably, a colorimetric method comprises image processing of digitized images of the whole reactor in combination with imaging processing software. Thereby, it is advantageously possible to detect a color change at a particular location in the reaction chamber very precisely, and thus the respective (local) concentration of the tracer and/or indicator, as well as the changes thereof.

Alternatively, the blend time of a reactor can be determined by computer simulations using computational fluid dynamics (CFD) (cf., e.g., Bai et al., 2007. J. Pharm. Sci. 96(11):3072-86, incorporated herein by reference).

Such methods for determining the blend time are described in detail in the art and were shown to be highly reproducible (cf. e.g. Bai et al., 2007. J. Pharm. Sci. 96(11): 3072-86; Cabaret et al. (Mixing Time Analysis Using Colorimetric Methods and Image Processing. Industrial & Engineering Chemistry Research, 2007. 46: p.); Paul, E. L., Atiemo-Obeng, V. A, Kresta, S. M. Handbook of Industrial Mixing. 2004, Hoboken: John Wiley & Sons, Inc.; Manna L. 1997. Comparison between physical and chemical methods for the measurements of blend times. Chem Eng J 67:167-173; all incorporated herein by reference).

In the present invention, a method of colorimetric measurement of the blend time is preferably used, wherein the blend time is preferably measured by visual inspection, more preferably in a non-intrusive manner.

In a particularly preferred embodiment, the blend time is experimentally determined by a chemical method based on colorimetric measurements.

In a further preferred embodiment, in order to determine the blend time in a reactor (e.g. in a dynamic mixer), the following method derived from Bai et al. may be used: The mixing chamber (reactor chamber) is filled with an appropriate volume of a basic solution, (preferably NaOH, preferably 0.01-1 mol/L) (solution 1). A pH indicator is added (preferably bromophenole blue or phenolphthalein, preferably in a concentration of 0.01%). Under stirring (but without flow-through), a volume and molar equivalent of an acid solution (same volume and same molarity as solution 1) (solution 2) is added to solution 1 and the time needed for colour change of the pH indicator is measured. Preferably, the measurement is carried out in at least quintruplicates. (Solution 1 and Solution 2 can be interchanged).

In the context of the present invention, a uniformity level (homogeneity) is defined as the endpoint of the mixing process, i.e. the time point, when blend time is determined. More preferably, the endpoint of the mixing process is defined by a uniformity level (homogeneity) of at least 70%, at least 80%, at least 85%, at least 90% or most preferably at least 95%.

To simplify the measurement of the blend time (particularly if short blend times are measured), a solution increasing the viscosity as e.g. glycerol may be added to solution 1 and/or 2, preferably in a concentration of from 1 to 90% (v/v), more preferably in a concentration of from 50 to 80% (v/v), most preferably in a concentration of 75% (v/v). In this set-up, the blend time determined with solutions comprising glycerol is longer compared to solutions without glycerol and therefore having a lower viscosity. Thus, it can be concluded that the specific conditions used for determining the blend time (stirring rate, etc.) resulting in a specific measured blend time (e.g. 5 s or 2 s) result in a shorter blend time, if solutions to be mixed are used without glycerol and therefore with a lower viscosity.

In a specific embodiment of the present invention, the blend time of a reactor is determined according to the measurement method described in detail in the following:

The reaction chamber of the reactor is filled completely with a solution of 75% glycerol/0.01M NaOH/0.01% bromophenol blue in water (solution 1). Under stirring (but without flow-through), a volume of 0.01 M HCl corresponding to 0.01 volume equivalents of solution 2 is added and the time until the colour has changed from purple to yellow is recorded visually in quintuplicates.

According to the method of the invention, the reaction between the at least one RNA in the first liquid composition and the at least one cationic or polycationic compound in the second liquid composition is conducted, i.e. started and preferably completed, within the reaction chamber of the reactor (e.g. a tank reactor). Subsequently, the product liquid composition comprising the nanoparticle comprising the at least one RNA and the at least one cationic or polycationic compound is recovered from the reactor in step (d). By conducting the complete reaction in the reaction chamber of the reactor under controlled conditions, unwanted side reactions and the formation of unwanted side products can be avoided advantageously, so that a product liquid composition is obtained, which comprises the nanoparticle comprising the at least one RNA and the at least one cationic or polycationic compound, which is characterised by uniform average particles size and polydispersity, reliably under controlled conditions, independent of the scale of production.

The product liquid composition may be recovered by any means known in the art, for example means as those used to introduce the first and second liquid compositions into the reactor, e.g. by pumping, or the like.

In the case of an open reactor, the product liquid composition may by recovered through the opening of the reaction chamber, e.g. by suction pumping, or the like, or by means of passive transport, e.g. a syphon controlling the fill level of the reaction chamber, or the like.

In the case of a closed reactor under continuous operation, the product liquid composition may also be recovered from the reactor by means of passive transport, e.g. a flow resulting from the pressure build-up in the reactor caused by a continuous introduction of the first and second reagent compositions, or the like.

Preferably, the product liquid composition is recovered from the reactor and transferred to a reservoir vessel, which optionally may be held at a predetermined temperature and/or pressure using appropriate temperature-controlling and pressure-controlling means, respectively, known in the art. The reservoir vessel can be connected to the reactor via any connection means known in the art, e.g. by means of a tube, a hose, tubing, etc. Materials suitable for the reservoir vessel and connections means are known in the art, and may be the same as those used for the reactor described above.

Alternatively, the product liquid composition may be divided appropriately and transferred to individual dosage vessels, which optionally may be sealed thereafter, or the like, using means for dividing and filling known in the art, optionally maintaining a predetermined temperature and/or pressure using appropriate temperature-controlling and pressure-controlling means, respectively, known in the art.

Preferably, the at least one reactor comprises at least one mixing means. In a preferred embodiment, the reactor comprises at least one dynamic mixing means and/or at least one static mixing means.

In the context of the invention, the term 'mixing means' is used for a device that mixes the content of the reaction chamber of the reactor. In principle, any device known in the art may be used in the present invention, as long as the following requirements are provided: The mixing means must allow to thoroughly mix the contents of the reaction chamber of the tank reactor, and that the tank reactor has a blend time of 5 seconds or less. The mixing means mixes the contents of the reactor with a blend time of 5 seconds or less. As used herein, the term 'mixing means' may also refer to a feature or a specific structure of the reactor (e.g. a static mixing means), which allows mixing of the first and second liquid compositions. In the context of the present invention, a 'static mixing means' may also be any feature of a reactor or mixer, which creates a turbulence that results in mixing of the first and second liquid composition. A person skilled in the art will readily know, which mixing means is appropriately selected for any given reactor design. Suitable types and designs of mixing means, as well as their respective properties in combination with different reactor designs, are known in the art, for example, as described, e.g., in Steffe J F., Mixing and Agitation, Chapter 10 "Mixing and Agitation", pages 287 to 304, etc. (Steffe J F. Mixing and Agitation [Internet]. Second Edition. [cited 2013 Jan. 13] Available on the world wide web at pacontrol.com/process-information-book/Mixing%20and%20Agitation%2093851_10.pdf), which is incorporated herein by reference.

In the context of the invention, "mixing" is typically a process that involves manipulation of a heterogeneous physical system with the intent to make it more homogeneous. Mixing is performed to allow mass transfer to occur between one or more streams, components or phases. Mixing is fundamentally the evolution in time of spatially dependent concentrations toward a final homogeneous state.

A mixing means is defined herein as a device or a structure that provides mixing of at least two components to be mixed under controlled conditions.

In the method of the invention, two liquids are mixed, namely the first liquid composition and the second liquid composition. Thereby, the reagents respectively comprised therein are brought into contact for reaction under controlled conditions.

In a preferred embodiment of the present invention, wherein the reactor comprises at least one mixing means, the blend time of 5 seconds or less can be readily maintained in the reactor system and/or adjusted upon change of other process parameters and/or conditions.

Preferably, the at least one mixing means comprises at least one dynamic mixing means and/or at least one static mixing means. Suitable dynamic mixing means and static mixing means are known in the art (cf. above).

According to a preferred embodiment of the invention, the reactor is a dynamic mixer, which preferably comprises at least one dynamic mixing means. Dynamic mixers are typically systems with at least one moving element (or dynamic mixing means), such as a moving stirring means or a moving vessel. A dynamic mixer is any mixer that provides agitation and mixing of the solutions/components to be mixed therein by application of mechanical forces, for example, agitation by movement of a paddle or blade connected to an external power source, such as a motor or a magnetic stirrer. In such instances, the mixing of the solutions/components to be mixed is accomplished by the rotation of the paddle or blade, which creates the turbulence necessary for mixing. In another embodiment agitation and mixing is performed by a shaker, vortexer or the like. The dynamic mixers appropriate for use in the methods and apparatuses disclosed herein should comprise materials (e.g., stainless steel, glass, polyethylene) which are inert to the reaction conditions, do not react with the solutions/components to be mixed and/or do not influence the components to be mixed. Such materials are used in the areas of the mixer where the solutions/components to be mixed contact the mixer.

Dynamic mixers are commercially available and may be purchased, for example, from Knauer (Germany, Dynamic mixing chamber order #A1174), Sielc (USA, Dynamic mixer order #DMP-1031050) or Gilson (USA, Dynamic mixer 811 D, order #LT3634D).

In the context of the present invention, a mixing means is preferably used, which allows for sufficient mixing of the components as defined herein, preferably without exerting excessive mechanical stress (such as shear stress) on said components. It is believed that the stability of the at least one RNA, preferably a long chain RNA or a mRNA as defined herein, the cationic or polycationic compound and/or of the nanoparticle is increased by using appropriate (dynamic or static) mixing means. In particular, mixing means that are known to induce mechanical stress on the components to be mixed are preferably avoided according to the present invention. For example, a mixing means as used herein does preferably not shake and/or agitate (such as when using a 'Vortex' mixer) the at least one reactor, the first liquid composition and/or second liquid composition. According to one embodiment, the first liquid composition and the second liquid composition are preferably mixed without shaking and/or agitating the at least one reactor or the liquid compositions, respectively. More preferably, the term 'agitating' as used with respect to the inventive method refers to a process that does not involve mechanical stress, such as shaking. The term 'agitating' preferably refers to mixing of the components by turbulences that are not caused by shaking or vibrating of the reactor or the first and/or second liquid composition. It is particularly preferred that the first liquid composition and the second liquid composition are mixed without the use of a 'Vortex' mixer, or the like.

In another preferred embodiment of the invention, the reactor is a static mixer, which preferably comprises at least one static mixing means. Static mixers are typically systems, in which the mixing process is typically initiated by using the hydrodynamic energy of a fluid (liquid/gas) passing through a cavity, such as a pipe or canal, with fixed fittings. Static mixers are stationary systems, through which the material is flowing. In one embodiment, the mixing effect is exclusively achieved by vortexing the flow with the aid of at least one static mixing means. As used herein, a static mixing means is typically an integral element of the reactor, which is not moving. Preferably, the at least one static mixing means comprises at least one static element, preferably at least one static element positioned within a flow path of the first liquid composition and/or the second liquid composition. Moreover, as used herein, a 'static mixing means' may also be any feature, such as the injection of one liquid into another liquid stream, which results in a turbulence that leads to mixing of the liquids. Alternatively, the system may further comprise dynamic mixing means, which contribute to the mixing effect. Precondition for the application of static mixers is the pumpability of the original materials. A static mixer is preferably a mixer that does not rely on mechanical agitation, shaking or stirring by a mechanical device in the mixer. Rather, a static mixer relies on static elements, such as walls, channels, capillaries, barriers, offset plates or protrusions such as rods or nubs, or the like, any of which may comprise holes or openings, or be offset from one another, or the like, to direct the flow path in a way to provide flow turbulence and mixing of the solutions/components to be mixed as they proceed through the mixer. In such a case, the flow rate and pressure is determined by a number of factors, including for example, the flow rate of each solution being introduced, the size and diameter of the connectors and inlet and outlet openings in each component, the size and shape of the chamber, the volume to surface area ratio of the mixer, the number of flow paths and flow path diversions in the mixer, and the like. The mixer may comprise a tee configuration or a serpentine configuration.

In a specific embodiment, the reactor is a static mixer as described herein (e.g. a tube reactor) and comprises an elongate cavity, through which the first liquid composition and/or the second liquid composition flow. In this context, the elongate cavity may have any shape or dimension, as long as the first and the second liquid compositions are mixed with a blend time of 5 seconds or less. Preferably, the cavity may have the shape of a cylinder, a tube, a pipe, a capillary or a hose.

In a further preferred embodiment, the reactor is a static mixer, wherein one liquid composition selected from the first liquid composition and the second liquid composition flows through the reactor and the respective other liquid composition is injected into the liquid that flows through the reactor, wherein the respective other liquid composition is injected in the reactor or upstream of the reactor. The liquid is preferably injected at the center of the liquid that flows through the reactor.

A static mixer is typically a precision device, which is preferably engineered for the continuous mixing of fluid materials. One example of a design of a static mixer is the plate-type mixer. Another example is a static mixer comprising at least one static mixing means contained in a cylindrical (tube) or squared housing. Mixer size can vary from about 6 mm to 6 meters diameter. Typical construction materials for static mixer components include stainless steel, polypropylene, PTFE (Teflon®), PVDF, PVC, CPVC and polyacetal.

Static mixers can use flow division or radial mixing for mixing.

Flow division: In laminar flow, a processed material is divided at the leading edge of each element of the mixer and follows the channels created by the element shape.

Radial mixing: In either turbulent flow or laminar flow, rotational circulation of a processed material around its own hydraulic center in each channel of the mixer causes radial mixing of the material. Processed material is intermixed to reduce or eliminate radial gradients in temperature, velocity and material composition.

Commericial suppliers of static mixers are, for example, Sulzer (Switzerland, e.g. SMX mixing elements), Nordson (USA) or Chromatographie Handel Müller (Germany, order #760092).

A mixing means comprised in the reactor used in the method of the present invention may comprise both dynamic and static mixing elements, e.g. one or more impeller blades in combination with baffles, or the like.

Preferably, the at least one mixing means comprises at least one stirring means. Suitable stirring means are known in the art (cf. above). The stirring means may be any known stirrer design known in the art, e.g. impeller blades or paddles mounted on an axis driven by an external motor, a stir bar driven by a magnetic force provided by an external rotation device, or the like.

A preferred embodiment of a stirring means is a magnetic stirrer, wherein the reaction chamber comprises a stirring bar (such as a magnetic stirrer), which is rotated by a magnetic force provided by an external device (motor). The dimension of the stirring bar can be appropriately selected in accordance with the reactor design, size, etc. Preferable examples of stirring bars comprise a core made of a magnetisable material (e.g. iron, or the like) which is coated with an inert material (usually PTFE, Teflon®, or the like). Another preferred embodiment of a stirring means is an impeller, which is known in the art.

Preferably, the rotational speed of the stirring means can be controlled by controlling the respective speed of the drive, either step-wise or infinitely variable.

Preferably, the stirring means can be operated at a stirring rate of at least 300 rpm, preferably of at least 500 rpm, and more preferably of at least 1000 rpm.

In a preferred embodiment of the present invention, wherein the mixing means comprises at least one stirring means, the rotational speed of which can be controlled, the blend time of 5 seconds or less can be readily maintained in the reactor system and/or adjusted upon change of other process parameters and/or conditions.

In a preferred embodiment, the reactor, preferably a tank reactor, comprises at least one stirring means, preferably a single stirring means. However, the reactor can also comprise two or more stirring means, e.g. in the form of two impellers mounted on opposite sites of the reaction chamber (e.g. at the top and bottom thereof), which may be operated in the same or the opposite rotational direction, at the same or different rotational speeds, and the like.

According to the method of the present invention, the first liquid composition comprising at least one RNA and the second liquid composition comprising at least one cationic or polycationic compound are introduced into at least one reactor.

Preferably, the method of the invention is conducted continuously or discontinuously (non-continuously).

For a discontinuous operation, for example, the method is typically carried out using predetermined batches, e.g. by introducing predetermined volumes of both the first liquid composition and the second liquid composition into the reactor, and, after completion of the reaction, recovering the product liquid composition preferably having a volume corresponding to the combined volumes of the first and second liquid compositions from the reactor. This procedure is then repeated.

A discontinuous operation is preferably carried out in a reactor adapted for discontinuous operation (also referred to as "Non-continuous Reactor"). In the context of the invention, a "Non-continuous Reactor" is a reactor, preferably a tank reactor, that controls that at least two liquid compositions (solutions), which are to be mixed and reacted, mix, contact, and react in the reactor under controlled conditions, and that the product liquid composition remains in the reactor where the mixing and reaction occurs, until recovered in a subsequent step. Typically, the total liquid volume in the reactor increases and is limited by the reaction chamber volume. An example of a Non-continuous Reactor is Reactor II shown in FIG. 2.

For a continuous operation, for example, both the first liquid composition and the second liquid composition are continuously introduced into the reactor, and the product liquid composition is continuously recovered from the reactor. The product liquid composition is recovered with a flow rate that corresponds to the combined flow rates of the first and second liquid compositions (also referred to as "total flow rate"). Preferably, the flow rates of both the first liquid composition and the second liquid composition are identical, so that the total flow rate of the product liquid composition is the sum of the flow rate of the first liquid composition and the second liquid composition, respectively. In this case, the means for recovering the product liquid composition from the reactor must allow for the larger flow rate and volume.

According to another embodiment, a continuous operation is carried out in a reactor, preferably in a reactor adapted for flow-through operation (also referred to as "Continuous Reactor"), such as a flow-through reactor with an elongate cavity, e.g. a tube reactor, a tank reactor adapted for flow-through operation, or any other reactor suitable for flow-through operation. In the context of the invention, a "Continuous Reactor" is a reactor that simultaneously controls that at least two liquid compositions (solutions) to be mixed and reacted mix, contact, and react in the reactor under controlled conditions, and that product liquid composition exits from the continuous reactor at a controlled rate. Preferably, the total liquid volume in the mixing device is maintained constant. A continuous reactor allows the flexible scale-up of the reaction process. Therefore, the use of a continuous reactor is particularly preferred. A continuous reactor is also referred to herein as "Flow-Through Reactor". Preferred examples of a continuous reactor are a closed tank reactor in continuous operation or a static mixer, such as a flow-through reactor with an elongate cavity, e.g. a tube reactor or an injection mixer. Examples of a continuous reactor are Reactors III to VII as shown in FIGS. 4, 5, 6, 10, 11, 12, 13 and 14.

Preferably, the first and the second liquid compositions are introduced into the at least one reactor successively or concurrently.

In one preferred embodiment of the method of the present invention, the first and the second liquid compositions are introduced into the at least one reactor successively. For a successive introduction, for example, one of the first and second liquid compositions are first introduced into the reactor, then the other liquid composition is added thereto, either stepwise or continuously. A successive introduction method is preferably carried out in combination with a reactor, such as a tank reactor, in discontinuous (batch) operation as described above ("Non-continuous Reactor").

In an alternative preferred embodiment of the present invention, both the first liquid composition and the second liquid composition are concurrently (simultaneously) introduced into the at least one reactor. For a concurrent introduction, for example, both the first liquid composition and the second liquid composition are introduced into the reactor at the same time (simultaneously), preferably in amounts to provide the predetermined ratio of products to be reacted as defined herein, especially preferred in equal volumes of the first and second liquid compositions (e.g. by using equal flow rates). A concurrent introduction method is preferably carried out in combination with a flow-through reactor, such as a tube reactor or a flow-through tank reactor in continuous operation as described above ("Continuous Reactor").

Especially preferred, both the first liquid composition and the second liquid composition are concurrently introduced into the at least one reactor with the same flow rate.

In an especially preferred embodiment of the invention, the method of the invention is conducted continuously with concurrent introduction of the first and second liquid compositions, the at least one reactor is a flow-through tank reactor, and the at least one mixing means is a dynamic mixing means, preferably a stirring means. Alternatively, the method of the invention is conducted continuously with concurrent introduction of the first and second liquid compositions, wherein the at least one reactor is a flow-through reactor, preferably a static mixer, more preferably a static mixer as defined herein.

In another preferred embodiment of the invention, the method of the invention is conducted discontinuously with successive introduction of the first and second liquid compositions, the at least one reactor is a non-continuous tank reactor, and the at least one mixing means is a dynamic mixing means, preferably a stirring means.

In another preferred embodiment of the method according to the present invention, the first liquid composition comprising at least one RNA and the second liquid composition comprising at least one cationic or polycationic compound are continuously introduced into at least one flow-through reactor, in which the first liquid composition and the second liquid composition are mixed and preferably simultaneously reacted with each other, wherein the flow-through reactor comprises at least one static mixing means. Preferably, the flow-through reactor is a static mixer as defined herein (e.g. a tube reactor) and comprises an elongate cavity. According to that embodiment, the flow-through reactor, which is a static mixer, may optionally comprise one or more dynamic mixing means as defined herein.

In the context of the invention, a "flow-through reactor" is a typically a continuous reactor wherein the first liquid composition and/or the second liquid composition is continuously flowing through the reaction chamber, which preferably comprises or consists of an elongate cavity. In a preferred embodiment, the flow-through reactor is a static mixer as described herein, which preferably comprises an elongate cavity (e.g. a tube reactor). In the context of the present invention, the elongate cavity of a flow-through reactor may have any shape or dimension, as long as the first and the second liquid compositions are mixed with a blend time of 5 seconds or less. Preferably, the elongate cavity may have the shape of a cylinder, a tube, a pipe, a capillary or a hose. In a preferred embodiment, the flow-through reactor has a straight shape or is bent (e.g. in helices or any other type of curves). The cross-section of such a reactor may also be of any shape, such as circular, oval, rectangular, polygonal or any arbitrary shape. The diameter of the reactor may be constant over its length or vary. In a preferred embodiment, the flow-through reactor, preferably the inner walls of the flow-through reactor, comprise at least one static mixing means as described herein, such as a protrusion, which preferably represents an obstacle for the liquid passing through the reactor. Examples of such reactors are known in the art and may also be referred to as a "tube reactor", "tubular reactor" or "pipe reactor", or the like. For example, a flow-through reactor may have the form of a tube, wherein the reagents are continuously introduced into one end thereof, while the products are continuously recovered from the other end thereof. In a preferred embodiment, a flow-through reactor, preferably with an elongate cavity, comprises a reaction space (reaction chamber) having a smaller volume, sometimes referred to as "reaction zone". The reaction zone of the tube reactor may optionally comprise appropriate temperature-controlling and/or pressure-controlling means, respectively, to control a predetermined temperature and/or pressure within. Suitable temperature-controlling and pressure-controlling means are known in the art.

A flow-through reactor, preferably a flow-through reactor with an elongate cavity, may have any appropriate length and diameter.

In a preferred embodiment, the flow-through reactor, preferably a flow-through reactor with an elongate cavity, has a length of at least 1 cm, 2 cm, 4 cm, 10 cm, or 100 cm.

In a further preferred embodiment, the flow-through reactor, preferably a flow-through reactor with an elongate cavity, has a diameter of at least 1 mm, 3 mm, 5 mm, or 10 mm.

The flow-through reactor, preferably the flow-through reactor with an elongate cavity, may be of any type and design known in the art, as long as the reactor is provided with a design allowing the mixing and reacting of the first and second liquid compositions under controlled conditions, preferably the simultaneous mixing and reacting of the first and second liquid compositions under controlled conditions. Preferably, the reactor design provides a reaction space ("reaction zone"), wherein the reaction between the at least one RNA and the at least one cationic or polycationic is completed under thoroughly controlled conditions. After completion of the reaction, preferably only the product liquid composition comprising the product nanoparticle comprising the at least one RNA and the at least one cationic or polycationic compound leaves the reaction zone of the reactor. Thereby, the method according to the present invention produces the product nanoparticle, which has uniform average particles size and polydispersity, reliably, under controlled conditions.

In a preferred embodiment, the flow-through reactor is a static mixer, which comprises at least one helical element. The first and second liquid compositions are introduced into one end of the reactor, and the mixing means comprising at least one helical element provides the turbulence, by which the two streams of reagent solutions are thoroughly mixed, and the product liquid composition leaving the reaction zone is recovered from the other end of the reactor. An example of a flow-through reactor, preferably a static mixer, comprising a mixing means comprising helical elements is shown in FIG. 6. It was found that the method of the invention may be advantageously carried out using a reactor comprising helical elements.

In a preferred embodiment, the first liquid composition and the second liquid composition are introduced into the reactor, preferably a static mixer as described herein, via separate openings (cf. FIG. 6). Alternatively, the first liquid composition and the second liquid composition may be unified (e.g. by a tee piece) prior to introduction into the reactor (cf. FIG. 10). Separate introduction of the first and the second composition is particularly preferred.

In another preferred embodiment of the invention, the turbulence for mixing is provided by introducing a stream of one liquid composition with an angle α into a stream of the other liquid composition (also referred to as "injector"). According to that embodiment, the reactor is preferably a static mixer, wherein one liquid composition selected from the first liquid composition and the second liquid composition flows through the reactor and the respective other liquid composition is injected into the liquid that flows through the reactor, wherein the respective other liquid composition is injected in the reactor or upstream of the reactor. Preferably, the reactor comprises an inlet port arranged at a side wall of the reactor, through which one of the reagent liquid compositions is introduced into an elongate cavity of the reactor, for example into the tube of a tube reactor, through which the other reagent liquid composition flows. The inlet port is preferably characterized by a diameter, which is inferior to the diameter of the reactor. According to a preferred embodiment, the ratio of the inlet port diameter to the reactor diameter is in a range from 1:2 to 1:20, preferably from 1:3 to 1:18, more preferably from 1:5 to 1:15. For example, the diameter of the inlet port may be in a range from 0.2 mm to 2 mm, more preferably from 0.5 to 1 mm. The angle α is defined as the angle, with which the two reagent streams meet in the reactor. For example, the angle α may be determined by the angle between the longitudinal direction of the main body of the reactor, wherein the first liquid composition flows, and the inlet port for the second liquid composition, or angle between the inlet ports for the two liquid compositions, or the like. Preferably, the angle α is from 10 to 90°, further preferred from 20 to 80°, and especially preferred about 30°.

An example of a reactor comprising an injector is shown in FIGS. 11 and 12. It was found that the method of the invention may be advantageously carried out using a reactor, preferably a tube reactor, comprising an injector.

Preferably, the first liquid composition and the second liquid compositions each are introduced into the at least one reactor, preferably into a flow-through reactor, more preferably into having an elongate cavity such as a tube reactor, with a flow rate of 10 ml/minute or more, preferably with a flow rate of 50 ml/minute or more, and more preferably with a flow rate of 125 ml/minute or more. Preferably, the total flow rate is 20 ml/minute or more, preferably 100 ml/minute or more, and more preferably 250 ml/minute or more, and more preferably 500 ml/minute or more, and more preferably 750 ml/minute or more, and most preferably 1000 ml/minute and more. It was found that the method of the invention provides excellent results with these flow rates.

The method of the present invention is a method for producing a liquid composition comprising a nanoparticle comprising at least one RNA and at least one cationic or polycationic compound.

It is assumed that the individual components of the nanoparticle are directly or indirectly bound to each other by means of electrostatic forces, hydrogen-bridges, or the like. A nanoparticle once formed is assumed to be a stable entity because of cooperative effects caused by the polymeric nature of the components.

Advantageously, the nanoparticles obtained by the method according to the present invention are characterised by having an uniform average particle size and particle size distribution, preferably as defined in the following.

In the context of the invention, a nanoparticle is a particle, preferably a solid particle which is characterised by having an average particle size and a particle size distribution. In the art, several methods to measure the average particle size of a nanoparticle are known.

In the context of the invention, the average size of the nanoparticles is measured by dynamic light scattering, whereby the particle size is represented as hydrodynamic diameter of a spherical particle. The so-measured average particle size is represented as Z-average in nm.

The measurements can readily be carried out using a suitable instrument. An example of a commercially available instrument is a Zetasizer Nano ZS, which is available from Malvern Instruments, Malvern, U.K. The measurement is preferably carried out at 25° C., preferably using a scattering angle of 173°. Further details of the measurement of the average particle size of a nanoparticle are described in Example 2.

In a preferred embodiment, the nanoparticle comprising at least one RNA and at least one cationic or polycationic compound obtained by the method according to the present invention has a particle size of 500 nm or less, more preferably from 50 to 500 nm, more preferably from 50 to 300 nm, more preferably from 50 to 200 nm, more preferably from 50 to 150 nm. Preferably, the nanoparticles comprising at least one RNA and at least one cationic or polycationic compound obtained by the method according to the present invention have an average particle size of 500 nm or less, more preferably from 50 to 500 nm, more preferably from 50 to 300 nm, more preferably from 50 to 200 nm, more preferably from 50 to 150 nm.

As a measure for the particle size distribution, the polydispersity and polydispersity index (PDI) can be used.

Polydispersity describes the width of a population distribution. It describes the degree of heterogeneity of a population. In this context, polydispersity represents the width of the particle size distribution of the nanoparticles present in a liquid composition, particularly the width of the particle size distribution of the product RNA-comprising nanoparticles.

The polydispersity index (PDI) is a dimensionless measure of the broadness of the size distribution in nanoparticle samples. Polydispersity index values below 0.1 indicate a monomodal distribution, while a polydispersity index over 0.5 indicates a broad distribution of particle sizes. Analytical instruments and methods for the calculation of these parameters used for size measurements have been described (e.g. Zetasizer Nano Series; User Manual MAN0314 Issuer 1.1 February 2004).

The measurements of the PDI can readily be carried out using a suitable instrument. An example of a commercially available instrument is a Zetasizer Nano ZS, which is available from Malvern Instruments, Malvern, U.K. Further details of the measurement of the PDI of a nanoparticle are described in Example 2.

The polydispersity index (PDI), sometimes referred to as heterogeneity index, or simply dispersity (Đ), is a measure of the distribution of molecular mass in a given nanoparticle sample. The PDI calculated is the weight-average molecular weight (Mw) divided by the number-average molecular weight (Mn):

$$PDI=Mw/Mn,$$

where Mw is the weight average molecular weight and Mn is the number average molecular weight. The PDI indicates the distribution of individual molecular masses in a batch of nanoparticles.

Preferably, the nanoparticles comprising at least one RNA and at least one cationic or polycationic compound have a polydispersity index of from 0.05 to 0.50, preferably of from 0.05 to 0.40, and more preferably of from 0.10 to 0.30.

This represents a monomodal to narrow particle size distribution, which is advantageously obtained in RNA-comprising nanoparticles with the method according to the present invention.

In the context of the present invention, particularly preferred are RNA-comprising nanoparticles with a PDI of 0.5 or below, and more preferred with a PDI of 0.4 or below, and most preferred with a PDI of 0.3 or below.

Preferably, the product liquid composition comprising a nanoparticle comprising at least one RNA and at least one cationic or polycationic compound obtained by the method of the invention is a dispersion of nanoparticles comprising at least one RNA and at least one cationic or polycationic compound, preferably a stable colloidal dispersion in water.

A stable colloidal dispersion is a dispersion of nanoparticles, which does not deteriorate with time, even after long-time storage under appropriate conditions.

Advantageously, the product liquid composition comprising an RNA-comprising nanoparticle obtained according to the method of the present invention comprises uniform RNA-comprising nanoparticles in high quality and excellent yields, without comprising significant amounts of unwanted side products, which lead to turbidity (precipitates) in the product compositions and the ultimate deterioration thereof. In particular, the method according to the present invention allows to produce RNA-comprising nanoparticles in a quality sufficient and reliable for pharmaceutical applications, even in a large scale production. The method of the invention further allows obtaining excellent yields.

In order to assess the quality of the product liquid composition comprising the RNA-comprising nanoparticle obtained by the method according to the present invention, the composition is preferably inspected visually, more preferably by using image processing techniques. Product compositions having the desired quality are typically clear. An inferior quality of the product composition is visible, for example, as turbidity within the composition, wherein increasing turbidity is correlated with decreasing product quality and stability, eventually resulting in the formation of precipitates.

In order to obtain a numerical value for assessing the product quality by means of its clarity, the absorption of the product liquid composition can also be measured. Preferably, the absorption of the product liquid composition comprising the compound comprising at least one RNA and at least one cationic or polycationic compound is measured directly after the production thereof. This measurement of absorption may be preferably and advantageously carried out in-line in a continuous production process.

In the context of the invention, absorption measurements are carried out at 350 nm. Further details of the measurement of the absorption at 350 nm of a RNA-comprising nanoparticle-containing product composition are described in Example 2.

Preferably, the product liquid composition has an absorption at 350 nm of 0.5 or less, of 0.4 or less, of 0.3 or less, more preferably of 0.2 or less and most preferably of 0.15 or less.

Additionally or alternatively, the quality of the product liquid composition comprising the compound comprising at least one RNA and at least one cationic or polycationic compound is preferably assessed by measuring its turbidity. For example, the turbidity may be measured at 860 nm with a detecting angle of 90° using commercially available instruments and methods known in the art. An example for a commercially available instrument is a NEPHLA turbidimeter, available from Dr. Lange, Düsseldorf, Germany. The system is calibrated with formazin as standard and the results were given in formazin nephelometric units (FNU). This method and other methods useful for measuring turbidity/clarity are known in the art and are e.g. described in EUROPEAN PHARMACOPOEIA 5.0, 2.2.1. Clarity and degree of opalescence of liquids and ISO 7027:1999-Water quality.

Further details of the measurement of the turbidity (FNU) of a RNA-comprising nanoparticle-containing product composition are described in Example 2.

Preferably, the product liquid composition comprising the compound comprising at least one RNA and at least one cationic or polycationic compound has a turbidity of 100 FNU or less.

In a preferred embodiment, the method according to the invention further comprises a step (e) of isolating or concentrating the compound and/or nanoparticles comprising at least one RNA and at least one cationic or polycationic compound from the product liquid composition comprising the nanoparticle comprising at least one RNA and at least one cationic or polycationic compound.

Suitable methods for isolating the nanoparticle from the product liquid composition are lyophilisation, spray-drying, spray-freeze drying, or the like.

Preferably, step (e) comprises a drying step selected from the group consisting of lyophilisation, spray-drying, or spray-freeze drying.

In a further aspect, the present invention provides a liquid composition comprising a nanoparticle comprising at least one RNA and at least one cationic or polycationic compound which is obtainable by the method according to the present invention, and/or the nanoparticle comprising at least one RNA and at least one cationic or polycationic compound which is obtainable and preferably isolated by the method according to the present invention.

In yet another aspect, the present invention concerns the use of the inventive method in the manufacture of a medicament or a vaccine, preferably a medicament or a vaccine for use in the treatment or prophylaxis of a disorder or a disease. In the context of the present invention, the disorder or the disease is preferably selected from the group consisting of cancer or tumor diseases, infectious diseases, preferably viral, bacterial or protozoological infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases and neuronal diseases.

The present invention further relates to the medical use of the liquid composition comprising the nanoparticle comprising at least one RNA and at least one cationic or polycationic compound, which is obtainable by the method according to the present invention. Moreover, the present invention relates to the medical use of the nanoparticle comprising at least one RNA and at least one cationic or polycationic compound, which is obtainable by the the method according to the present invention. In a preferred embodiment, the invention provides the liquid composition comprising the nanoparticle comprising at least one RNA and at least one cationic or polycationic compound, which is obtainable by the method according to the present invention or the nanoparticle comprising at least one RNA and at least one cationic or polycationic compound, which is obtainable by the method according to the present invention, for use in the treatment or prophylaxis of a disease or disorder as defined herein.

Furthermore, the present invention relates to a method of treatment, wherein the method comprises administering to a subject in need thereof the liquid composition comprising the nanoparticle comprising at least one RNA and at least one cationic or polycationic compound, or the nanoparticle comprising at least one RNA and at least one cationic or polycationic compound, which are obtainable by the method according to the present invention. Preferably, the liquid composition or the nanoparticle is administered to a subject via any suitable administration route, preferably in a safe and effective amount.

Preferably and advantageously, the nanoparticle comprising at least one RNA and at least one cationic or polycationic compound, or the product liquid composition comprising the nanoparticle comprising at least one RNA and at least one cationic or polycationic compound are for use in a pharmaceutical composition suitable for RNA therapy.

In a further aspect, the present invention provides a pharmaceutical composition comprising the nanoparticle comprising at least one RNA and at least one cationic or polycationic compound, or the product liquid composition comprising the nanoparticle comprising at least one RNA and at least one cationic or polycationic compound, obtainable by the method according to the present invention. Preferably, the pharmaceutical composition is for use in the treatment or prophylaxis of a disease or disorder as defined herein.

Furthermore, the invention is preferably described by the following items:

1. A method for producing a liquid composition comprising a nanoparticle comprising at least one long-chain RNA and at least one cationic or polycationic compound,
   wherein the method comprises the steps of:
   (a) providing a first liquid composition comprising at least one RNA,
   (b) providing a second liquid composition comprising at least one cationic or polycationic compound,
   (c) introducing the first liquid composition and the second liquid composition into at least one reactor, wherein the first liquid composition and the second liquid composition are mixed with a blend time of 5 seconds or less, and
   (d) recovering the product liquid composition comprising the nanoparticle comprising the at least one RNA and the at least one cationic or polycationic compound from the reactor.

2. The method according to item 1, wherein the at least one RNA is selected from the group consisting of a long-chain RNA, a coding RNA, a non-coding RNA, a single-stranded RNA, a double stranded RNA, a linear RNA, a circular RNA (circRNA), a messenger RNA (mRNA), an RNA oligonucleotide, an siRNA, an miRNA, an shRNA, an antisense RNA, a riboswitch, an immunostimulating RNA (isRNA), a ribozyme, an aptamer, a ribosomal RNA (rRNA), a transfer RNA (tRNA), a self-replicating RNA (replicon RNA), a CRISPR/Cas9 guide RNA, a small nuclear RNA (snRNA), a small nucleolar RNA (snoRNA), Piwi-interacting RNA (piRNA), a retroviral RNA, or a viral RNA (vRNA).

3. The method according to item 1 or 2, wherein the at least one RNA is a long-chain RNA comprising from 100 to 50000 nucleotides, preferably from 200 to 15000 nucleotides, more preferably from 300 to 10000 nucleotides, and most preferably from 400 to 7000 nucleotides.

4. The method according to any one of items 1 to 3, wherein the at least one RNA is not an siRNA.

5. The method according to any one of the preceding items, wherein the at least one RNA is an mRNA.

6. The method according to any one of the preceding items, wherein the nanoparticle comprising at least one RNA and at least one cationic or polycationic compound has a particle size of 300 nm or less, preferably of from 50 to 200 nm, and more preferably from 50 to 150 nm.

7. The method according to any one of the preceding items, wherein the nanoparticle comprising at least one RNA and at least one cationic or polycationic compound has a polydispersity index in a range from 0.05 to 0.50, preferably of from 0.05 to 0.40, and more preferably of from 0.05 to 0.3.

8. The method according to any one of the preceding items, wherein the product liquid composition comprising the nanoparticle comprising at least one RNA and at least one cationic or polycationic compound is a dispersion of the nanoparticle comprising at least one RNA and at least one cationic or polycationic compound, preferably a stable colloidal dispersion in water.

9. The method according to any one of the preceding items, wherein the product liquid composition comprising the nanoparticle comprising at least one RNA and at least one cationic or polycationic compound has absorption at 350 nm of 0.5 or less.

10. The method according to any one of the preceding items, wherein the product liquid composition comprising the nanoparticle comprising at least one RNA and at least one cationic or polycationic compound has a turbidity of 100 FNU or less.

11. The method according to any one of the preceding items, wherein the first liquid composition comprises RNA in a concentration of from 0.1 to 20 g/L, preferably from 0.5 to 10 g/L, and more preferably from 0.5 to 7 g/L.

12. The method according to any one of the preceding items, wherein the at least one cationic or polycationic compound is selected from the group consisting of a cationic or polycationic peptide, a cationic or polycationic protein, a cationic or polycationic polyamino acid, a cationic or polycationic carbohydrate, a cationic or polycationic synthetic polymer, a cationic or polycationic small synthetic organic molecule, an inorganic multivalent cation, a cationic or polycationic lipid, a cationic or polycationic polyamine compound, and a cationic or polycationic polyimine compound.

13. The method according to any one of the preceding items, wherein the at least one cationic or polycationic compound is a cationic or polycationic peptide or protein.

14. The method according to any one of the preceding items, wherein the at least one cationic or polycationic compound is selected from the group consisting of protamine, nucleoline, spermine or spermidine, poly-L-lysine (PLL), basic polypeptides, poly-arginine, oligoarginines, cell penetrating peptides (CPPs), HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from Drosophila antennapedia), pAntp, plsl, FGF, Lactoferrin, Transportan, Buforin-2, Bac715-24, SynB, SynB(1), pVEC, hCT-derived peptides, SAP, and histones.

15. The method according to any one of the preceding items, wherein the second liquid composition comprises a cationic or polycationic compound in a concentration in a range from 0.05 to 10.00 g/L, preferably from 0.10 to 5.00 g/L or, more preferably, from 0.10 to 1.00 g/L.

16. The method according to any one of the preceding items, wherein the first liquid composition and/or the second liquid composition further comprise at least one compound selected from a salt or a lyoprotectant.

17. The method according to any one of the preceding items, wherein the first liquid composition and/or the second liquid composition comprise at least one salt selected from the group consisting of NaCl, KCl, LiCl, $MgCl_2$, NaI, NaBr, $Na_2CO_3$, $NaHCO_3$, $Na_2SO_4$, $Na_3PO_4$, KI, KBr, $K_2CO_3$, $KHCO_3$, $K_3PO_4$, $K_2SO_4$, $CaCl_2$, $CaI_2$, $CaBr_2$, $CaCO_3$, $CaSO_4$, $Ca(OH)_2$, and $Ca_3(PO_4)_2$.

18. The method according to any one of the preceding items, wherein the first liquid composition and/or the second liquid composition comprise at least one cation selected from the group consisting of $Na^+$, $K^+$, $Li^+$, $Mg^{2+}$, $Ca^{2+}$, and $Ba^{2+}$ and/or at least one anion selected from the group consisting of $Cl^-$, $CO_3^{2-}$, $PO_4^{3-}$ and $SO_4^{2-}$.

19. The method according to item 17, wherein the concentration of the cation in the first liquid composition and/or the second liquid composition is up to 50 mM, preferably of from 0.001 to 50 mM, more preferably from 3 to 30 mM.

20. The method according to any one of items 18 or 19, wherein the ratio of cation to RNA in the first liquid composition is from 3 to 30 mmol cation/g RNA, preferably from 4 to 23 mmol cation/g RNA, and most preferably from 5 to 10 mmol cation/g RNA.

21. The method according to any one of items 18 to 20, wherein the concentration of the anion in the first liquid composition and/or second liquid composition is 23 mM or less, more preferably from 1.0 to 23.0 mM, and especially preferred from 1.0 to 10.0 mM.

22. The method according to any one of the preceding items, wherein the lyoprotectant is selected from the group consisting of sucrose, mannose, trehalose, mannitol, polyvinylpyrrolidone, glucose, fructose, Ficoll 70.

23. The method according to item 22, wherein the concentration of the lyoprotectant in the first liquid composition and/or the second liquid composition is in a range from 0.01% (w/w) to 40% (w/w), preferably from 1% (w/w) to 20% (w/w).

24. The method according to any one of the preceding items, wherein the first liquid composition and/or the second liquid composition comprises water.

25. The method according to any one of the preceding items, wherein the blend time is experimentally determined.

26. The method according to any one of the preceding items, wherein the blend time is determined by using a method selected from a colorimetric method, a method based on conductivity measurements, and a chemical method.

27. The method according to any one of the preceding items, wherein the blend time is determined by using a chemical method on the basis of an acid-base-type reaction using colorimetric detection.

28. The method according to any one of items 1 to 24, wherein the blend time is determined by computer simulations using computational fluid dynamics (CFD).

29. The method according to any one of the preceding items, wherein the first liquid composition and the second liquid composition are added to the at least one reactor so that the at least one cationic or polycationic compound and the at least one RNA are present in the reactor with an N/P-ratio in a range from 0.1 to 10, preferably from 0.3 to 4, and even more preferably from 0.3 to 0.9.

30. The method according to any one of the preceding items, wherein the at least one reactor has a volume in a range from 1 ml to 10 l, preferably from 1 ml to 5 l, more preferably from 1 ml to 500 ml.

31. The method according to any one of the preceding items, wherein the at least one reactor comprises at least one mixing means.

32. The method according to item 31, wherein the at least one mixing means comprises at least one dynamic mixing means and/or at least one static mixing means.

33. The method according to any one of the preceding items, wherein the reactor is a dynamic mixer comprising at least one dynamic mixing means.

34. The method according to any one of the preceding items, wherein the first liquid composition and the second liquid composition are mixed without shaking and/or agitating the at least one reactor or the first and second liquid compositions, respectively.

35. The method according to any one of items 32 to 34, wherein the at least one dynamic mixing means comprises at least one stirring means.

36. The method according to item 35, wherein the at least one stirring means can be operated at a stirring rate of at least 300 rpm, preferably of at least 500 rpm, and more preferably of at least 1000 rpm.

37. The method according to any one of items 1 to 33, wherein the reactor is a static mixer.

38. The method according to item 37, wherein the static mixer comprises at least one static mixing means, which comprises at least one static element, preferably at least one static element positioned within a flow path of the first liquid composition and/or the second liquid composition.

39. The method according to item 37 or 38, wherein the reactor comprises an elongate cavity, through which the first liquid composition and/or the second liquid composition flow.

40. The method according to item 39, wherein the elongate cavity has the shape of a cylinder, a tube, a pipe, a capillary or a hose.

41. The method according to any one of items 37 to 40, wherein one liquid composition selected from the first liquid composition and the second liquid composition flows through the reactor and the respective other liquid composition is injected into the liquid that flows through the reactor, wherein the respective other liquid composition is injected in the reactor or upstream of the reactor.

42. The method according to any one of the preceding items, wherein the method is conducted continuously or discontinuously.

43. The method according to any one of the preceding items, wherein the first liquid composition and/or the second liquid composition are introduced into the at least one reactor with a flow rate of 0.1 ml/minute ore more, preferably 50 ml/minute or more, more preferably 100 ml/minute or more, more preferably 150 ml/minute or more, more preferably 300 ml/minute or more, more preferably 800 ml or more, most preferably in a range of 100-800 ml/minute.

44. The method according to any one of the preceding items, wherein the first liquid composition and the second liquid composition are successively introduced into the at least one reactor.

45. The method according to any one of items 1 to 43, wherein the first liquid composition and the second liquid composition are concurrently introduced into the at least one reactor, preferably under controlled conditions e.g. constant flow rates.

46. The method according to item 45, wherein the first liquid composition and the second liquid composition are introduced into the at least one reactor with the same flow rate.

47. The method according to any one of the preceding items, further comprising a step (e) of isolating or concentrating the nanoparticle comprising at least one RNA and at least one cationic or polycationic compound from the product liquid composition comprising the nanoparticle comprising at least one RNA and at least one cationic or polycationic compound.

48. The method according to item 47, wherein step (e) comprises a drying step, preferably a drying step selected from the group consisting of lyophilisation, spray-drying, or freeze-spray drying.

49. The method according to any one of the preceding items, wherein the nanoparticle comprising at least one RNA and at least one cationic or polycationic compound, or the product liquid composition comprising the nanoparticle comprising at least one RNA and at least one cationic or polycationic compound are for use in a pharmaceutical composition.

50. A liquid composition comprising the nanoparticle comprising at least one RNA and at least one cationic or polycationic compound, which are obtainable by the method according to any one of items 1 to 47.

51. A nanoparticle comprising at least one RNA and at least one cationic or polycationic compound, obtainable by the method according to items 47 or 48.

52. Use of the method according to any one of items 1 to 49 in the manufacture and/or preparation of a medicament or a vaccine, preferably a medicament or a vaccine for use in the treatment or prophylaxis of a disorder or a disease.

53. The use according to item 52, wherein the disorder or the disease is selected from the group consisting of cancer or tumor diseases, infectious diseases, preferably viral, bacterial or protozoological infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases and neuronal diseases.

54. A pharmaceutical composition comprising the liquid composition comprising the nanoparticle comprising at least one RNA and at least one cationic or polycationic compound according to item 50, and/or the nanoparticle comprising at least one RNA and at least one cationic or polycationic compound according to item 51.

55. The pharmaceutical composition according to item 54, wherein the pharmaceutical composition is for use in the treatment or prophylaxis of a disorder or a disease.

56. The pharmaceutical composition for use according to item 55, wherein the disorder or the disease is selected from cancer or tumor diseases, infectious diseases, preferably viral, bacterial or protozoological infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases and neuronal diseases.

BRIEF DESCRIPTION OF THE FIGURES

The figures shown in the following are merely illustrative and shall describe the present invention in a further way. These figures shall not be construed to limit the present invention thereto.

FIG. 1: G/C-enriched mRNA sequence R2564 coding for the hemagglutinin (HA) protein of influenza A virus (A/Netherlands/602/2009(H1N1)), corresponding to SEQ ID NO: 1.

The reference signs do only apply to that particular figure and are not used continuously; the reference signs shall not be used, applied or translated to other figures and drawings.

Figure 4:
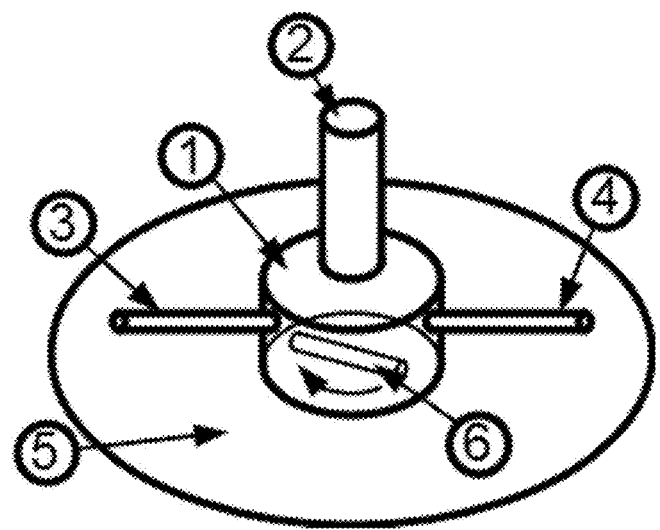

FIG. 4: Schematic view of a continuously operating stirred reactor (Reactor III, as prepared according to Example 3.3 described below). (1) Cylindrical reactor chamber; (2) Inlet port; (3) Inlet port; (4) Inlet port; (5) Magnetic stirrer; (6) Stir bar. The reference signs do only apply to that particular figure and are not used continuously; the reference signs shall not be used, applied or translated to other figures and drawings.

Figure 5:
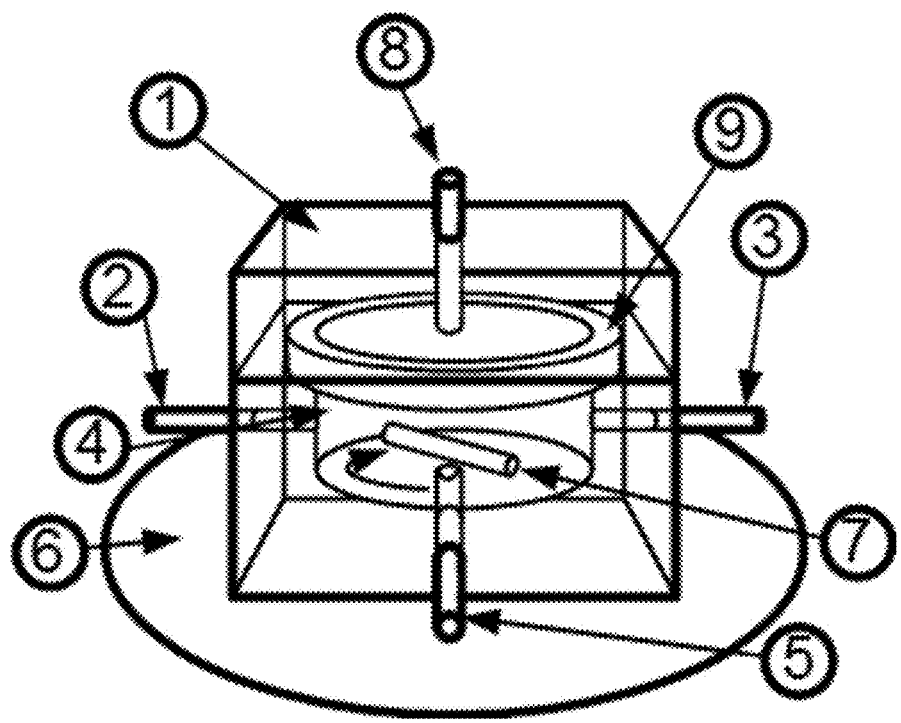

FIG. 5: Schematic view of a continuously operating stirred reactor (Reactor V, cf. Example 3.5 described below). (1) Stainless steel reactor body; (2) Inlet connection for silicone hose tube (addition of the RNA solution); (3) Inlet connection for silicone hose tube (addition of the cationic or polycationic compound solution, e.g. protamine solution); (4) Reactor chamber; (5) Outlet connection for silicone hose tube, (6) Magnetic stirrer; (7) Stir bar; (8) Ventilation connection (for bubble-free filling of reactor, closed under operation); (9) Seal ring. A technical drawing of that reactor type is provided in FIG. 13. The reference signs do only apply to that particular figure and are not used continuously; the reference signs shall not be used, applied or translated to other figures and drawings.

Figure 6:
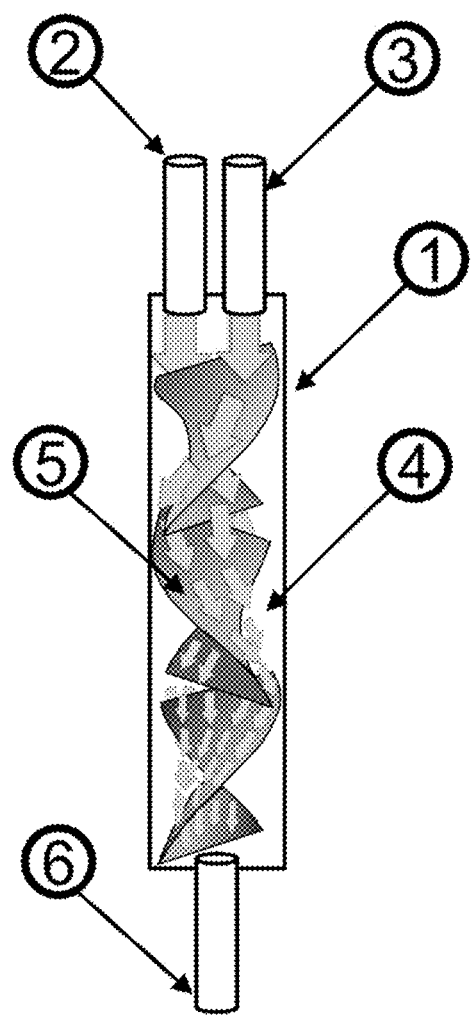

FIG. 6: Schematic view of a continuously operating reactor (Reactor VI, cf. Example 3.6 described below). (1) Reactor comprising static mixing elements; (2) Inlet connection for silicone hose tube (addition of the RNA solution); (3) Inlet connection for silicone hose tube (addition of the cationic or polycationic compound solution, e.g. protamine solution); (4) Reactor chamber; (5) Staticmixing elements; (6) Outlet connection for silicone tube. Theeference signs do only apply to that particular figure and are not used continuously; the reference signs shall not be used, applied or translated to other figures and drawings.

Figure 7:
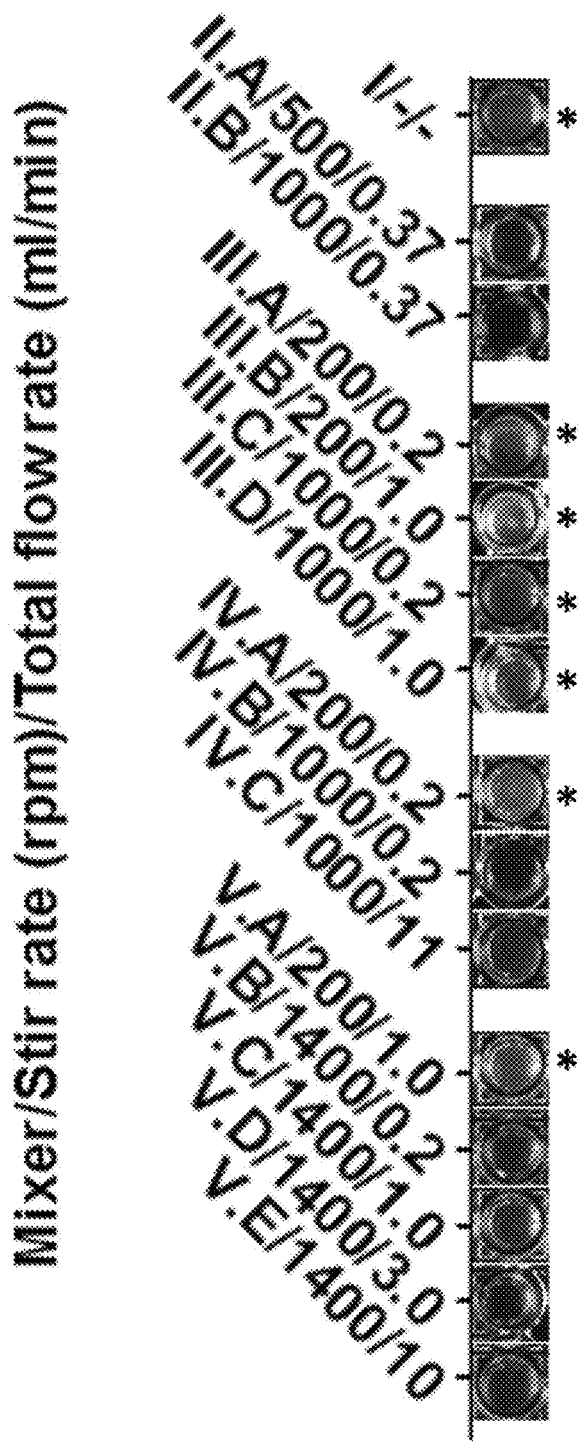

FIG. 7: Photograph of product dispersions of RNA-protamine nanoparticles in 96-well microtiter plates produced in Examples 4 to 8 (cf. Example 2.2). Undesired precipitates are visible in some reactions (grey colour; indicated by asterisks). These precipitates were formed in experiments where the blend time was 8 seconds or longer (cf. Table 5).

Figure 8:
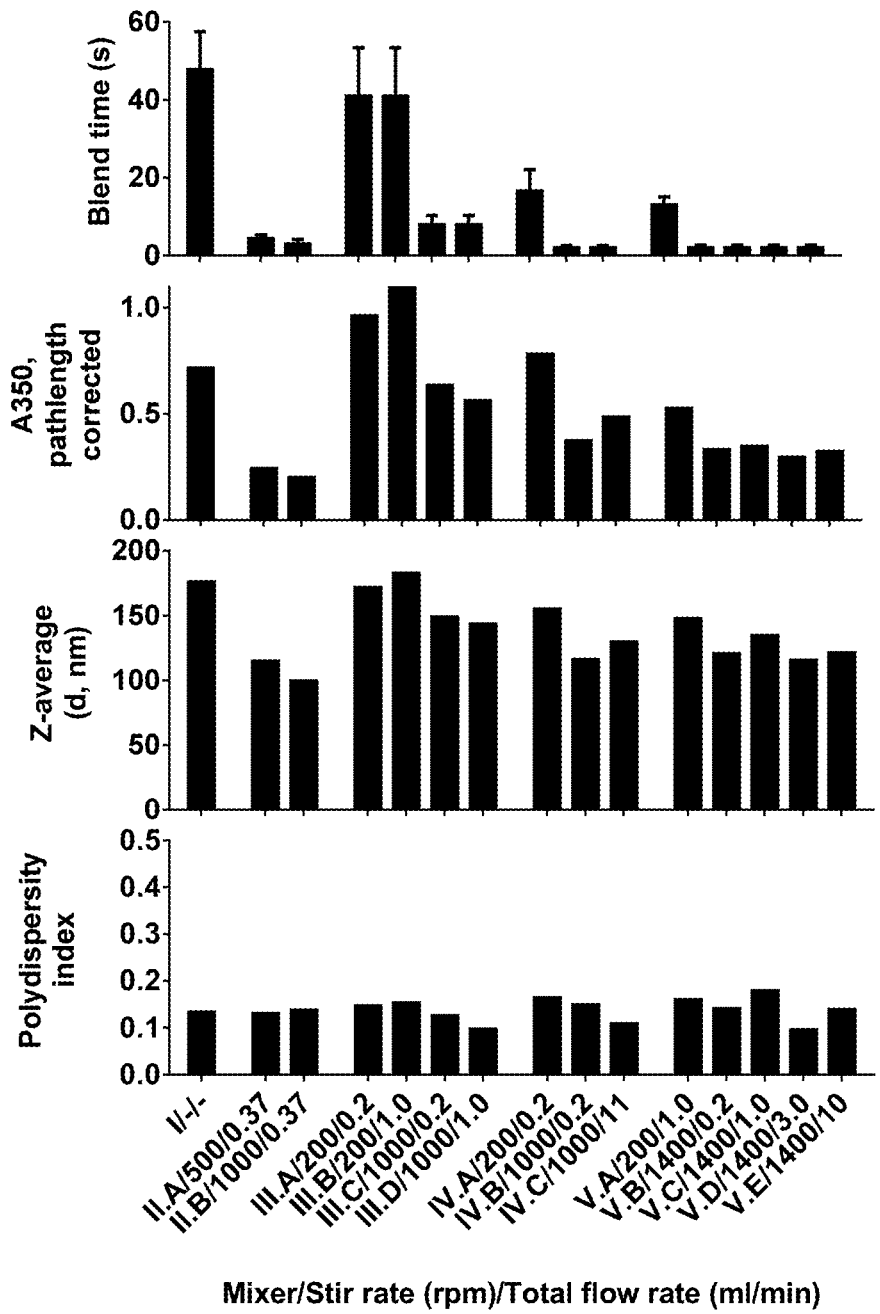

FIG. 8: Summary of blend time of reactors (cf. Example 3), and clarity/turbidity, particle size and polydispersity of RNA-protamine nanoparticles produced in Examples 4 to 8 (cf. Example 2): Effect of reactor design, stir rate and total flow rate on the blend time (top panel, average of 5 measurements with standard deviation), the absorption at 350 nm (A350, second panel), on particle size (Z-average, third panel) and the particle polydispersity (fourth panel).

Figure 9:
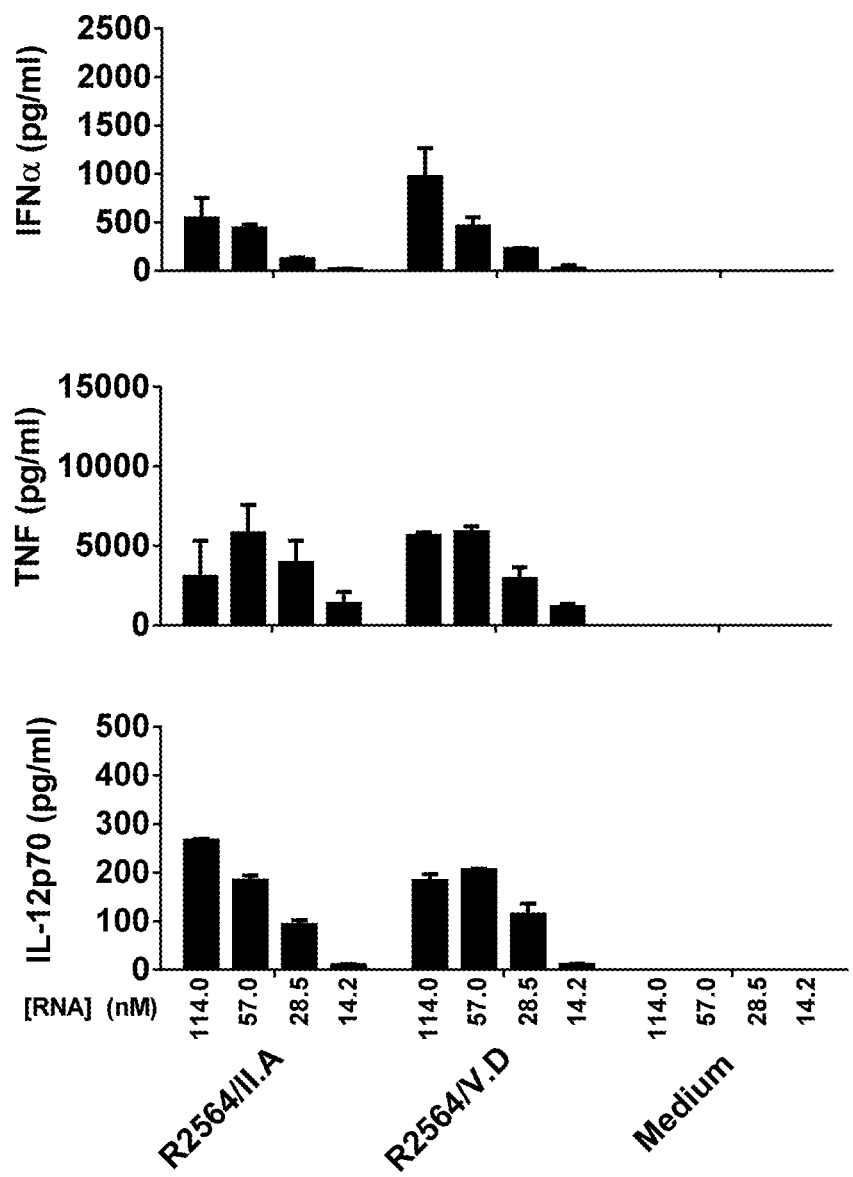

FIG. 9: Immunostimulation by RNA-comprising nanoparticles. The induction of cytokines in peripheral blood mononuclear cells (PBMCs) by RNA/protamine nanoparticles, which were produced in Examples 5.1 or 8.4, is shown (cf. Example 10).

Figure 10:
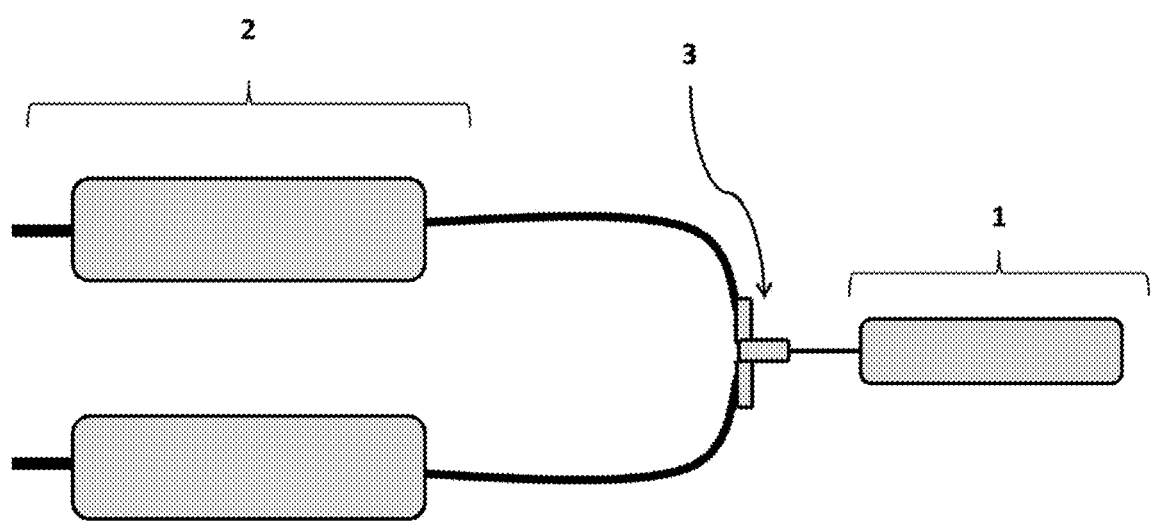

FIG. 10: Schematic view of a continuously operating reactor (Reactor VI, cf. Example 3.6 described below). (1) Reactor comprising static mixing elements; (2) pumps for reagent solutions; (3) T-piece adapter. The reference signs do only apply to that particular figure and are not used continuously; the reference signs shall not be used, applied or translated to other figures and drawings.

Figure 11:
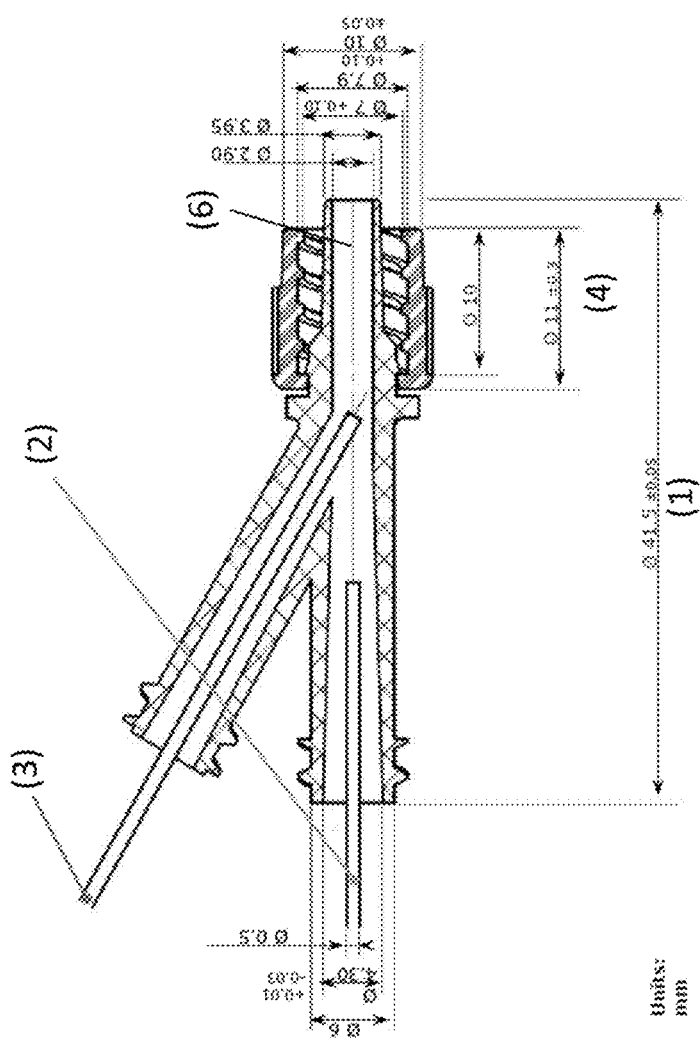

FIG. 11: Schematic view of a continuously operating reactor (Reactor VII, cf. Example 3.7 described below). (1) Reactor comprising injector-type mixing means; (2) Inlet connection for silicone tube (addition of the RNA solution); (3) Inlet connection for silicone tube (addition of the cationic or polycationic compound solution, e.g. protamine solution); (4) Reaction zone; (5) injection angle α; (6) Outlet connection for silicone tube. The reference signs are in brackets. The reference signs do only apply to that particular figure and are not used continuously; the reference signs shall not be used, applied or translated to other figures and drawings. Other indicated numbers represent distances in mm.

Figure 12:
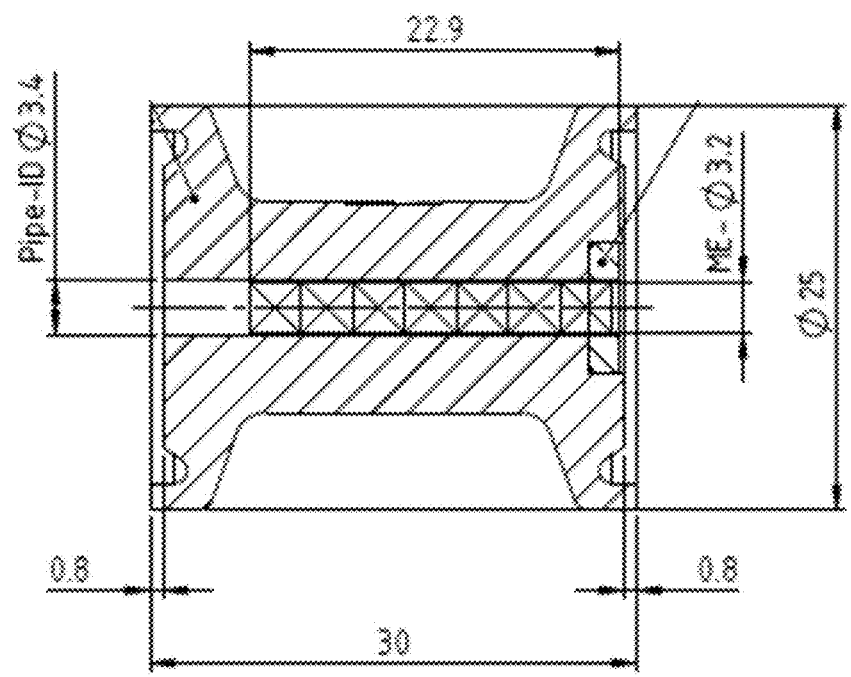

FIG. 12: Schematic view of the continuously operating injector mixer (Reactor VII) used in Example 3.7. The injector mixer mixer consisted of a stainless steel housing with an inner diameter of 3.4 mm and a length of 30 mm. Inserted was a Sulzer SMX static mixer DN3 with a length of 22 mm and a diameter of 3.2 mm made of stainless steel.

Figure 13:
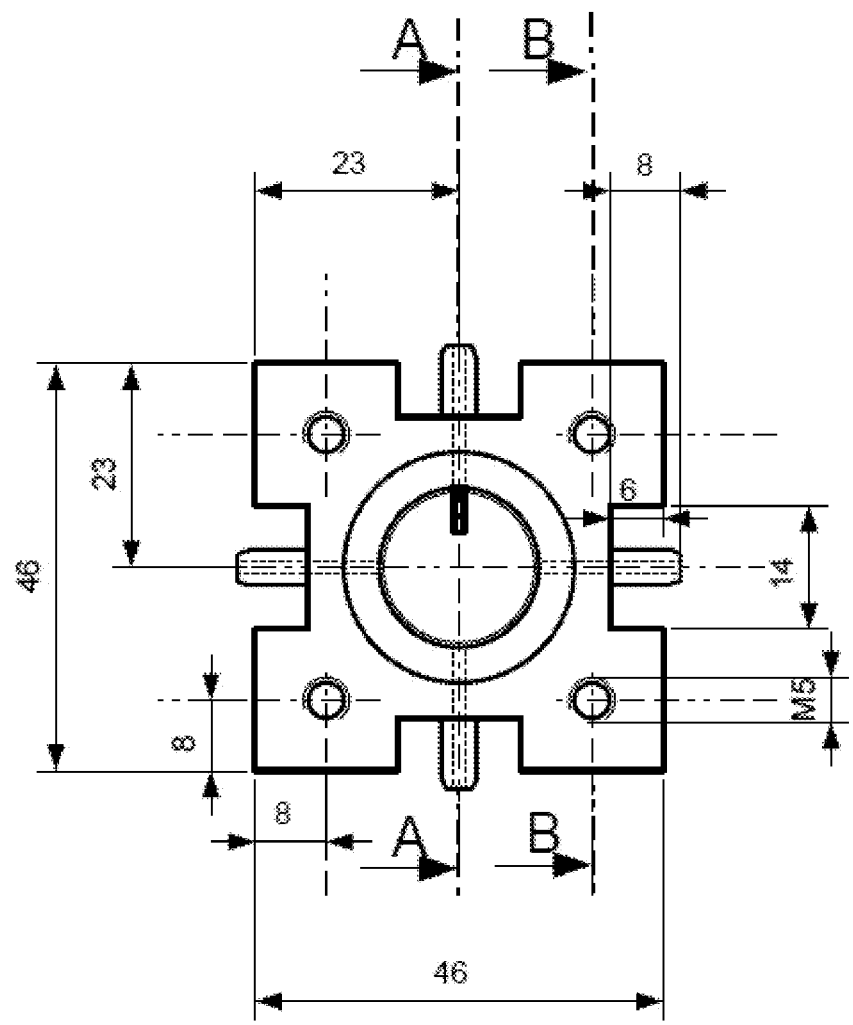

FIG. 13: Technical drawing of a schematic view of a continuously operating stirred reactor (Reactor V, cf. FIG. 5 and Example 3.5 as described below). Indicated numbers represent distances in mm and do not refer to reference signs.

Figure 14:
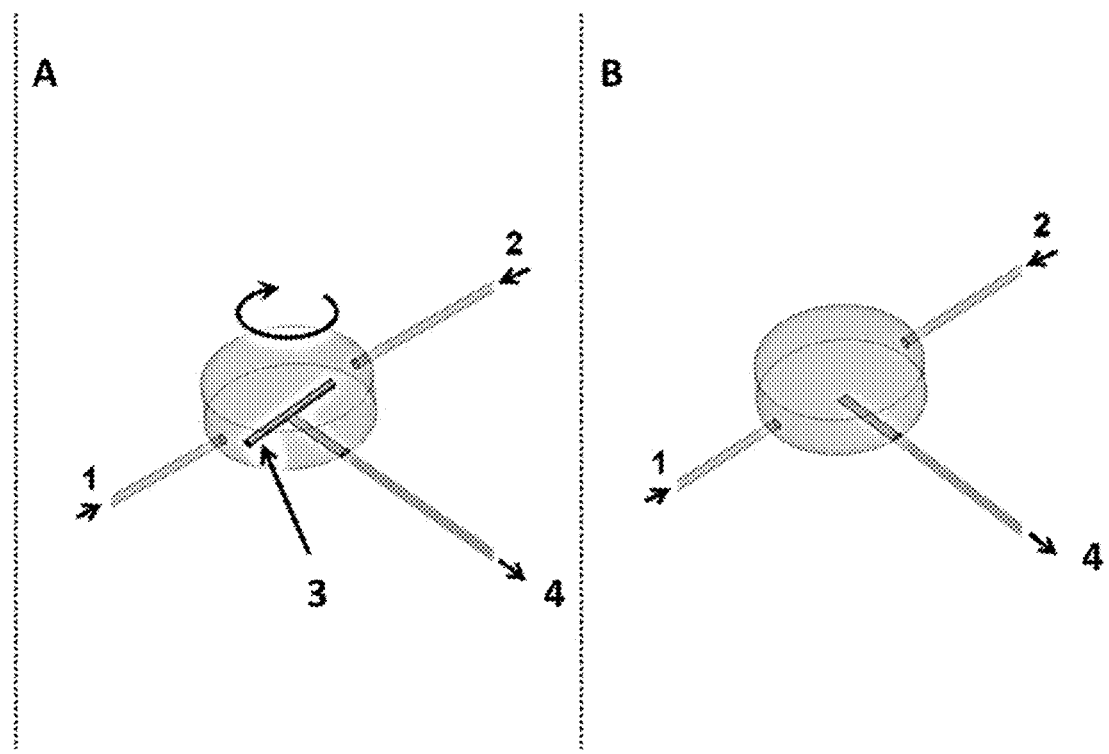

FIG. 14: Schematic simplified reactor models used for computational fluid dynamics (CFD) analysis. In panel (A) a model of reactor type V (continuous reactor with stirring means) is shown and in panel (B) a reactor type V.1 (continuous reactor without stirring means) is shown (see Example 3). Reference signs: (1) inlet port (addition of RNA containing solution); (2) inlet port (addition of the cationic or polycationic compound solution); (3) stirring means (magnetic stirrer); (4) outlet port. Further details of the CFD analysis are provided in Example 12. The reference signs do only apply to that particular figure and are not used continuously; the reference signs shall not be used and applied or translated to other figures and drawings.

Figure 15:
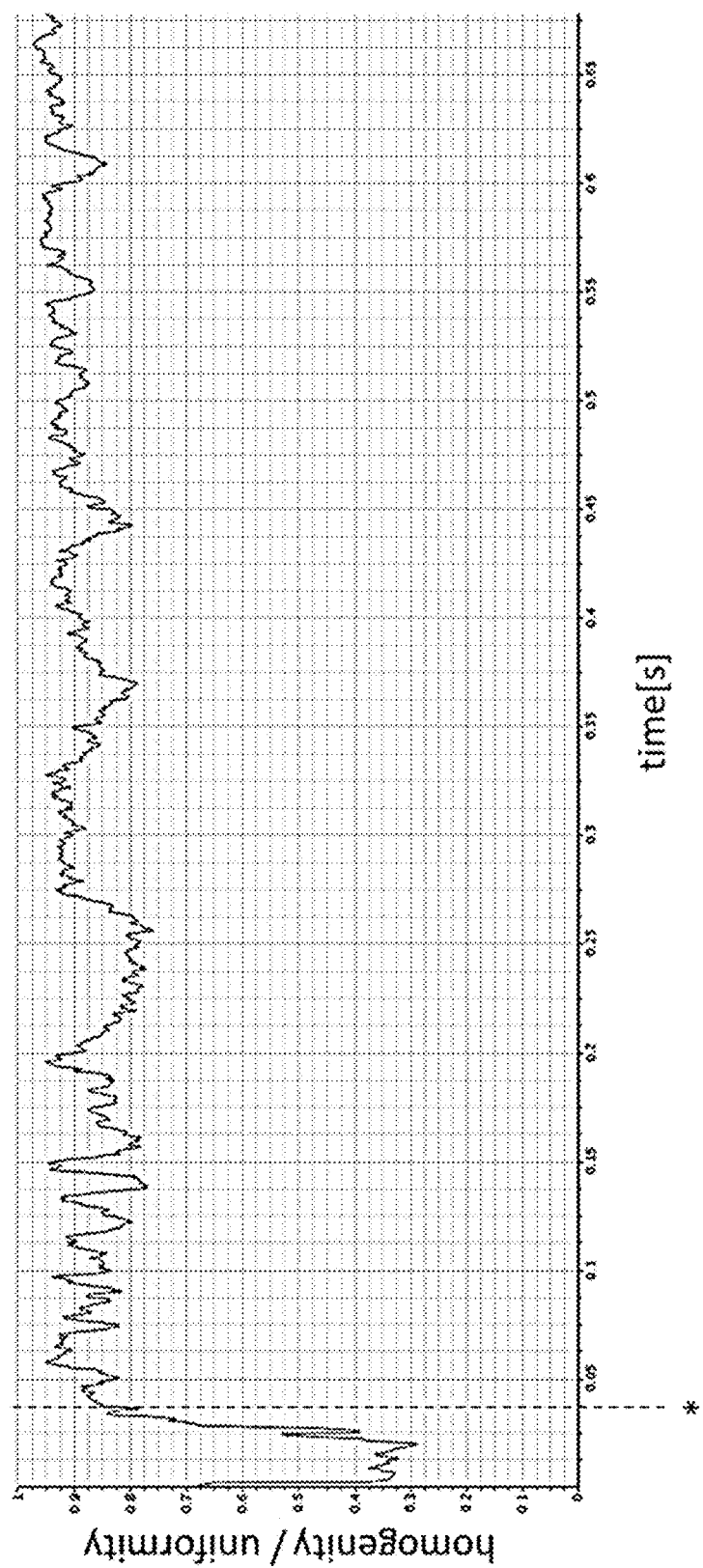

FIG. 15: Exemplary result of a CFD analysis, performed according to Example 12. The graph shows the homogeneity/uniformity obtained at the outlet port after a certain time period. The dashed line (asterisk) indicates the blend time of the mixing process (reactor V, 160 ml/min, 1400 rpm) required in order to reach a given homogeneity, in the context of the invention, to reach a homogeneity level of 0.8 or 80%. Further details of the CFD analysis are provided in Example 12.

Figure 16:
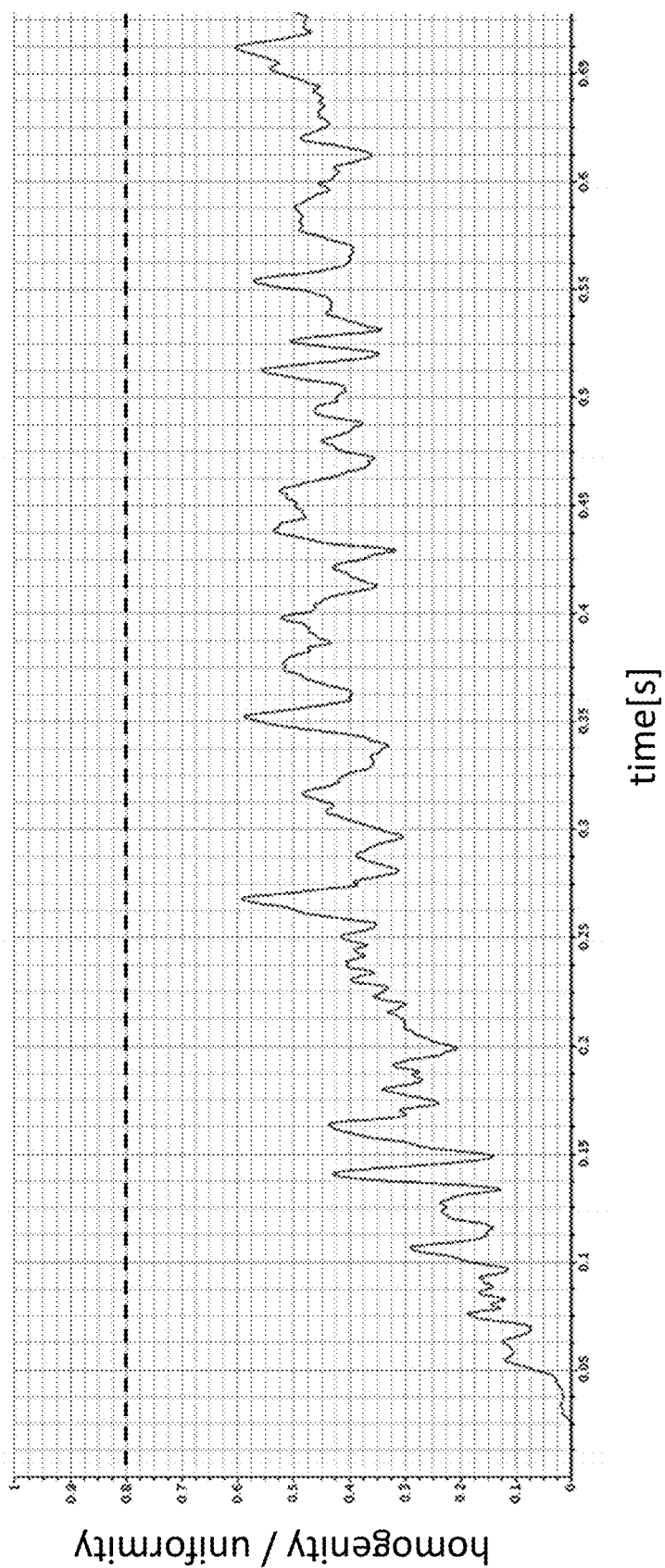

FIG. 16: Exemplary result of a CFD analysis, performed according to Example 12. The graph shows the homogeneity/uniformity obtained at the outlet port after a certain time period. The figure shows that a sufficient homogeneity of the mixture could not be obtained in the simulated time interval for reactor V.1 at 10 ml/min flow rate. In the context of the invention, a homogeneity level of 0.8 or 80% is desired, indicated by a horizontal line. Therefore, a blend time could not be determined. Further details of the CFD analysis are provided in Example 12.

EXAMPLES

The Examples shown in the following are merely illustrative and shall describe the present invention in a further way. These Examples shall not be construed to limit the present invention thereto.

In the following examples according to the present invention and comparative examples, the method according to the present invention is carried out in some exemplary reactors, which are described in detail in Example 3 using standardised model reagent compositions of RNA and cationic or polycationic compound, respectively, which are described in detail in Example 1, and the respective products are characterised according methods, which are described in detail in Example 2.

Example 1—Reagents Used in all Examples and Reference Examples 1.1 Preparation of the RNA Solution 1.1.1 Preparation of DNA and mRNA Constructs For the model reaction used most Examples and Reference Examples described in the following, a DNA sequence encoding the hemagglutinin (HA) protein of influenza A virus (A/Netherlands/602/2009(H1N1)) was prepared and used for subsequent in vitro transcription reactions.

In this embodiment, the DNA sequence encoding the above-mentioned mRNA was prepared.

The construct R2564 (Influenza HA encoding mRNA: SEQ ID NO: 1, shown in FIG. 1) was prepared by introducing a 5'-TOP-UTR derived from the ribosomal protein 32L4, modifying the wild type coding sequence by introducing a GC-optimized sequence for stabilization, followed by a stabilizing sequence derived from the albumin-3'-UTR, a stretch of 64 adenosines (poly(A)-sequence), a stretch of 30 cytosines (poly(C)-sequence), and a histone stem loop. The sequence (SEQ ID NO: 1) of the corresponding mRNA is shown in FIG. 1.

1.1.2. In Vitro Transcription of RNA

The respective DNA plasmid prepared according to section 1.1 above was transcribed in vitro using T7 RNA polymerase (Thermo Fisher Scientific Inc.). The in vitro transcription of influenza HA encoding R2564 was performed in the presence of a CAP analog ($m^7$GpppG). Subsequently the RNA was purified using PureMessenger® (CureVac, Tubingen, Germany; WO2008/077592A1).

1.1.3 Preparation of Standard RNA Solution

A standard RNA solution was prepared in purified water wherein the concentration of RNA was 0.87 g/L, further comprising about 9 mM Na and about 6.5 mM Cl. The ratio Na/RNA was about 10.3 mmol/g. The pH of the solution was 5.8.

In other experiments, a standard RNA solution was prepared in purified water, wherein the concentration of RNA was 0.87 g/L. The pH of the solution was 5.8.

1.2 Preparation of the Protamine Solution

For the model reaction used in all Examples and Reference Examples described in the following, a standard solution containing protamine (Meda Pharma) and trehalose (Ferro Pfanstiehl) was prepared in purified water. The concentration of protamine was 0.43 g/L (corresponding to 43.9 Units/mL), and the concentration of trehalose was 10.87% (w/w). For respective model reactions using that protamine solution comprising protamine obtained from Meda Pharma, the RNA solution did comprise additional NaCl (cf. 1.1.3).

For other Examples, GMP-grade protamine (LeoPharma GmbH; comprising 147 mM NaCl) was used. The concentration of GMP-grade protamine was 0.314 g/L (correspornding to 43.9 Units/mL of protamine), and the concentration of trehalose was 10.87% (w/w). For respective model reactions using the protamine solution comprising GMP-grade protamine, the RNA solution did not comprise additional NaCl (cf. 1.1.3).

Example 2—Characterisation of Product Dispersions 2.1 Characterization of Nanoparticles Measurement of Particle Size and Polydispersity The hydrodynamic diameter of the nanoparticles was measured by dynamic light scattering using a Zetasizer Nano ZS (Malvern Instruments, Malvern, UK) according to the instructions provided by the manufacturer. The measurements were performed at 25° C. and a scattering angle of 173° in the specified buffer analysed by a cumulant method to obtain the hydrodynamic diameters and polydispersity indices of the nanoparticles.

For measuring the particle size of the RNA-protamine nanoparticles obtained in dispersion according to the method of the present invention in the Examples and Reference Examples, 70 μl of the respective product solution was filled into a UV transmittable cuvette (UVette, Eppendorf), which in turn was placed into a Zetasizer nano ZS (Malvern instruments) and the measurement was conducted using the following settings: Refractive index of material: 1.450; absorption of material: 0.001; dispersant temperature: 25° C.; dispersant viscosity: 0.8753; dispersant refractive index: 1.331; Mark-Houwink parameters: A parameter 0.428; K-parameter $7.67^{-05}$ cm$^2$/s; use dispersant viscosity as sample viscosity; sample temperature: 25° C.; sample cuvette: Zen 0040 disposable cuvette, equilibration time: 0 s; measurement angle: 173° backscatter; automatic measurement duration; number of measurements: 1; automatic attenuation setting; positioning method: seek for optimal position; no extension duration for large particles; analysis model: normal resolution. The average particle size (hydrodynamic diameter of a particle in nm) is given as the Z-average and the polydispersity is given as the polydispersity index (PDI), both of which were calculated by the instrument's software (Zetasizer software version 6.34, Malvern Instruments).

2.2 Characterization of Product Solution 2.2.1 Measurement of the Absorption at 350 nm (A350)

The transmitted light through a sample solution can be measured in a UV-Vis spectrophotometer at a wavelength where the ingredients, such as proteins, peptides, DNA/RNA, and formulation excipients do not absorb light, i.e., typically in the range of 320-800 nm.

To rapidly measure and compare the clarity of the product nanoparticle dispersion (dispersion comprising the RNA-protamine nanoparticles), the absorption at 350 nm (A350) was determined. 200 μl of each product dispersion were applied to a microwell plate (Costar, UV Plate, 96 well, no lid, UV transmittable flat bottom). A350 was measured with a Synergy HT plate reader (BioTek systems). Pathlength correction was performed by Gen5 software (BioTek, Installation version: 1.11.5) with a test wavelength of 977 nm and a reference wavelength of 900 nm. Correction was performed with a constant K-factor of 0.18 to yield the A350 value corrected to 1 cm pathlength.

2.2.2 Photographic Documentation

Images of the plates from Example 2.2.1 were taken with an E-box VX2 (Vilber) documentation system.

2.2.3 Measurement of Turbidity (FNU)

The turbidity of the product nanoparticle dispersions was measured with a NEPHLA turbidimeter (Dr. Lange, Düsseldorf, Germany), operating at 860 nm and detecting at 90° angle. The system is calibrated with formazin as standard and the results were given in formazin nephelometric units (FNU). For the measurement, 2.0 ml of the formulations were analyzed.

Example 3—Characterization of Reactors

In the Examples and Reference Examples, the following reactors were used as exemplary embodiments of chemical reactors of different general design.

3.1 Reactor I—Non-Continuous Reactor (Non-Continuous Dynamic Mixer)

A well of a deep well plate (MegaBlock® 96 Well, 2.2 ml, polypropylene from Sarstedt) mounted on a shaking device (Multi-MicroPlate Genie from Scientific Industries) was used as an example of an open micro-reactor (Reactor I). Addition of the reagent solutions and removal of the product dispersion after reaction were carried out successively by means of a pipette.

3.2 Reactor II—Non-Continuous Reactor with Stirring Means (Non-Continuous Dynamic Mixer)

Figure 2:
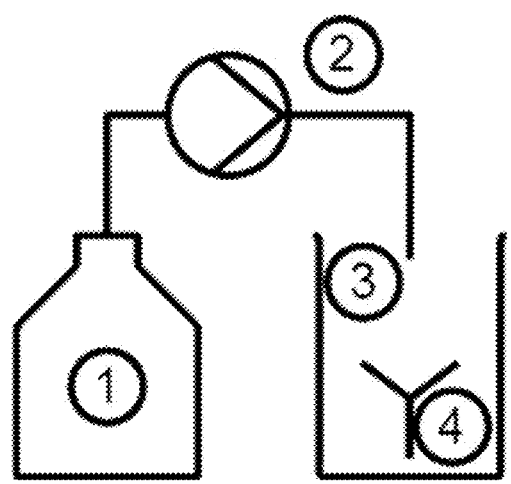
FIG. 2: Schematic flow diagram for a non-continuously operating reactor for the preparation of RNA-comprising nanoparticles. (1) feed vessel; (2) pump; (3) open tank; (4) stirrer. The reference signs do only apply to that particular figure and are not used continuously; the reference signs shall not be used, applied or translated to other figures and drawings.
Figure 3:
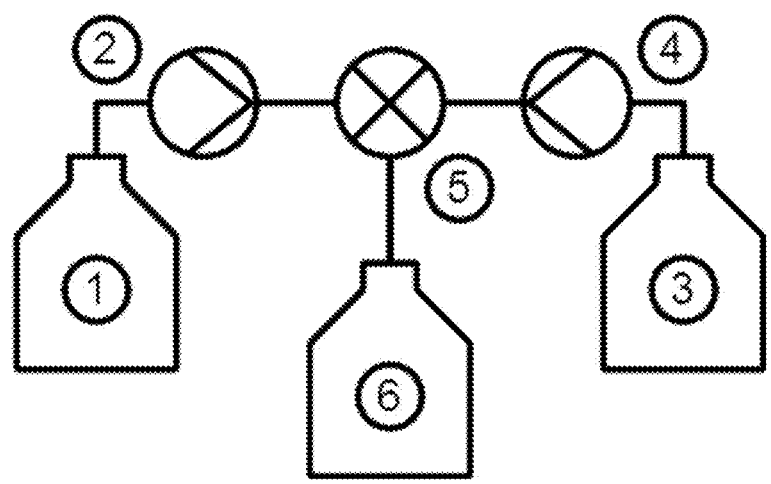
FIG. 3: Schematic flow diagram for a continuously operating stirred reactor for the preparation of RNA-comprising nanoparticles. (1) Feed vessel (for example for the solution comprising the cationic or polycationic compound); (2) Pump; (3) Feed vessel (for example for the RNA solution); (4) Pump; (5) continuously stirred tank; (6) Receiver vessel for the RNA-comprising nanoparticles. This vessel may be replaced by further processing modules.

A reactor (Tube 30 ml, 95×24.8 mm, polypropylene from Sarstedt,) equipped with a 1.7×0.4 mm stirring bar (VWR) mounted on a magnetic stirrer (500 or 1000 rpm, Thermo Compact 20, available from Thermo Fisher Scientific Inc) was used as an example of an open batch micro-reactor with stirring (Reactor II) The reactor design is schematically shown in FIG. 2, 3.15 mg of RNA (R2564) in a total volume of 605 μl resulting in an RNA concentration of 5.2 g/L were provided in the reactor. 3.66 ml of a protamine/trehalose mixture (0.235 g/L protamine, 5.92% w/w trehalose) were added with a syringe pump (TSE systems 540060-B) and an addition speed (flow rate) of 0.37 ml/min.

3.3 Reactor III—Continuous Reactor with Stirring Means/Design 1 (Continuous Dynamic Mixer)

An example of a continuously stirred micro-reactor (Reactor III) having a cylindrical reactor chamber with a volume of 400 μl (diameter: 12.5 mm; hight: 3.3 mm) was constructed from a 5 ml syringe with Luer lock (Braun Melsungen; Germany) and equipped with a cylindrical stirring bar (8×1.5 mm, VWR, Germany). The reactor design is schematically shown in FIG. 4, wherein the reactor body is indicated by reference sign (1) of FIG. 4, and the stirring bar is indicated by reference sign (6) of FIG. 4. Two inlet ports (reference signs 3, 4 of FIG. 4) for introducing the two reagent solutions were provided at opposite sides of the reactor chamber by means of butterfly needles pierced into the side wall of the chamber just below the top cover of the chamber, and an outlet port (reference sign 2 of FIG. 4) for recovering the product dispersion was provided by another butterfly needle attached to the Luer lock positioned in the top cover of the chamber. The chamber was mounted on a magnetic stirrer (reference sign (5) of FIG. 4, 200 or 1000 rpm, Thermo Compact 20, available from Thermo Fisher Scientific Inc). During operation, the additions of the reagent solutions were carried out by means of syringe pumps (TSE systems 540060-Bnot shown in FIG. 4) each with flow rates of 0.1 to 0.5 ml/min. (addition speed), while the removal of the product dispersion after reaction was achieved by the combined flow provided thereby.

3.4 Reactor IV—Continuous Reactor with Stirring Means/Design 2 (Continuous Dynamic Mixer)

An example of a continuously stirred micro-reactor (Reactor IV) having a cylindrical reactor chamber with a volume of 1500 µl (diameter: 15.89 mm; hight: 7.6 mm) was constructed from a 10 ml syringe with Luer lock (Braun Melsungen; Germany) and equipped with an oval stir bar (15×6 mmVWR, Germany). Two inlet ports for introducing the two reagent solutions were provided at opposite sides of the reactor chamber by means of butterfly needles pierced into the side wall of the chamber just below the top cover of the chamber, and an outlet port for recovering the product dispersion was provided by another butterfly needle attached to the Luer lock positioned at the bottom of the chamber. The chamber was mounted on a magnetic stirrer (200 or 1400 rpm, Thermo Compact 20, available from Thermo Fisher Scientific Inc). During operation, the addition of the reagent solutions were carried out by means of syringe pumps (TSE systems 540060-Beach with flow rates of 0.1 to 5 ml/min. (addition speed), while the removal of the product dispersion after reaction was achieved by the combined flow provided thereby.

3.5.1 Reactor V—Continuous Reactor with Stirring Means/Design 3 (Continuous Dynamic Mixer)

An example of a continuously stirred micro-reactor (Reactor V) having a cylindrical reactor chamber with a volume of 2.1 ml (diameter: 26 mm; hight: 4 mm) was constructed from stainless steel. The reactor design is schematically shown in FIG. 5, wherein the reactor body is indicated by reference sign (1, FIG. 5) and the cylindrical reaction chamber is indicated by reference sign (4, FIG. 5). The reactor comprises two inlet ports (reference signs 2, 3 of FIG. 5) for introducing the two reagent solutions, which are located at opposite sides of the reactor chamber, and an outlet port (reference sign 5 of FIG. 5) for recovering the product dispersion, which is located in the centre of the bottom of the chamber. Further, the reactor chamber was equipped with a cylindrical stir bar (Reference sign (7, FIG. 5), 8×3 mm, VWR, Germany), and the reactor chamber was mounted on a magnetic stirrer (reference sign (6, of FIG. 5), 200 or 1000 rpm, Thermo Compact 20, available from Thermo Fisher Scientific Inc.). The lid of the reactor chamber was tightly sealed with a seal ring (reference sign 9 of FIG. 5) made from polytetrafluoroethylene (PTFE) and provided with a ventilation means (reference sign 8 of FIG. 5) to allow for bubble-free filling of the reactor chamber, which was closed after complete filling of the reactor chamber. During operation, the addition of the reagent solutions were carried out by means of syringe pumps (TSE systems 540060-Bnot shown in FIG. 5) with flow rates of 0.1 to 0.5 ml/min. (addition speed), while the removal of the product dispersion after reaction was achieved by the combined flow provided thereby. A technical drawing of the reactor type V is provided in FIG. 13.

3.5.2 Reactor V.1—Continuous Reactor without Stirring Means/Design 3.2 (Continuous Static Mixer)

An adapted version of the continuous dynamic mixer according to 3.5.1. In some experiments, the reactor was used without a stir bar. A technical drawing of the reactor type V is provided in FIG. 13.

3.6 Reactor VI—Reactor with Static Mixing Means (Static Mixer)

An example of a reactor comprising a static mixing means (Reactor VI) was constructed. The static mixer consisted of a stainless steel housing with an inner diameter of 3.4 mm and a length of 30 mm. Inserted was a Sulzer SMX static mixer DN3 with a length of 22 mm and a diameter of 3.2 mm made of stainless steel.

The reactor principle is schematically shown in FIG. 6. A more detailed drawing is shown in FIG. 12. One opening of the tube is provided with two inlet ports for introducing the reagent solutions with pumps (not shown) at different flow rates. The reactor was connected to a neMESYS syringe pump (Cetoni) used for the introducing and mixing of 0.87 mg/ml RNA and protamine-trehalose solution (10.86% trehalose, 0.43 mg/ml protamine) in a plastic T-piece adapter and a stainless steel static mixing device from Sulzer (see above) (FIG. 6, FIG. 10 and FIG. 12). Both solutions were pumped through the static mixer with various total flow rates. The product dispersion is obtained after a reaction way of 22 mm.

3.7 Reactor VII—Reactor with Injector System as Mixing Means (Static Mixer)

An example of a reactor comprising a mixing means in form of an injector system (Reactor VII) was constructed by providing an inlet port at an angle a of 30° at the side wall of a tube reactor as shown in FIG. 11. [41.5 mm length, 6-3 mm reactor diameter, angle about 30°, diameter injection tube 0.5 mm) The two inlet ports are provided with a neMESYS syringe pump (Cetoni) (not shown) to provide the reagent solutions with different flow rates. The product dispersion is obtained after a reaction way of 41.5 mm.

3.8 Measurement of the Blend Time

The blend time was measured for each of the reactors I to V according to the following procedure. The reaction chamber was filled completely with a solution of 75% Glycerol/0.01 M NaOH/0.01% Bromophenol blue in water (solution 1). Under stirring (using a cylindrical stirring bar, (8×3 mm, VWR, Germany) and a magnetic stirrer (Thermo Compact 20, available from Thermo Fisher Scientific Inc.) (but without flow-through for reactors III to V), a volume of 0.01 M HCl corresponding to 0.01 volume equivalents of solution 1 were added and the time until the colour has changed from purple to yellow was recorded visually by a stop watch in quintuplicates.

The averaged blend rates measured for reactors I to V are summarised in Table 5.

In addition to the above described experimental procedure, the blend times of reactor types V and V.1 were determined using computational fluid dynamics (CFD) analysis for different conditions (e.g. different flow rates) (see Example 12).

Example 4: Preparation of RNA-Comprising Nanoparticles in Reactor I 130.5 µg of RNA (obtained in Example 1.1.2) in 30 µl water for injection were added to Reactor I (cf. Example 3.1). 270 µl of a protamine/trehalose solution (0.242 g/L protamine, 6.025% w/w trehalose in water for injection) were added stepwise by pipetting over 10 minutes (10 steps a 27 µl with dispensing and a 1 minute interval between each step) under shaking. After completion of the addition, the product dispersion was completely removed from the reactor by pipette and the product dispersion was analysed according to Example 2. The results are summarised in Table 5 and shown in FIGS. 7 and 8 as Experiment I.

Example 5: Preparation of RNA-Comprising Nanoparticles in Reactor II 3.15 mg of RNA (R2564, obtained in Example 1.1.2) in a total volume of 605 µl resulting in an RNA concentration of 5.2 g/L were added to Reactor II. 3.66 ml of a protamine/trehalose mixture (0.235 g/L protamine, 5.92% w/w trehalose) were added with a syringe pump and an addition speed (flow rate) of 0.37 ml/min. Mixing in the reactor was performed with a stir bar (500 or 1000 rpm). The reaction conditions are summarised in Table 1). After completion of the addition, the product dispersion was completely removed from the reactor by pipette and the product dispersion was analysed according to Example 2. The results are summarised in Table 5 and shown in FIGS. 7 and 8.

TABLE 1

Stir and addition rates for Reactor II

| Experiment number | Addition rate of protamine/trehalose solution (ml/min) | Total flow rate (ml/min) | Magnetic stirrer setting (rpm) |
|---|---|---|---|
| II.A | 0.37 | 0.37 | 500 |
| II.B | 0.37 | 0.37 | 1000 |

Example 6: Preparation of RNA-Comprising Nanoparticles in Reactor III

The standard RNA solution (0.87 g/L) prepared in Example 1.1.3 and the protamine/trehalose standard solution (0.43 g/L protamine; 10.87% trehalose) prepared in Example 1.2 were pumped into Reactor III with the flow and stir rates summarised in Table 2. The results are summarised in Table 5 and shown in FIGS. 7 and 8.

TABLE 2

Stir and addition rates for Reactor III

| Experiment number | Addition rate of RNA solution (ml/min) | Addition rate of protamine/trehalose solution (ml/min) | Total flow rate (ml/min) | Magnetic stirrer setting (rpm) |
|---|---|---|---|---|
| III.A | 0.1 | 0.1 | 0.2 | 200 |
| III.B | 0.5 | 0.5 | 1 | 200 |
| III.C | 0.1 | 0.1 | 0.2 | 1000 |
| III.D | 0.5 | 0.5 | 1 | 1000 |

Example 7: Preparation of RNA-Comprising Nanoparticles in Reactor IV

The standard RNA solution (0.87 g/L) prepared in Example 1.1.3 and the protamine/trehalose standard solution (0.43 g/L protamine; 10.87% trehalose) prepared in Example 1.2 were pumped into Reactor IV with the flow and stir rates summarised in Table 3. The results are summarised in Table 5 and shown in FIGS. 7 and 8.

TABLE 3

Stir and addition rates for Reactor IV

| Experiment number | Addition rate of RNA solution (ml/min) | Addition rate of protamine/trehalose solution (ml/min) | Total flow rate (ml/min) | Magnetic stirrer setting (U/min) |
|---|---|---|---|---|
| IV.A | 0.1 | 0.1 | 0.2 | 200 |
| IV.B | 0.1 | 0.1 | 0.2 | 1000 |
| IV.C | 5.5 | 5.5 | 11 | 1000 |

Example 8: Preparation of RNA-Comprising Nanoparticles in Reactor V

The standard RNA solution (0.87 g/L) prepared in Example 1.1.3 and the protamine/trehalose standard solution (0.43 g/L protamine; 10.87% trehalose) prepared in Example 1.2 were pumped into Reactor V with the flow and stir rates summarised in Table 4. The results are summarised in Table 5 and shown in FIGS. 7 and 8.

TABLE 4

Stir and addition rates for Reactor V

| Experiment number | Addition rate of RNA solution (ml/min) | Addition rate of protamine/trehalose solution (ml/min) | Total flow rate (ml/min) | Magnetic stirrer setting (U/min) |
|---|---|---|---|---|
| V.A | 0.5 | 0.5 | 1 | 200 |
| V.B | 0.1 | 0.1 | 0.2 | 1400 |
| V.C | 0.5 | 0.5 | 1 | 1400 |
| V.D | 1.5 | 1.5 | 3 | 1400 |
| V.E | 5 | 5 | 10 | 1400 |
| V.F | 1.5 | 1.5 | 3 | 1400 |
| V.G | 50 | 50 | 100 | 1400 |
| V.H | 50 | 50 | 100 | 1400 |
| V.I | 50 | 50 | 100 | 1400 |

Results

The results of the experiments described in Examples 4 to 8 are summarised in Table 5 and shown in FIGS. 7 and 8.

TABLE 5

Results of Examples 4 to 9

| Experiment number | Blend time [s] | A350 (pathlength corrected to 1 cm) | Z-average (diameter [nm]) | Polydispersity index |
|---|---|---|---|---|
| I* | 48 | 0.716 | 176 | 0.133 |
| II.A* | 4 | 0.242 | 115 | 0.131 |
| II.B* | 3 | 0.2 | 99 | 0.137 |
| III.A | 41 | 0.961 | 172 | 0.147 |
| III.B | 41 | 1.1 | 183 | 0.153 |
| III.C | 8 | 0.635 | 149 | 0.126 |
| III.D | 8 | 0.562 | 143 | 0.097 |
| IV.A | 17 | 0.781 | 155 | 0.164 |
| IV.B | 2.2 | 0.373 | 116 | 0.149 |
| IV.C | 2.2 | 0.485 | 130 | 0.109 |
| V.A | 13 | 0.526 | 148 | 0.160 |
| V.B | 2 | 0.331 | 120 | 0.141 |
| V.C | 2 | 0.346 | 135 | 0.179 |
| V.D | 2 | 0.295 | 115 | 0.096 |
| V.E | 2 | 0.323 | 121 | 0.139 |

TABLE 5-continued

Results of Examples 4 to 9

| Experiment number | Blend time [s] | A350 (pathlength corrected to 1 cm) | Z-average (diameter [nm]) | Polydispersity index |
|---|---|---|---|---|
| V.F | >0.1$ | 0.44 | 135 | 0.14 |
| V.G | >0.1$ | 0.24 | 126 | 0.09 |
| V.H | >0.1$ | 0.26 | 116 | 0.11 |
| V.I | >0.1$ | 0.27 | 112 | 0.14 |

*reaction performed non-continuously
$approximation

From the data summarised in Table 5 and shown in FIGS. 7 and 8, the following may be deduced.

Using a pipette and microplate shaker for mixing without stirring the solution (method I, Example 4) resulted in samples of low clarity/high turbidity (FIG. 7) with A350 values above 0.5 and in large RNA/protamine nanoparticles/complexes with a Z-average above 150 nm (Table 5 and FIG. 8).

In contrast, when protamine was added to an RNA solution at a constant flow rate and under stirring according to the method of the present invention (Method II, Example 5), the product dispersion was significantly clearer than with Method I (FIG. 7) with A350 values well-below 0.5 and the particles sizes were decreased to sizes of about 120 nm (Table 5 and FIG. 8).

When using one of the five configurations of dynamic mixers (stirred reactors; Reactors I, II, III, IV and V), the product quality is controlled by the blend time.

Reactor III (Example 4) exhibits a blend time of more than 40 s when the stirring means is operated at 200 rpm, and a blend time of 8 s when the stirring means is operated at 1000 rpm. In both cases, the product dispersions were turbid with precipitating material observed at the lowest mixing efficiency (blend time >40 s and 1 ml/min total flow rate). Clear dispersions and A350 values below 0.5 could not be achieved under these conditions. In contrast, Reactor IV (Example 5) exhibits lower blend times, namely a blend time of 17 s when the stirring means is operated at 200 rpm, and a blend time of 2 s when the stirring means is operated at 1000 rpm. Using this reactor in the method according to the present invention, clear product dispersions having an A350 of less than 0.5 are obtained, independent of the total flow rates of 0.2 ml/ml and 11 ml/min but dependent on the stirring rate.

For scaling-up the production process, Reactor V exhibiting further decreased blend times (Example 6), namely a blend time of 13 s when the stirring means is operated at 200 rpm, and a blend time of 2 s when the stirring means is operated at 1400 rpm, was used in the method according to the present invention. Thus, clear product dispersions having an A350 of less than 0.5 and particle sizes of about 120 nm were obtained with flow rates from 0.2 to 10 ml/min, when the stir rate was 1400 rpm. However, with a stir rate of 200 rpm, the product dispersion was less clear with an A350 value of about 0.5.

In addition, higher flow rates were tested (V.F–V.I). Those experiments clearly show that a higher flow rate resulted in dispersions with less precipitates and also smaller and more uniform nanoparticle sizes. The blend time in this setup (100 ml/min flow rate, 1400 rpm stirring) was estimated to be shorter than 0.1 seconds.

To determine the blend time in setups with higher flow rates, CFD analysis for 50 ml/min and 160 ml/min flow rates were conducted (see Example 12).

It has to be noted that only for blend times shorter than 5 seconds, nanoparticles containing products could be generated while avoiding the formation of precipitates (A350 smaller than 0.5; cf. FIG. 7; reactions with precipitates are indicated with an asterisk). In addition, it has been surprisingly found that increasing the blend time decreased the precipitation and therefore the quality of the product solution.

In summary, the above examples demonstrate that only the product dispersions obtained by the method according to the present invention exhibit the properties required for use of the RNA in the medical field, as well as the required production reproducibility.

Example 9: Preparation of RNA-Comprising Nanoparticles in Reactor VI

The standard RNA solution (0.87 g/L) prepared in Example 1.1.3 and the protamine/trehalose standard solution (0.43 g/L protamine; 10.87% trehalose) prepared in Example 1.2 were pumped into Reactor VI with the total flow rates, which are summarised in Table 6 together with the average particle sizes (zetasizer, Z-avarages), polydispersity index (PDI), absorption at 350 nm (A350) and turbidity, determined according to Example 2.

TABLE 6

Results and parameters for Reactor VI

| Experiment number | total flow rate [μl/s] | Z-avarage (diameter [nm]) | PDI | A350 | Turbidity [FNU] |
|---|---|---|---|---|---|
| VI.A | 240 | 86.1 | 0.259 | 0.097 | 7.8 |
| VI.B | 300 | 186.6 | 0.239 | 0.258 | 39.0 |
| VI.C | 500 | 161.9 | 0.247 | 0.235 | 35.5 |

Results: In all performed experiments, it could be shown that particles smaller than 200 nm in average were generated in clear dispersions, without causing increased precipitation (A350<0.5). Lower flow rates seem to correlate with smaller particle sizes and less precipitation (low A350 nm values).

Example 10: Preparation of RNA-Comprising Nanoparticles in Reactor VII

The standard RNA solution (0.87 g/L) prepared in Example 1.1.3 and the protamine/trehalose standard solution (0.43 g/L protamine; 10.87% trehalose) prepared in Example 1.2 were pumped into Reactor VII with the total flow rates summarised in Table 7 together with the average particle sizes (zetasizer, Z-avarages), polydispersity index (PDI), absorption at 350 nm (A350) and turbidity, determined according to Example 2. Experiments with flow rates of 400 μl/s and 550 μl/s were repeated.

TABLE 7

Results and parameters for Reactor VII

| Experiment number | total flow rate [μl/s] | Z-avarage (diameter [nm]) | PDI | (A350) OD 350 nm | Turbidity [FNU] |
|---|---|---|---|---|---|
| VII.A | 200 | 253.8 | 0.338 | 0.729 | 161.4 |
| VII.B | 275 | 153.0 | 0.176 | 0.533 | 101.5 |
| VII.C | 400 | 145.0 | 0.188 | 0.437 | 79.4 |
| VII.C-2* | 400 | 166.3 | 0.231 | 0.389 | 72.9 |
| VII.D | 440 | 96.6 | 0.180 | 0.172 | 17.2 |
| VII.E | 550 | 90.9 | 0.180 | 0.130 | 10.0 |
| VII.E-2* | 550 | 78.6 | 0.153 | 0.101 | 6.1 |
| VII.F | 600 | 70.4 | 0.153 | 0.089 | 4.6 |

*experiment repeated

Results: In the performed injector mixing experiments, it could be shown that particles larger than 200 nm in average were generated with flow rates of 200 µl/s. The absorption at 350 nm (A350) moreover indicates that also precipitation occurred using such low flow rates. Both, the average particle size, and the A350 values decreased by increasing flow rates. With flow rates between 400 and 600 µl/s, on average a particle size smaller than 200 nm and an A350 value below 0.5 could be reached, and therefore define a preferred range.

In summary, the above examples demonstrate that only the product dispersions obtained by the method according to the present invention exhibit the properties required for RNA therapeutics, as well as the required production reproducibility.

Example 11: Stimulation of Cytokines in Peripheral Blood Mononuclear Cells

In this test of immunostimulation, the dispersions comprising RNA (R2564)-protamine nanoparticles obtained in Experiments II.A and V.D were used. For a formulation with free RNA, the dispersions were supplemented with R2564 to yield final concentrations of 0.4 g/L RNA complexed with 0.2 g/L protamine and 0.4 g/L free RNA.

The samples were lyophilized (Christ Alpha I) and reconstituted in Ringer lactate (in the volume of the sample before lyophilization). Peripheral blood mononuclear cells (PBMCs) from healthy human subjects were isolated by density gradient centrifugation and aliquots were cryopreserved in liquid nitrogen. On the day of the stimulation, PBMCs were thawed and $2 \times 10^5$ cells seeded in each well of a 96 flat bottom plate in 200 µl X-Vivo 15 serum-free medium supplemented with 100 lUm/ml penicillin/streptomycin (both Lonza). Cells were stimulated with R2564/II.A and R2564/V.D (concentration range: 114 to 14.2 nM). Untreated cells were used as control. After 24 hours, cell-free supernatants were collected and the concentrations of TNF, IFN-α and IL-12p70 were measured by Cytometric Bead Array (CBA) according to manufacturer's instructions (BD Biosciences; cf. Table 8) using the kits of Table 8. Samples were acquired on a BD FACS Canto™ (BD Biosciences) and the data was analyzed using the FCAP Array v3.0 software (BD Biosciences). Both formulations showed comparable immunostimulation in cell assays (FIG. 9).

TABLE 8

Kits from BD Biosciences used for measurement of cytokines in cell culture supernatants.

| Reagent | Catalog number |
| --- | --- |
| Human Soluble Protein Master Buffer Kit | 558264 |
| Assay Diluent | 560104 |
| Human IFNα Flex Set | 560379 |
| Human IL-12p70 Flex Set | 558283 |
| Human TNF Flex Set | 560112 |

Results:
RNA-comprising nanoparticles produced by both methods according to the method of the present invention were shown to induce comparable cytokine levels in hPBMCs.

In summary, it is demonstrated that the method according to the present invention produces nanoparticles, which are characterised by having uniform average particles sizes and polydispersity, reliably under controlled conditions, without allowing unwanted side reactions resulting in unwanted side products (e.g. precipitates) and stability problems caused thereby, independent of the scale of production. Further, the method according to the present invention is both cost-effective and reliable, even on a large scale, which renders the method of the invention especially suitable for the pharmaceutical production of RNA-comprising nanoparticles on an industrial level.

Example 12: CFD Simulations of Reactor Types V and V.1

A computational fluid dynamics (CFD) analysis was performed in order to determine the influence of flow-rate and mixing reactor geometry on the blending of the RNA solution and the protamine-trehalose solution. CFD analysis was performed using a Star CCM+ software package.

In the computational model, the physical characteristics of the RNA solution were assigned with a density of 997.9 kg/m$^3$ and a kinematic viscosity of 2.39 mm$^2$/s; the physical characteristics of the protamine-trehalose solution were assigned with a density of 1039.4 kg/m$^3$ and a kinematic viscosity of 1.206 mm$^2$/s.

The CFD analysis was performed for models of reactor type V (continuous reactor with stirring means) and reactor type V.1 (continuous reactor without stirring means) (see FIG. 14 and FIG. 16).

The blend time at different flow rates for certain reactor models was determined according to the volume fraction of the protamine/trehalose solution at the outlet port. Using this method, the homogeneity of the product liquid composition was simulated over time (an exemplary result is shown in FIG. 15). The blend time was determined as the time point, where the mixture of both solutions showed a homogeneity/uniformity of at least 80% (or 0.8).

Results:

In the CFD analysis, different parameters such as speed distribution at different flow rates and medium distribution in the reactor models were analysed. The parameters included into the model, as well as the obtained results are summarized in Table 9. FIG. 15 and FIG. 16 shows an exemplary result of how the blend time has been determined.

TABLE 9

Results of Examples 12

| Experiment number | Reactor type | Blend time [s] | Flow rate [ml/min] | Stirrer (U/min) |
| --- | --- | --- | --- | --- |
| 1 | V | <1 | 50 | 1400 |
| 2 | V | <0.04 | 160 | 1400 |
| 3 | V.1 | ## | 10 | |
| 4 | V.1 | <0.04 | 160 | |

: A homogeneity level of 80% could not be achieved; therefore the blend time could not be determined (see FIG. 16).

In summary, the results of the CFD simulation show that a fast and stable formulation of the first and the second liquid composition can be obtained with both reactor types at high flow rates (correlating to short blend times). Surprisingly it has been found that a blend time shorter than 1 second (at a flow rate of 50 ml/min) or a blend time shorter than 0.04 seconds (at flow rates of 160 ml/min) was sufficient to obtain a homogeneous and uniform mixture.

The invention claimed is:

1. A method for producing a liquid composition comprising a nanoparticle comprising at least one long-chain RNA and at least one cationic or polycationic compound,
   wherein the method comprises the steps of:
   (a) providing a first liquid composition comprising the at least one long-chain RNA that comprises from 200 to 15,000 nucleotides,
   (b) providing a second liquid composition comprising the at least one cationic or polycationic compound,
   (c) introducing the first liquid composition and the second liquid composition into at least one reactor, wherein the first liquid composition and/or the second liquid composition are introduced at a flow rate of at least 5 mL/minute, and
   (d) recovering the product liquid composition comprising the nanoparticles comprising the at least one long-chain RNA and the at least one cationic or polycationic compound from the reactor.

2. The method according to claim 1, wherein the product liquid composition comprising the nanoparticle comprising the at least one long-chain RNA and the at least one cationic or polycationic compound comprises RNA in an amount of at least 1 g.

3. The method according to claim 1, wherein the at least one long-chain RNA comprises from 300 to 10,000 nucleotides.

4. The method according to claim 3, wherein the at least one long-chain RNA is an mRNA.

5. The method according to claim 1, wherein the nanoparticles comprising the at least one long-chain RNA and the at least one cationic or polycationic compound have a particle size of 300 nm or less.

6. The method according to claim 5, wherein the reactor comprises at least one dynamic mixing means.

7. The method according to claim 5, wherein the reactor comprises at least one static mixing means.

8. The method according to claim 5, wherein the reactor comprises at least one T-piece adapter.

9. The method according to claim 8, wherein the nanoparticle comprising the at least one long-chain RNA and the at least one cationic or polycationic compound has a polydispersity index in a range from 0.05 to 0.50.

10. The method according to claim 9, wherein the first liquid composition and the second liquid composition are mixed with a blend time of 5 seconds or less.

11. The method according to claim 8, wherein the at least one cationic or polycationic compound is selected from the group consisting of a cationic or polycationic peptide, a cationic or polycationic protein, a cationic or polycationic polyamino acid, a cationic or polycationic carbohydrate, a cationic or polycationic synthetic polymer, a cationic or polycationic small synthetic organic molecule, an inorganic multivalent cation, a cationic or polycationic lipid, a cationic or polycationic polyamine compound, and a cationic or polycationic polyimine compound.

12. The method of claim 11, wherein the at least one cationic or polycationic compound is a cationic or polycationic polyamino acid.

13. The method of claim 11, wherein the at least one cationic or polycationic compound is a cationic or polycationic carbohydrate.

14. The method of claim 11, wherein the at least one cationic or polycationic compound is a cationic or polycationic synthetic polymer.

15. The method of claim 11, wherein the at least one cationic or polycationic compound is a cationic or polycationic lipid.

16. The method of claim 11, wherein the at least one cationic or polycationic compound is a cationic or polycationic polyamine compound.

17. The method according to claim 5, wherein the first liquid composition and the second liquid composition are added to the at least one reactor so that the at least one cationic or polycationic compound and the at least one long-chain RNA are present in the reactor with an N/P-ratio in a range from 0.1 to 10.

18. The method according to claim 17, wherein the method is conducted continuously.

19. The method according to claim 17, wherein the first liquid composition and/or the second liquid composition are introduced into the at least one reactor with a flow rate of 10 mL/minute or more.

20. The method according to claim 19, wherein the first liquid composition and/or the second liquid composition are introduced into the at least one reactor via a pump device.

21. The method according to claim 20, wherein the first liquid composition and the second liquid composition are concurrently introduced into the at least one reactor.

22. The method according to claim 21, further comprising a step (e) of isolating or concentrating the nanoparticle comprising the at least one long-chain RNA and the at least one cationic or polycationic compound from the product liquid composition comprising the nanoparticle comprising the at least one long-chain RNA and the at least one cationic or polycationic compound.

23. The method according to claim 22, wherein step (e) comprises a drying step.

24. The method according to claim 21, wherein the product liquid composition comprising the nanoparticle comprising the at least one long-chain RNA and the at least one cationic or polycationic compound further comprises a pharmaceutically acceptable carrier.

25. The method of claim 17, wherein step (c) comprises introducing the first liquid composition and the second liquid composition into the at least one reactor with a combined flow rate of at least 250 ml/min.

26. The method of claim 25, wherein the nanoparticles comprising the at least one long-chain RNA and the at least one cationic or polycationic compound have a particle size of 50 to 200 nm and a polydispersity index (PDI) of 0.4 or below.

27. The method of claim 26, wherein then nanoparticles comprising the at least one long-chain RNA and the at least one cationic or polycationic compound have a particle size of 50 to 150 nm.

28. The method of claim 27, wherein then nanoparticles comprising the at least one long-chain RNA and the at least one cationic or polycationic compound have a PDI of from 0.10 to 0.30.

29. The method of claim 28, wherein then nanoparticles comprising the at least one long-chain RNA and the at least one cationic or polycationic compound have a PDI of 0.2 or below.

30. The method of claim 28, wherein the reactor comprises at least one T-piece adapter.

31. The method of claim 28, wherein the at least one reactor has a volume in a range from 0.1 ml to 10 L.

32. The method of claim 31, wherein the at least one reactor has a volume in a range from 1 ml to 5 L.

33. The method of claim 31, wherein introducing the first liquid composition and the second liquid composition comprises pumping the first liquid composition and the second liquid composition from a first reservoir and a second reservoir that are each maintained at a predetermined temperature and pressure.

34. The method of claim 17, wherein step (c) comprises introducing the first liquid composition and the second liquid composition into the at least one reactor with a combined flow rate of 100-800 ml/min.

35. The method according to claim 1, wherein the first liquid composition and/or the second liquid composition further comprise at least one compound selected from a salt or a lyoprotectant.

* * * * *

SEQUENCE LISTING

<160> NUMBER OF SEQ ID NOS: 4

<210> SEQ ID NO 1
<211> LENGTH: 2083
<212> TYPE: RNA
<213> ORGANISM: Artificial Sequence
<220> FEATURE:
<223> OTHER INFORMATION: R2564: mRNA encoding Influenza HA

<400> SEQUENCE: 1

```
ggggcgcugc cuacggaggu ggcagccauc uccuucucgg caucaagcuu accaugaagg     60
ccauccuggu gguccuccug uacaccuucg ccaccgcgaa cgccgacacg cugugcaucg    120
gcuaccacgc caacaacagc accgacaccg uggacaccgu gcucgagaag aacgucacgg    180
ugacccacuc cgugaaccug cuggaggaca agcacaacgg gaagcucugc aagcugcggg    240
gcgucgcccc gcugcaccuc gggaagugca acaucgccgg cuggauccug gggaacccgg    300
agugcgagag ccuguccacc gcgagcuccu ggagcuacau cguggagacc uccagcuccg    360
acaacggcac gugcuacccc ggcgacuuca ucgacuacga ggagcuccgc gagcagcuga    420
gcuccgugag cuccuucgag cgguucgaga ucuuccccaa gaccagcucc uggcccaacc    480
acgacagcaa caagggggguc accgccgccu gcccgcacgc cggcgcgaag uccuucuaca    540
agaaccugau cuggcucgug aagaagggga acagcuaccc caagcugucc aagagcuaca    600
ucaacgacaa gggcaaggag gugcuggucc ucuggggggau ccaccacccc agcaccuccg    660
ccgaccagca gagccuguac cagaacgccg acgccuacgu guucgugggc uccagccgcu    720
acuccaagaa guucaagccc gagaucgcca uccggccgaa gguccgcgac caggagggcc    780
ggaugaacua cuacuggacg cugguggagc ccggggacaa gaucaccuuc gaggcgaccg    840
gcaaccucgu gguccccccgc uacgccuucg ccauggagcg gaacgccggg agcggcauca    900
ucaucuccga cacccccgug cacgacugca acacgaccug ccagaccccg aagggcgcca    960
ucaacaccag ccugcccuuc cagaacaucc accccaucac gaucgggaag ugccccaagu   1020
acgugaaguc caccaagcug cgccucgcga ccggccugcg gaacgucccg agcauccagu   1080
cccgcgggcu guucggcgcc aucgccgggu ucaucgaggg cggcuggacc gggaugguugg   1140 acggcuggua cggguaccac caccagaacg agcagggcag cggguacgcc gccgaccuca   1200
aguccacgca gaacgcgauc gacgagauca ccaacaaggu gaacagcguc aucgagaaga   1260
ugaacaccca guucaccgcc gugggcaagg aguucaacca ccuggagaag cggaucgaga   1320
accugaacaa gaaggucgac gacggcuucc ucgacaucug gacguacaac gccgagcugc   1380
uggugcuccu ggagaacgag cgcacccugg acuaccacga cuccaacgug aagaaccucu   1440
acgagaaggu ccggagccag cugaagaaca acgccaagga gaucgggaac ggcugcuucg   1500
aguucuacca caagugcgac aacaccugca uggaguccgu gaagaacggg accuacgacu   1560
accccaagua cagcgaggag gccaagcuga accgcgagga gaucgacggc gugaagcucg   1620
aguccacgcg gaucuaccag auccuggcga ucuacagcac cgucgccagc ucccuggugc   1680
ucguggucag ccugggggcc aucuccuucu ggaugugcag caacggcucc cugcagugcc   1740
gcaucugcau cugaccacua gugcaucaca uuuaaaagca ucucagccua ccaugagaau   1800
aagagaaaga aaaugaagau caauagcuua uucaucucuu uuucuuuuuc guugguguaa   1860
agccaacacc cugucuaaaa aacauaaauu ucuuuaauca uuuugccucu uuucucugug   1920
cuucaauuaa uaaaaaaugg aaagaaccua gaucuaaaaa aaaaaaaaaa aaaaaaaaaa   1980
aaaaaaaaaa aaaaaaaaaa aaaaaaaaaa aaaaaaaaau gcauccccc cccccccccc   2040
```

```
cccccccccc cccccaaagg cucuuuucag agccaccaga auu            2083
```

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide - Exemplary oligopeptide
      according to formula V
<220> FEATURE:
<221> NAME/KEY: MISC_FEATURE
<222> LOCATION: (4)..(4)
<223> OTHER INFORMATION: Xaa is Orn
<220> FEATURE:
<221> NAME/KEY: MISC_FEATURE
<222> LOCATION: (5)..(5)
<223> OTHER INFORMATION: Xaa is any amino acid except Arg, Lys, His,
      or Orn

<400> SEQUENCE: 2

Arg Lys His Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide - Exemplary oligopeptide
      according to formula Va
<220> FEATURE:
<221> NAME/KEY: MISC_FEATURE
<222> LOCATION: (4)..(4)
<223> OTHER INFORMATION: Xaa is Orn
<220> FEATURE:
<221> NAME/KEY: MISC_FEATURE
<222> LOCATION: (5)..(5)
<223> OTHER INFORMATION: Xaa is any amino acid except Arg, Lys, His,
      Orn, or Cys

<400> SEQUENCE: 3

Arg Lys His Xaa Xaa Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide - Exemplary oligopeptide
      according to formula Vb
<220> FEATURE:
<221> NAME/KEY: MISC_FEATURE
<222> LOCATION: (5)..(5)
<223> OTHER INFORMATION: Xaa is Orn
<220> FEATURE:
<221> NAME/KEY: MISC_FEATURE
<222> LOCATION: (6)..(6)
<223> OTHER INFORMATION: Xaa is any amino acid except Arg, Lys, His,
      Orn, or Cys

<400> SEQUENCE: 4

Cys Arg Lys His Xaa Xaa Cys
1               5